United States Patent
Golynskiy et al.

(10) Patent No.: US 10,329,545 B2
(45) Date of Patent: Jun. 25, 2019

(54) POLYMERASES

(71) Applicant: Illumina, Inc., San Diego, CA (US)

(72) Inventors: Misha Golynskiy, San Diego, CA (US);
Molly He, San Diego, CA (US);
Michael Previte, San Diego, CA (US);
BeiBei Wang, San Diego, CA (US);
Sergio Peisajovich, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 15/526,386

(22) PCT Filed: Nov. 13, 2015

(86) PCT No.: PCT/US2015/060741
§ 371 (c)(1),
(2) Date: May 12, 2017

(87) PCT Pub. No.: WO2016/077795
PCT Pub. Date: May 19, 2016

(65) Prior Publication Data
US 2017/0321195 A1 Nov. 9, 2017

Related U.S. Application Data

(60) Provisional application No. 62/080,089, filed on Nov. 14, 2014.

(51) Int. Cl.
*C12N 9/12* (2006.01)
*C12P 19/34* (2006.01)

(52) U.S. Cl.
CPC ............ *C12N 9/1252* (2013.01); *C12P 19/34* (2013.01); *C07K 2319/21* (2013.01)

(58) Field of Classification Search
None
See application file for complete search history.

(56) References Cited

U.S. PATENT DOCUMENTS

| | | | |
|---|---|---|---|
| 5,405,774 A | 4/1995 | Abramson et al. | |
| 5,455,170 A | 10/1995 | Abramson et al. | |
| 5,614,365 A | 3/1997 | Tabor et al. | |
| 5,795,762 A | 8/1998 | Abramson et al. | |
| 6,395,524 B2 | 5/2002 | Loeb et al. | |
| 7,312,059 B2 | 12/2007 | Loeb et al. | |
| 7,598,032 B2 | 10/2009 | Gelfand et al. | |
| 8,481,685 B2 * | 7/2013 | Bourn ................. | C12N 9/1252 435/183 |
| 8,852,910 B2 | 10/2014 | Smith et al. | |
| 8,921,086 B2 * | 12/2014 | Hanzel ................. | C12N 9/1252 435/194 |
| 9,447,389 B2 | 9/2016 | Smith et al. | |
| 2003/0228616 A1 | 12/2003 | Arezi et al. | |

FOREIGN PATENT DOCUMENTS

| | | |
|---|---|---|
| WO | WO 01/32887 A1 | 5/2001 |
| WO | WO 01/92501 A1 | 12/2001 |
| WO | WO 2004/038007 A2 | 5/2004 |
| WO | WO 2007/076057 A2 | 7/2007 |
| WO | WO 2008/051530 A2 | 5/2008 |
| WO | WO 2010/062776 A2 | 6/2010 |

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
GENESEQ (Database), "T. Waiotapuensis DNA Polymerase, SEQ ID 21", XP002754665 retrieved from EBI accession No. GSP:BAS79710 Database accession No. BAS79710 sequence, Oct. 24, 2013.
Altschul et al., "Basic local alignment search tool," *J. Mol. Biol.*, Oct. 5, 1990; 215(3):403-410.
Arezi et al., "Compartmentalized self-replication under fast PCR cycling conditions yields Taq DNA polymerase mutants with increased DNA-binding affinity and blood resistance," *Front. Microbiol.*, Aug. 2014; 5(408):1-10.
Barnes, "The fidelity of Taq polymerase catalyzing PCR is improved by an N-terminal deletion," *Gene*, 1992; 112:29-35.
Cariello et al., "Fidelity of *Thermococcus litoralis* DNA polymerase (Vent) in PCR determined by denaturing gradient gel electrophoresis," *Nucleic Acids Research*, 1991; 19(15):4193-4198.
Chien et al., "Deoxyribonucleic acid polymerase from the extreme thermophile *Therms aquaticus*," *Journal of Bacteriology*, 1976; 127(3):1550-1557.
Cline et al., "PCR fidelity of pfu DNA polymerase and other thermostable DNA polymerases," *Nucleic Acids Research*, 1996; 24(18):3546-3551.
Cho et al., "Characterization and PCR application of a new high-fidelity DNA polymerase from Thermococcus waiotapuensis," *Enzyme Microb. Technol.*, 2012; 51(6-7):334-341.
Diaz and Sabino, "Accuracy of replication in the polymerase chain reaction. Comparison between Thermotoga maritima DNA polymerase and Thermus aquaticus DNA polymerase," *Braz. J. Med. Res.*, 1998; 31:1239.
Elshawadfy et al., "DNA polymerase hybrids derived from the family-B enzymes of *Pyrococcus furiosus* and *Thermococcus kodakarensis*: improving performance in the polymerase chain reaction," *Front. Microbiol.*, May 2014; 5(244):1-14.
Henikoff and Henikoff, "Amino acid substitution matrices from protein blocks," *Proc. Natl. Acad. Sci. USA*, Nov. 1992; 89:10915-10919.
Hopfner, et al., "Crystal structure of a thermostable type B DNA polymerase from *Thermococcus gorgonarius*," Mar. 1999, *Proc. Natl. Acad. Sci. USA*; 96:3600-3605.

(Continued)

*Primary Examiner* — Richard G Hutson
(74) *Attorney, Agent, or Firm* — Mueting, Raasch & Gebhardt, P.A.

(57) ABSTRACT

Presented herein are methods and compositions for thermostable DNA polymerases that may be used to improve the PCR process and to improve the results obtained when using a thermostable DNA polymerase in other recombinant techniques such as DNA sequencing, nick-translation, and reverse transcription.

19 Claims, 1 Drawing Sheet
Specification includes a Sequence Listing.

(56) References Cited

OTHER PUBLICATIONS

Juncosa-Ginesta et al., "Improved efficiency in site-directed mutagenesis by PCR using a *Pyrococcus* sp. GB-D polymerase," 1994, *Biotechniques*, 16(5):820.
Karlin and Altschul, "Applications and statistics for multiple high-scoring segments in molecular sequences," *Proc. Natl. Acad. Sci. USA*, Jun. 15, 1993; 90(12):5873-7.
Lecomte and Doubleday, "Selective inactivation of the 3' to 5' exonuclease activity of *Escherichia coli* DNA polymerase I by heat," *Nucleic Acids Research*, 1983; 11(21):7505-7515.
Lundberg et al., "High-fidelity amplification using a thermostable DNA polymerase isolated from Pyrococcus furiosus," *Gene*, 1991; 180(1):1-6.
Myers and Gelfand, "Reverse transcription and DNA amplification by a Thermus thermophilus DNA polymerase," *Biochemistry*, Aug. 1991; 30(31):7661-6.
Needleman and Wunsch, "A general method applicable to the search for similarities in the amino acid sequence of two proteins," *J. Mol. Biol.*, Mar. 28, 1970; 48(3):443-453.
Nordstrom et al., "Characterization of bacteriophage T7 DNA polymerase purified to homogeneity by antithioredoxin immunoadsorbent chromatography," *J. Biol. Chem.*, 1981; 256(6):3112-3117.
Pearson and Lipman, "Improved tools for biological sequence comparison," *Proc. Nat'l. Acad. Sci. USA*, Apr. 1988; 85(8):2444-2448.
Smith and Waterman, "Comparison of biosequences," *Adv. Appl. Math.*, Dec. 1981; 2(4):482-489.
Stenesh and McGowan, "DNA polymerase from mesophilic and thermophilic bacteria. III. Lack of fidelity in the replication of synthetic polydeoxyribonucleotides by DNA polymerase from Bacillus licheniformis and Bacillus stearothermophilus," *Biochim. Biophys. Acta.*, 1977; 475:32-41.
Takagi et al., "Characterization of DNA polymerase from *Pyrococcus* sp. strain KOD1 and its application to PCR," *Appl. Environ. Microbiol.*, 1997; 63(11):4504-4510.
Tindall et al., "Fidelity of DNA synthesis by the Thermus aquaticus DNA polymerase," *Biochemistry*, 1988; 27:6008-6013.
International Search Report and Written Opinion, PCT/US2015/060741, 14 pages, dated Mar. 11, 2016.
International Preliminary Report on Patentability, PCT/US2015/060741, 8 pages, dated May 16, 2017.

\* cited by examiner

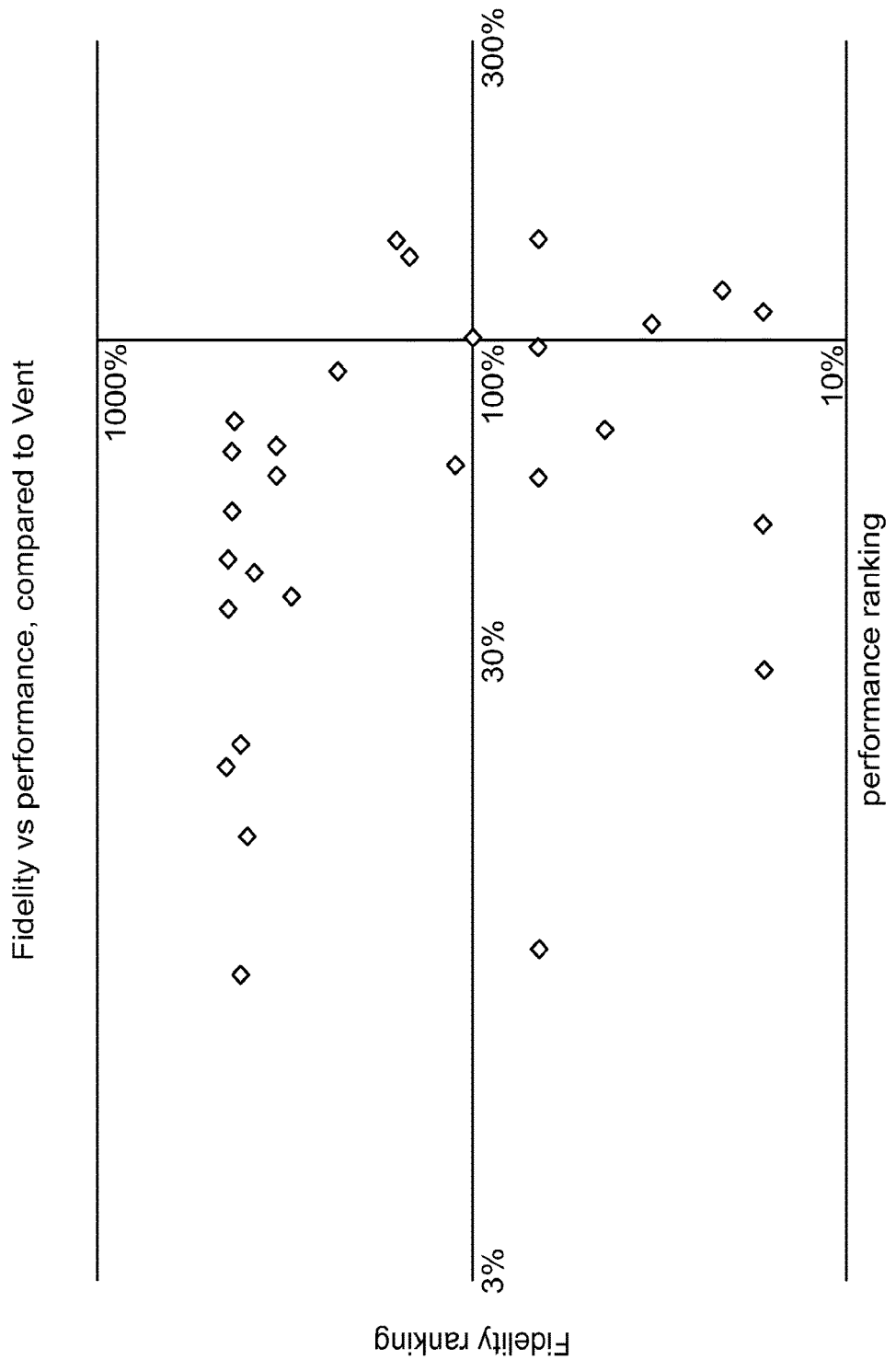

POLYMERASES

This application is the § 371 U.S. National Stage of International Application No. PCT/US2015/060741, filed Nov. 13, 2015, which claims the benefit of U.S. Provisional Application No. 62/080,089, filed Nov. 14, 2014, the disclosures of which are incorporated by reference herein in their entireties.

BACKGROUND

Thermostable enzymes are useful to amplify existing nucleic acid sequences in amounts that are large compared to the amount initially present. Primers, template, nucleotide triphosphates, the appropriate buffer and reaction conditions, and polymerase are used in the PCR process, which involves denaturation of target DNA, hybridization of primers, and synthesis of complementary strands. The extension product of each primer becomes a template for the production of the desired nucleic acid sequence. If the polymerase employed is a thermostable enzyme, then polymerase need not be added after every denaturation step, because heat will not destroy the polymerase activity.

Prior work has demonstrated the isolation of thermostable DNA polymerase from *Thermus aquaticus* and the use of that polymerase in PCR. Although *T. aquaticus* DNA polymerase is especially preferred for use in PCR and other recombinant DNA techniques, there remains a need for other thermostable polymerases.

Accordingly, there is a desire in the art to produce a purified, thermostable DNA polymerase that may be used to improve the PCR process described above and to improve the results obtained when using a thermostable DNA polymerase in other recombinant techniques such as DNA sequencing, nick-translation, and even reverse transcription.

SEQUENCE LISTING

The present application is being filed along with a Sequence Listing in electronic format. The Sequence Listing is provided as a file entitled IP1289.TXT, created Nov. 13, 2015, which is 466 Kb in size. The information in the electronic format of the Sequence Listing is incorporated herein by reference in its entirety.

BRIEF SUMMARY

Presented herein are methods and compositions for thermostable DNA polymerases that may be used to improve the PCR process and to improve the results obtained when using a thermostable DNA polymerase in other recombinant techniques such as DNA sequencing, nick-translation, and even reverse transcription.

Accordingly, one embodiment presented herein is a recombinant DNA polymerase comprising the amino acid sequence of any one of SEQ ID NOs: 1-66.

Also presented herein is a recombinant DNA polymerase comprising an amino acid sequence that is at least 60%, 70%, 80%, 85%, 90%, 95%, 99% identical to any one of SEQ ID NOs: 1-66, and which recombinant DNA polymerase exhibits polymerase activity.

Also presented herein is a fusion protein comprising a recombinant DNA polymerase as defined in any the above embodiments fused to an additional polypeptide. In some embodiments, the polypeptide domain fused to the polymerase can comprise a purification tag, an expression tag, a solubility tag, or a combination thereof. In some embodiments, the polypeptide domain fused to the polymerase can comprise, for example, Maltose Binding Protein (MBP). In some embodiments, the polypeptide domain fused to the polymerase can comprise, for example, a leader peptide having the amino acid sequence of SEQ ID NO: 72.

Also presented herein is a nucleic acid molecule encoding a recombinant polymerase as defined in any the above embodiments. Also presented herein is an expression vector comprising the nucleic acid molecule described above. Also presented herein is a host cell comprising the vector described above.

Also presented herein is a method for incorporating nucleotides into DNA comprising allowing the following components to interact: (i) a polymerase according to any the above embodiments, (ii) a DNA template; and (iii) a nucleotide solution.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 1 is a graph showing polymerase fidelity and performance, compared to Vent polymerase.

DETAILED DESCRIPTION

Presented herein are thermostable DNA polymerases that may be used to improve the PCR process and to improve the results obtained when using a thermostable DNA polymerase in other recombinant techniques such as DNA sequencing, nick-translation, and even reverse transcription. The present inventors have surprisingly identified certain thermostable polymerases which exhibit improved properties. The amino acid sequence of each of the thermostable polymerases is set forth in SEQ ID NOs: 1-66.

Accordingly, one embodiment presented herein is a recombinant DNA polymerase comprising the amino acid sequence of any one of SEQ ID NOs: 1-66.

Also presented herein is a recombinant DNA polymerase comprising an amino acid sequence that is at least 60%, 70%, 80%, 85%, 90%, 95%, 99% identical to any one of SEQ ID NOs: 1-66, and which recombinant DNA polymerase exhibits polymerase activity. It will be appreciated by one of skill in the art that one or more residues in a polymerase may be modified by substitution, deletion, or addition, while preserving polymerase activity. As such, any one of the polymerase sequences set forth as SEQ ID NOs: 1-66 may be modified by addition, deletion, or substitution of one or more residues and still retain polymerase activity. Polymerase activity of thermostable polymerase enzymes may be measured according to any one of a number of methodologies known in the art, as exemplified by the disclosures of U.S. Pat. Nos. 5,614,365; 7,598,032; 7,312,059; 6,395,524; 5,455,170; 5,405,774; 5,795,762; each of which is incorporated by reference in its entirety.

In some embodiments, the polymerase activity of one or more of the polymerases exhibits high performance in amplification conditions, such as those used for PCR. As used herein, performance can refer to affinity for primed template and/or high extension rate, also called processivity. As used herein, the term "high processivity" refers to a processivity higher than 20 nts (e.g., higher than 40 nts, 60 nts, 80 nts, 100 nts, 120 nts, 140 nts, 160 nts, 180 nts, 200 nts, 220 nts, 240 nts, 260 nts, 280 nts, 300 nts, 320 nts, 340 nts, 360 nts, 380 nts, 400 nts, or higher) per association/ disassociation with the template. Processivity can be measured, for example, according the methods in WO 01/92501A1, which is incorporated by reference in its entirety.

Performance under PCR conditions can be measured according to the methods described in Elshawadfy et al. (2014) Front. Microbio. 5:224, or those described in Arezi et al. (2014) Front. Microbio. 5:408, each of which is incorporated by reference in its entirety. Briefly, as described by Elshawadfy et al, qPCR can be performed using a Rotor-Gene 6000 thermocycler (Corbett Research, Qiagen). Genomic DNA from *S. cerevesiae* can be used as the template, with the DNA Pol 2 gene targeted for amplification. A common forward primer and one or more reverse primers can be used used to amplify lengths ranging from 145, to 1040 base pairs. Reactions are carried out in 25 µL containing 30 ng *S. cerevesiae* genomic DNA (Novagen), 1 µM of each primer, 400 µM of each dNTP, and 2.5 µl of SYBR green (10,000× stock in dimethlysulfoxide, Invitrogen; initially diluted 1000-fold with water). The reactions are initiated by adding the polymerase (final concentration 20 nM) in the same buffer used for primer-template extensions. The PCR consists of 1×95° C. for 2 min followed by 40 cycles of: 95° C. (10 s)/58° C. (20 s)/72° C. (the time used for the 72° C. extension step is variable). On completion of the PCR a melt curve analysis, consisting of a 90 s pre-melt step at 67° C. followed by a temperature increase to 95° C. at 0.2° C. per second, is carried out. 20 µl of the real time PCR mixtures are run on a 1% agarose gel (detection with ethidium bromide) in order to verify that amplification resulted in a product of the correct size.

In some embodiments, performance can be measured using PCR under high and low salt concentrations. For example, performance in salt can be tested as exemplified by the disclosure of, which is incorporated by reference in its entirety.

In some embodiments, the polymerase activity of one or more of the polymerases exhibits high fidelity. As described in U.S. Pat. No. 8,481,685, and as used herein, the term "fidelity" refers to the accuracy of DNA polymerization by template-dependent DNA polymerase. The fidelity of a DNA polymerase is typically measured by the error rate (the frequency of incorporating an inaccurate nucleotide, i.e., a nucleotide that is not incorporated at a template-dependent manner). The accuracy or fidelity of DNA polymerization is maintained by both the polymerase activity and the 3'-5' exonuclease activity of a DNA polymerase. The term "high fidelity" refers to an error rate less than $4.45 \times 10^{-6}$ (e.g., less than $4.0 \times 10^{-6}$, $3.5 \times 10^{-6}$, $3.0 \times 10^{-6}$, $2.5 \times 10^{-6}$, $2.0 \times 10^{-6}$, $1.5 \times 10^{-6}$, $1.0 \times 10^{-6}$, $0.5 \times 10^{-6}$) mutations/nt/doubling. The fidelity or error rate of a DNA polymerase may be measured using assays known to the art. For example, the error rates of DNA polymerases can be tested using the lad PCR fidelity assay described in Cline, J. et al. (96) NAR 24: 3546-3551. Briefly, a 1.9 kb fragment encoding the lacIOlacZa target gene is amplified from pPRIAZ plasmid DNA using 2.5 U DNA polymerase (i.e. amount of enzyme necessary to incorporate 25 nmoles of total dNTPs in 30 min at 72° C.) in the appropriate PCR buffer. The lad-containing PCR products are then cloned into lambda GT10 arms, and the percentage of lad mutants (MF, mutation frequency) is determined in a color screening assay, as described (Lundberg, K. S., Shoemaker, D. D., Adams, M. W. W., Short, J. M., Sorge, J. A., and Mathur, E. J. (1991) Gene 180: 1-8). Error rates are expressed as mutation frequency per bp per duplication (MF/bp/d), where bp is the number of detectable sites in the lad gene sequence (349) and d is the number of effective target doublings. Similar to the above, any plasmid containing the lacIOlacZa target gene can be used as template for the PCR. The PCR product may be cloned into a vector different from lambda GT (e.g., plasmid) that allows for blue/white color screening.

A variety of polymerase fidelity assays have been described in the literature over the years, perhaps the most famous being that of Thomas Kunkel (Kunkel, T. A. and Tindall, K. R. (1988) Biochemistry, 27, 6008-6013). The Kunkel method uses portions of the lacZαgene in M13 bacteriophage to correlate host bacterial colony color changes with errors in DNA synthesis. Wayne Barnes built upon this assay and utilized PCR to copy the entire lacZ gene and portions of two drug resistance genes with subsequent ligation, cloning, transformation and blue/white colony color determination (Barnes, W. M. (1992) Gene, 112, 29-35). In both assays, errors incorporated in the lacZ gene cause a disruption in β-galactosidase activity leading to a white colony phenotype. With these lacZ-based experimental approaches, the percentage of white colonies must be converted to the number of errors per base incorporated. As a more direct read-out of fidelity, Sanger sequencing of individual cloned PCR products can also score DNA polymerase fidelity and offers the advantage that all mutations will be detected. Using this method, the entire mutational spectrum of a polymerase can be determined and there is no need to correct for nonphenotypic changes. Other methods of measuring fidelity can directly monitor misincorporation of bases. For example, using high-throughput sequencing systems, fidelity can also be measured by measuring errors accumulated during amplification by reading the sequence of amplicons and comparing to the template sequence.

The properties of the one or more polymerases presented herein can be compared to one or more other enzymes, which are known in the art. For example, in some embodiments, the fidelity of the polymerase can be compared to that of a known polymerase, such as a thermostable polymerase. In some embodiments, the processivity of the polymerase can be compared to that of a known polymerase, such as a thermostable polymerase. In some embodiments, the polymerase exhibits increased fidelity compared to a known polymerase. In some embodiments, the polymerase exhibits increased processivity compared to a known polymerase. In some embodiments, the polymerase exhibits increased fidelity and processivity compared to a known polymerase. In some embodiments, the polymerase exhibits increased fidelity but lower processivity compared to a known polymerase. In some embodiments, the polymerase exhibits increased processivity but lower fidelity compared to a known polymerase. Known DNA polymerases include, for example, *Pyrococcus furiosus* (Pfu) DNA polymerase (Lundberg et al., 1991, Gene, 108: 1), *E. coli* DNA polymerase I (Lecomte and Doubleday, 1983, Nucleic Acids Res. 11:7505), T7 DNA polymerase (Nordstrom et al., 1981, J. Biol. Chem. 256:3112), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent DNA polymerase, Cariello et al., 1991, Nucleic Acids Res, 19: 4193), 9° Nm DNA polymerase (discontinued product from New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), *Thermococcus kodakaraensis* KOD DNA polymerase (Takagi et al., 1997, Appl. Environ. Microbiol. 63:4504), JDF-3 DNA polymerase (Patent application WO 0132887), and *Pyrococcus* GB-D (PGB-D) DNA polymerase (Juncosa-Ginesta et al., 1994, Biotechniques, 16:820).

In some embodiments, the polymerase exhibits increased fidelity and/or processivity compared to a *Thermococcus litoralis* (Tli) DNA polymerase (also referred to as Vent DNA polymerase, Cariello et al., 1991, Nucleic Acids Res, 19: 4193). Vent DNA polymerase is available commercially and can be used in the activity assays described herein as a baseline measure of polymerase activity, such as fidelity and/or processivity. In some embodiments, the polymerase exhibits increased processivity compared to Vent DNA polymerase. In some embodiments, the polymerase exhibits increased fidelity and processivity compared to Vent DNA polymerase. In some embodiments, the polymerase exhibits increased fidelity but lower processivity compared to Vent DNA polymerase. In some embodiments, the polymerase exhibits increased processivity but lower fidelity compared to Vent DNA polymerase.

Making and Isolating Recombinant Polymerases

Generally, nucleic acids encoding a polymerase as presented herein can be made by cloning, recombination, in vitro synthesis, in vitro amplification and/or other available methods. A variety of recombinant methods can be used for expressing an expression vector that encodes a polymerase as presented herein. Methods for making recombinant nucleic acids, expression and isolation of expressed products are well known and described in the art. A number of exemplary mutations and combinations of mutations, as well as strategies for design of desirable mutations, are described herein. Methods for making and selecting mutations in the active site of polymerases, including for modifying steric features in or near the active site to permit improved access by nucleotide analogs are found hereinabove and, e.g., in WO 2007/076057 and PCT/US2007/022459, which are incorporated by reference in their entireties.

Additional useful references for mutation, recombinant and in vitro nucleic acid manipulation methods (including cloning, expression, PCR, and the like) include Berger and Kimmel, Guide to Molecular Cloning Techniques, Methods in Enzymology volume 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); and The Nucleic Acid Protocols Handbook Ralph Rapley (ed) (2000) Cold Spring Harbor, Humana Press Inc (Rapley); Chen et al. (ed) PCR Cloning Protocols, Second Edition (Methods in Molecular Biology, volume 192) Humana Press; and in Viljoen et al. (2005) Molecular Diagnostic PCR Handbook Springer, ISBN 1402034032.

In addition, a plethora of kits are commercially available for the purification of plasmids or other relevant nucleic acids from cells, (see, e.g., EasyPrep™, FlexiPrep™ both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

Other useful references, e.g. for cell isolation and culture (e.g., for subsequent nucleic acid isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York) and Atlas and Parks (eds) The Handbook of Microbiological Media (1993) CRC Press, Boca Raton, Fla.

Nucleic acids encoding the recombinant polymerases disclosed herein are also a feature of embodiments presented herein. A particular amino acid can be encoded by multiple codons, and certain translation systems (e.g., prokaryotic or eukaryotic cells) often exhibit codon bias, e.g., different organisms often prefer one of the several synonymous codons that encode the same amino acid. As such, nucleic acids presented herein are optionally "codon optimized," meaning that the nucleic acids are synthesized to include codons that are preferred by the particular translation system being employed to express the polymerase. For example, when it is desirable to express the polymerase in a bacterial cell (or even a particular strain of bacteria), the nucleic acid can be synthesized to include codons most frequently found in the genome of that bacterial cell, for efficient expression of the polymerase. A similar strategy can be employed when it is desirable to express the polymerase in a eukaryotic cell, e.g., the nucleic acid can include codons preferred by that eukaryotic cell.

In some embodiments, one or more polypeptide domains can be fused to the polymerase. In some embodiments, the domain is fused to the C-terminus of the polymerase. In some embodiments, the domain is fused to the N-terminus of the polymerase. In some embodiments, the domain is internal to the polymerase sequence. In some embodiments, the polypeptide domain comprises a purification tag. The term "purification tag" as used herein refers to any peptide sequence suitable for purification or identification of a polypeptide. The purification tag specifically binds to another moiety with affinity for the purification tag. Such moieties which specifically bind to a purification tag are usually attached to a matrix or a resin, such as agarose beads. Moieties which specifically bind to purification tags include antibodies, other proteins (e.g. Protein A or Streptavidin), nickel or cobalt ions or resins, biotin, amylose, maltose, and cyclodextrin. Exemplary purification tags include histidine (HIS) tags (such as a hexahistidine peptide), which will bind to metal ions such as nickel or cobalt ions. Other exemplary purification tags are the myc tag (EQKLISEEDL), the Strep tag (WSHPQFEK), the Flag tag (DYKDDDDK) and the V5 tag (GKPIPNPLLGLDST). The term "purification tag" also includes "epitope tags", i.e. peptide sequences which are specifically recognized by antibodies. Exemplary epitope tags include the FLAG tag, which is specifically recognized by a monoclonal anti-FLAG antibody. The peptide sequence recognized by the anti-FLAG antibody consists of the sequence DYKDDDDK or a substantially identical variant thereof. In some embodiments, the polypeptide domain fused to the polymerase comprises two or more tags, such as a SUMO tag and a STREP tag. The term "purification tag" also includes substantially identical variants of purification tags. "Substantially identical variant" as used herein refers to derivatives or fragments of purification tags which are modified compared to the original purification tag (e.g. via amino acid substitutions, deletions or insertions), but which retain the property of the purification tag of specifically binding to a moiety which specifically recognizes the purification tag.

In some embodiments, the polypeptide domain fused to the polymerase comprises an expression tag. The term "expression tag" as used herein refers to any peptide or polypeptide that can be attached to a second polypeptide and is supposed to support the solubility, stability and/or the expression of a recombinant polypeptide of interest. Exemplary expression tags include Fc-tag and SUMO-tag. In principle, any peptide, polypeptide or protein can be used as an expression tag.

In some embodiments, the polypeptide domain fused to the polymerase comprises the leader peptide set forth in SEQ ID NO: 72.

A variety of protein isolation and detection methods are known and can be used to isolate polymerases, e.g., from recombinant cultures of cells expressing the recombinant polymerases presented herein. A variety of protein isolation and detection methods are well known in the art, including, e.g., those set forth in R. Scopes, Protein Purification, Springer-Verlag, N.Y. (1982); Deutscher, Methods in Enzymology Vol. 182: Guide to Protein Purification, Academic Press, Inc. N.Y. (1990); Sandana (1997) Bioseparation of Proteins, Academic Press, Inc.; Bollag et al. (1996) Protein Methods, 2.sup.nd Edition Wiley-Liss, NY; Walker (1996) The Protein Protocols Handbook Humana Press, NJ, Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3.sup.rd Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ; and the references cited therein. Additional details regarding protein purification and detection methods can be found in Satinder Ahuja ed., Handbook of Bioseparations, Academic Press (2000).

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a polymerase, or the amino acid sequence of a polymerase) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Current Protocols in Molecular Biology, Ausubel et al., eds., Current Protocols, a joint venture between Greene Publishing Associates, Inc. and John Wiley & Sons, Inc., supplemented through 2004).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Nucleic Acids Encoding Altered Polymerases

Further presented herein are nucleic acid molecules encoding the altered polymerase enzymes presented herein. For any given altered polymerase which is a mutant version of a polymerase for which the amino acid sequence and preferably also the wild type nucleotide sequence encoding the polymerase is known, it is possible to obtain a nucleotide sequence encoding the mutant according to the basic principles of molecular biology. For example, given that the wild type nucleotide sequence encoding a polymerase is known, it is possible to deduce a nucleotide sequence encoding any given mutant version of the polymerase having one or more amino acid substitutions using the standard genetic code. Similarly, nucleotide sequences can readily be derived for mutant versions other polymerases such as, for example, Vent™, Pfu, T. sp. JDF-3, Taq, etc. Nucleic acid molecules having the required nucleotide sequence may then be constructed using standard molecular biology techniques known in the art.

In accordance with the embodiments presented herein, a defined nucleic acid includes not only the identical nucleic acid but also any minor base variations including, in particular, substitutions in cases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The nucleic acid molecules described herein may also, advantageously, be included in a suitable expression vector to express the polymerase proteins encoded therefrom in a suitable host. Incorporation of cloned DNA into a suitable expression vector for subsequent transformation of said cell and subsequent selection of the transformed cells is well known to those skilled in the art as provided in Sambrook et al. (1989), Molecular cloning: A Laboratory Manual, Cold Spring Harbor Laboratory, which is incorporated by reference in its entirety.

Such an expression vector includes a vector having a nucleic acid according to the embodiments presented herein operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for the expression of a protein according to the embodiments presented herein.

The nucleic acid molecule may encode a mature protein or a protein having a prosequence, including that encoding a leader sequence on the preprotein which is then cleaved by the host cell to form a mature protein. The vectors may be, for example, plasmid, virus or phage vectors provided with an origin of replication, and optionally a promoter for the expression of said nucleotide and optionally a regulator of the promoter. The vectors may contain one or more selectable markers, such as, for example, an antibiotic resistance gene.

Regulatory elements required for expression include promoter sequences to bind RNA polymerase and to direct an appropriate level of transcription initiation and also translation initiation sequences for ribosome binding. For example, a bacterial expression vector may include a promoter such as the lac promoter and for translation initiation the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or be assembled from the sequences described by methods well known in the art.

Transcription of DNA encoding the polymerase by higher eukaryotes may be optimised by including an enhancer sequence in the vector. Enhancers are cis-acting elements of DNA that act on a promoter to increase the level of transcription. Vectors will also generally include origins of replication in addition to the selectable markers.

EXAMPLES

Example 1

Expression and Purification

Commercially available expression vectors (pD871) are obtained from DNA2.0 (Menlo Park, Calif.) for 5 synthetic parent sequences encoding amino acid sequences of SEQ ID Nos: 67-71. For expression of genes in other vectors, the genes are re-cloned into pD861 expression vectors (DNA2.0, Menlo Park, Calif.). 66 different expression vectors are then generated by combining portions of the parent vectors in various combinations to produce expression vectors encoding polymerase amino acid sequences of SEQ ID Nos: 1-66. The encoded enzymes also contain a leader peptide comprising the following sequence: MGSSHGHH-HHHHHGVGGWSHPQ FEKGGTENLYFQGGH (SEQ ID NO: 72), which is used for purification.

Each of the expression plasmids is transformed into competent expression strain (Edge BioSystems, Gaithersburg, Md.) and the transformants are cultured overnight and then diluted to a larger volume. Upon reaching induction density, expression is induced by addition of Rhamnose and allowed to continue to incubate for an additional time period. The induced cells are then harvested by centrifugation, followed by freezing at −20° C. The cells are incubated at 100° C. to lyse the cells.

Cell lysates are then passed over spin columns containing Ni-NTA and heparin affinity resins to purify the expressed polymerases.

Example 2

Expression vectors encoding 33 of the polymerase amino acid sequences of SEQ ID Nos: 1-66 were prepared according to the methods described in Example 1. The encoded enzymes also contained a leader peptide comprising the following sequence: MGSSHGHHHHHHGVGGWSH-PQFEKGGTENLYFQGGH (SEQ ID NO: 72), which was used for purification. The enzymes were expressed and purified as set forth above in Example 1, and then were tested for polymerase activity and fidelity as set forth in the examples below.

Example 3

Polymerase Fidelity Activity 28 of the polymerase enzymes expressed in Example 2 were tested for fidelity. All fidelity levels were compared to that of Vent DNA polymerase, which was used as a baseline. As set forth in FIG. 1, all but 10 of the enzymes tested had fidelity levels that meet or exceed that of Vent.

Example 4

Polymerase qPCR Activity 28 of the polymerase enzymes expressed in Example 2 were tested for robustness and speed using a qPCR assay. All activity levels were compared to that of Vent DNA polymerase, which was used as a baseline. As set forth in FIG. 1, at least 8 of the enzymes had activity levels that are near or in excess of that of Vent. The experiments were performed to test polymerases under a variety of conditions and extension times.

For qPCR data analysis, the polymerase rankings were derived from a combination of the metrics below.

1) Amplification max
2) # of cycles to 50% amp max
3) Melt peak max temperature
4) Melt peak max intensity The polymerase rankings were compared to that of Vent polymerase, as set forth in FIG. 1.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A recombinant DNA polymerase comprising the amino acid sequence of SEQ ID NO: 14.

2. A recombinant DNA polymerase comprising an amino acid sequence that is at least 95% identical to SEQ ID NO:14, and which recombinant DNA polymerase exhibits polymerase activity.

3. The recombinant DNA polymerase according to claim 1, wherein the polymerase further comprises an N-terminal leader peptide.

4. The recombinant DNA polymerase according to claim 3, wherein the leader peptide comprises a His tag.

5. The recombinant DNA polymerase according to claim 4, wherein the leader peptide comprises the amino acid sequence of SEQ ID NO: 72.

6. A method for incorporating nucleotides into DNA comprising allowing the following components to interact: (i) a polymerase according to claim 1, (ii) a DNA template; and (iii) a nucleotide solution.

7. The recombinant DNA polymerase according to claim 2, wherein the polymerase exhibits increased fidelity compared to *Thermococcus litoralis* (Tli) DNA polymerase.

8. The recombinant DNA polymerase according to claim 2, wherein the polymerase exhibits increased activity compared to *Thermococcus litoralis* (Tli) DNA polymerase.

9. The recombinant DNA polymerase according to claim 2, wherein the polymerase exhibits increased activity and increased fidelity compared to *Thermococcus litoralis* (Tli) DNA polymerase.

10. The recombinant DNA polymerase according to claim 2, wherein the polymerase exhibits increased activity and lower fidelity compared to *Thermococcus litoralis* (Tli) DNA polymerase.

11. The recombinant DNA polymerase according to claim 2, wherein the polymerase exhibits increased fidelity and lower activity compared to *Thermococcus litoralis* (Tli) DNA polymerase.

12. The recombinant DNA polymerase of claim 2 comprising the amino acid sequence of SEQ ID NO: 29.

13. The recombinant DNA polymerase according to claim 2, wherein the polymerase further comprises an N-terminal leader peptide.

14. The recombinant DNA polymerase according to claim 13, wherein the leader peptide comprises a His tag.

15. The recombinant DNA polymerase according to claim 14, wherein the leader peptide comprises the amino acid sequence of SEQ ID NO: 72.

16. The recombinant DNA polymerase of claim 2, wherein the recombinant DNA polymerase comprises an amino acid sequence that is at least 99% identical to SEQ ID NO: 14.

17. A method for incorporating nucleotides into DNA comprising allowing the following components to interact: (i) a polymerase according to claim 2, (ii) a DNA template; and (iii) a nucleotide solution.

18. The recombinant DNA polymerase of claim 2 comprising the amino acid sequence of SEQ ID NO: 12.

19. The recombinant DNA polymerase of claim 2 comprising the amino acid sequence of SEQ ID NO: 13.

* * * * *

SEQUENCE LISTING

```
<160> NUMBER OF SEQ ID NOS: 72

<210> SEQ ID NO 1
<211> LENGTH: 775
<212> TYPE: PRT
<213> ORGANISM: Artificial sequence
<220> FEATURE:
<223> OTHER INFORMATION: Chimeric sequence

<400> SEQUENCE: 1

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175
```

-continued

```
Asp Leu Pro Tyr Val Glu Val Ser Ser Arg Glu Met Ile Lys
            180                 185             190

Arg Phe Leu Lys Val Ile Arg Glu Lys Asp Pro Asp Val Ile Ile Thr
            195                 200             205

Tyr Asn Gly Asp Ser Phe Asp Leu Pro Tyr Leu Val Lys Arg Ala Glu
            210                 215             220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
            245                 250             255

His Phe Asp Leu Tyr His Val Ile Arg Arg Thr Ile Asn Leu Pro Thr
            260                 265             270

Tyr Thr Leu Glu Ala Val Tyr Glu Ala Ile Phe Gly Lys Pro Lys Glu
            275                 280             285

Lys Val Tyr Ala His Glu Ile Ala Glu Ala Trp Glu Thr Gly Lys Gly
            290                 295             300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
            325                 330             335

Val Gly Gln Pro Val Trp Asp Val Ser Arg Ser Thr Gly Asn Leu
            340                 345             350

Val Glu Trp Phe Leu Leu Arg Lys Ala Tyr Glu Arg Asn Glu Leu Ala
            355                 360             365

Pro Asn Lys Pro Asp Glu Arg Glu Tyr Glu Arg Arg Leu Arg Glu Ser
            370                 375             380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
            405                 410             415

His Asn Val Ser Pro Asp Thr Leu Asn Arg Glu Asn Cys Lys Glu Tyr
            420                 425             430

Asp Val Ala Pro Gln Val Gly His Arg Phe Cys Lys Asp Phe Pro Gly
            435                 440             445

Phe Ile Pro Ser Leu Leu Gly Asn Leu Leu Glu Glu Arg Gln Lys Ile
450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
            485                 490             495

Tyr Tyr Gly Tyr Ala Lys Ala Arg Trp Tyr Cys Lys Glu Cys Ala Glu
            500                 505             510

Ser Val Thr Ala Trp Gly Arg Gln Tyr Ile Asp Leu Val Arg Arg Glu
            515                 520             525

Leu Glu Ser Arg Gly Phe Lys Val Leu Tyr Ile Asp Thr Asp Gly Leu
            530                 535             540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
            565                 570             575

Leu Glu Tyr Glu Gly Phe Tyr Arg Gly Phe Phe Val Thr Lys Lys
            580                 585             590
```

-continued

```
Lys Tyr Ala Val Ile Asp Glu Glu Asp Lys Ile Thr Thr Arg Gly Leu
            595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg Tyr Glu Val Pro
                645                 650                 655

Pro Glu Lys Leu Val Ile Tyr Glu Gln Ile Thr Arg Asn Leu Arg Asp
            660                 665                 670

Tyr Arg Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
690                 695                 700

Lys Gly Pro Gly Arg Val Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Ala Gly Leu Gly Ala Trp
        755                 760                 765

Leu Lys Pro Lys Thr Gly Ser
770                 775

<210> SEQ ID NO 2
<211> LENGTH: 774
<212> TYPE: PRT
<213> ORGANISM: Artificial sequence
<220> FEATURE:
<223> OTHER INFORMATION: Chimeric sequence

<400> SEQUENCE: 2

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175
```

```
Asp Leu Pro Tyr Val Glu Val Val Ser Ser Arg Glu Met Ile Lys
            180                 185                 190
Arg Phe Leu Lys Val Ile Arg Glu Lys Asp Pro Asp Val Ile Ile Thr
        195                 200                 205
Tyr Asn Gly Asp Ser Phe Asp Leu Pro Tyr Leu Val Lys Arg Ala Glu
    210                 215                 220
Lys Leu Gly Ile Lys Leu Pro Leu Gly Arg Asp Gly Ser Glu Pro Lys
225                 230                 235                 240
Met Gln Arg Leu Gly Asp Met Thr Ala Val Glu Ile Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala His Glu Ile Ala Glu Ala Trp Glu Thr Gly Lys Gly
    290                 295                 300
Leu Glu Arg Val Ala Lys Tyr Ser Met Glu Asp Ala Lys Val Thr Phe
305                 310                 315                 320
Glu Leu Gly Lys Glu Phe Phe Pro Met Glu Ala Gln Leu Ala Arg Leu
                325                 330                 335
Val Gly Gln Pro Val Trp Asp Val Ser Arg Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Arg Glu Tyr Glu Arg Arg Leu Arg Glu Ser
    370                 375                 380
Tyr Glu Gly Gly Tyr Val Lys Glu Pro Glu Lys Gly Leu Trp Glu Gly
385                 390                 395                 400
Ile Val Ser Leu Asp Phe Arg Ser Leu Tyr Pro Ser Ile Ile Ile Thr
                405                 410                 415
His Asn Val Ser Pro Asp Thr Leu Asn Arg Glu Asn Cys Lys Glu Tyr
            420                 425                 430
Asp Val Ala Pro Gln Val Gly His Arg Phe Cys Lys Asp Phe Pro Gly
        435                 440                 445
Phe Ile Pro Ser Leu Leu Gly Asn Leu Leu Glu Glu Arg Gln Lys Ile
    450                 455                 460
Lys Lys Arg Met Lys Glu Ser Lys Asp Pro Val Glu Lys Lys Leu Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Gln Tyr Ile Asp Leu Val Arg Arg Glu
        515                 520                 525
Leu Glu Ser Arg Gly Phe Lys Val Leu Tyr Ile Asp Thr Asp Gly Leu
    530                 535                 540
Tyr Ala Thr Ile Pro Gly Ala Lys His Glu Glu Ile Lys Glu Lys Ala
545                 550                 555                 560
Leu Lys Phe Val Glu Tyr Ile Asn Ser Lys Leu Pro Gly Leu Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Gly Lys Ile Thr Thr Arg Gly Leu
```

```
                595                 600                 605
Glu Ile Arg Arg Asp Trp Ser Glu Ile Ala Lys Glu Thr Gln Ala
        610                 615                 620
Arg Val Leu Glu Ala Leu Leu Lys Asp Gly Asp Val Glu Lys Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Lys Asp
            660                 665                 670
Tyr Lys Ala Thr Gly Pro His Val Ala Val Lys Arg Leu Ala Ala
        675                 680                 685
Arg Gly Val Lys Ile Arg Pro Gly Thr Val Ile Ser Tyr Ile Val Leu
690                 695                 700
Lys Gly Ser Gly Arg Ile Gly Asp Arg Ala Ile Pro Phe Asp Glu Phe
705                 710                 715                 720
Asp Pro Thr Lys His Lys Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
            740                 745                 750
Glu Asp Leu Arg Tyr Gln Lys Thr Arg Gln Val Gly Leu Ser Ala Trp
        755                 760                 765
Leu Lys Pro Lys Gly Thr
    770

<210> SEQ ID NO 3
<211> LENGTH: 774
<212> TYPE: PRT
<213> ORGANISM: Artificial sequence
<220> FEATURE:
<223> OTHER INFORMATION: Chimeric sequence

<400> SEQUENCE: 3

Met Ile Leu Asp Ala Asp Tyr Ile Thr Glu Asp Gly Lys Pro Ile Ile
1               5                   10                  15
Arg Ile Phe Lys Lys Glu Asn Gly Glu Phe Lys Val Glu Tyr Asp Arg
            20                  25                  30
Asn Phe Arg Pro Tyr Ile Tyr Ala Leu Leu Lys Asp Asp Ser Gln Ile
        35                  40                  45
Asp Glu Val Arg Lys Ile Thr Ala Glu Arg His Gly Lys Ile Val Arg
    50                  55                  60
Ile Ile Asp Ala Glu Lys Val Arg Lys Phe Leu Gly Arg Pro Ile
65                  70                  75                  80
Glu Val Trp Arg Leu Tyr Phe Glu His Pro Gln Asp Val Pro Ala Ile
                85                  90                  95
Arg Asp Lys Ile Arg Glu His Ser Ala Val Ile Asp Ile Phe Glu Tyr
            100                 105                 110
Asp Ile Pro Phe Ala Lys Arg Tyr Leu Ile Asp Lys Gly Leu Ile Pro
        115                 120                 125
Met Glu Gly Asp Glu Glu Leu Lys Leu Leu Ala Phe Asp Ile Glu Thr
    130                 135                 140
Leu Tyr His Glu Gly Glu Glu Phe Ala Lys Gly Pro Ile Ile Met Ile
145                 150                 155                 160
Ser Tyr Ala Asp Glu Glu Glu Ala Lys Val Ile Thr Trp Lys Lys Ile
                165                 170                 175
Asp Leu Pro Tyr Val Glu Val Val Ser Ser Glu Arg Glu Met Ile Lys
```

-continued

```
            180                 185                 190
Arg Phe Leu Lys Val Ile Arg Glu Lys Asp Pro Asp Val Ile Ile Thr
            195                 200                 205
Tyr Asn Gly Asp Ser Phe Asp Leu Pro Tyr Leu Val Lys Arg Ala Glu
            210                 215                 220
Lys Leu Gly Ile Lys Leu Pro Leu Gly Arg Asp Gly Ser Glu Pro Lys
225                 230                 235                 240
Met Gln Arg Leu Gly Asp Met Thr Ala Val Glu Ile Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
            275                 280                 285
Lys Val Tyr Ala His Glu Ile Ala Glu Ala Trp Glu Thr Gly Lys Gly
            290                 295                 300
Leu Glu Arg Val Ala Lys Tyr Ser Met Glu Asp Ala Lys Val Thr Phe
305                 310                 315                 320
Glu Leu Gly Lys Glu Phe Phe Pro Met Glu Ala Gln Leu Ala Arg Leu
                325                 330                 335
Val Gly Gln Pro Val Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
            355                 360                 365
Pro Asn Lys Pro Asp Glu Arg Glu Tyr Glu Arg Arg Leu Arg Glu Ser
            370                 375                 380
Tyr Glu Gly Gly Tyr Val Lys Glu Pro Glu Lys Gly Leu Trp Glu Gly
385                 390                 395                 400
Ile Val Ser Leu Asp Phe Arg Ser Leu Tyr Pro Ser Ile Ile Ile Thr
                405                 410                 415
His Asn Val Ser Pro Asp Thr Leu Asn Arg Glu Asn Cys Lys Glu Tyr
            420                 425                 430
Asp Val Ala Pro Gln Val Gly His Arg Phe Cys Lys Asp Phe Pro Gly
            435                 440                 445
Phe Ile Pro Ser Leu Leu Gly Asn Leu Leu Glu Glu Arg Gln Lys Ile
            450                 455                 460
Lys Lys Arg Met Lys Glu Ser Lys Asp Pro Val Glu Lys Lys Leu Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Gln Tyr Ile Asp Leu Val Arg Arg Glu
            515                 520                 525
Leu Glu Ser Arg Gly Phe Lys Val Leu Tyr Ile Asp Thr Asp Gly Leu
            530                 535                 540
Tyr Ala Thr Ile Pro Gly Ala Lys His Glu Glu Ile Lys Glu Lys Ala
545                 550                 555                 560
Leu Lys Phe Val Glu Tyr Ile Asn Ser Lys Leu Pro Gly Leu Leu Glu
                565                 570                 575
Leu Glu Tyr Glu Gly Phe Tyr Lys Arg Gly Phe Phe Val Thr Lys Lys
            580                 585                 590
Arg Tyr Ala Val Ile Asp Glu Glu Gly Lys Val Ile Thr Arg Gly Leu
            595                 600                 605
```

-continued

```
Glu Ile Val Arg Arg Asp Trp Ser Glu Ile Ala Lys Glu Thr Gln Ala
    610                 615                 620
Arg Val Leu Glu Thr Ile Leu Lys His Gly Asp Val Glu Ala Val
625                 630                 635                 640
Arg Ile Val Lys Glu Val Ile Gln Lys Leu Ala Asn Tyr Glu Ile Pro
                645                 650                 655
Pro Glu Lys Leu Ala Ile Tyr Glu Gln Ile Thr Arg Pro Leu His Glu
                660                 665                 670
Tyr Lys Ala Ile Gly Pro His Val Ala Val Lys Lys Leu Ala Ala
                675                 680                 685
Lys Gly Val Lys Ile Lys Pro Gly Met Val Ile Gly Tyr Ile Val Leu
    690                 695                 700
Arg Gly Asp Gly Pro Ile Ser Asn Arg Ala Ile Leu Ala Glu Glu Tyr
705                 710                 715                 720
Asp Pro Lys Lys His Lys Tyr Asp Ala Glu Tyr Tyr Ile Glu Asn Gln
                725                 730                 735
Val Leu Pro Ala Val Leu Arg Ile Leu Glu Gly Phe Gly Tyr Arg Lys
                740                 745                 750
Glu Asp Leu Arg Tyr Gln Lys Thr Arg Gln Val Gly Leu Thr Ser Trp
                755                 760                 765
Leu Asn Ile Lys Lys Ser
    770

<210> SEQ ID NO 4
<211> LENGTH: 773
<212> TYPE: PRT
<213> ORGANISM: Artificial sequence
<220> FEATURE:
<223> OTHER INFORMATION: Chimeric sequence

<400> SEQUENCE: 4

Met Ile Leu Asp Ala Asp Tyr Ile Thr Glu Asp Gly Lys Pro Ile Ile
1               5                   10                  15
Arg Ile Phe Lys Lys Glu Asn Gly Glu Phe Lys Val Glu Tyr Asp Arg
                20                  25                  30
Asn Phe Arg Pro Tyr Ile Tyr Ala Leu Leu Lys Asp Asp Ser Gln Ile
            35                  40                  45
Asp Glu Val Arg Lys Ile Thr Ala Glu Arg His Gly Lys Ile Val Arg
        50                  55                  60
Ile Ile Asp Ala Glu Lys Val Arg Lys Phe Leu Gly Arg Pro Ile
65                  70                  75                  80
Glu Val Trp Arg Leu Tyr Phe Glu His Pro Gln Asp Val Pro Ala Ile
                85                  90                  95
Arg Asp Lys Ile Arg Glu His Ser Ala Val Ile Asp Ile Phe Glu Tyr
                100                 105                 110
Asp Ile Pro Phe Ala Lys Arg Tyr Leu Ile Asp Lys Gly Leu Ile Pro
            115                 120                 125
Met Glu Gly Asp Glu Glu Leu Lys Leu Leu Ala Phe Asp Ile Glu Thr
        130                 135                 140
Leu Tyr His Glu Gly Glu Glu Phe Ala Lys Gly Pro Ile Ile Met Ile
145                 150                 155                 160
Ser Tyr Ala Asp Glu Glu Glu Ala Lys Val Ile Thr Trp Lys Lys Ile
                165                 170                 175
Asp Leu Pro Tyr Val Glu Val Val Ser Ser Glu Arg Glu Met Ile Lys
                180                 185                 190
```

```
Arg Phe Leu Lys Val Ile Arg Glu Lys Asp Pro Asp Val Ile Ile Thr
            195                 200                 205

Tyr Asn Gly Asp Ser Phe Asp Leu Pro Tyr Leu Val Lys Arg Ala Glu
        210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Ala Glu Ser Tyr
370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Arg Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
        515                 520                 525

Glu Glu Lys Phe Gly Phe Lys Val Leu Tyr Ala Asp Thr Asp Gly Phe
530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Ala Arg Gly Phe Phe Val Thr Lys Lys
            580                 585                 590

Lys Tyr Ala Leu Ile Asp Glu Glu Gly Lys Ile Val Thr Arg Gly Leu
        595                 600                 605
```

```
Glu Ile Val Arg Arg Asp Trp Ser Glu Ile Ala Lys Glu Thr Gln Ala
610                 615                 620
Lys Val Leu Glu Ala Ile Leu Lys His Gly Asn Val Asp Glu Ala Val
625                 630                 635                 640
Lys Ile Val Lys Glu Val Thr Glu Lys Leu Ser Lys Tyr Glu Ile Pro
            645                 650                 655
Pro Glu Lys Leu Val Ile Tyr Glu Gln Ile Thr Arg Pro Leu Ser Glu
        660                 665                 670
Tyr Lys Ala Ile Gly Pro His Val Ala Val Lys Arg Leu Ala Ala
    675                 680                 685
Lys Gly Val Lys Val Lys Pro Gly Met Val Ile Gly Tyr Ile Val Leu
690                 695                 700
Arg Gly Asp Gly Pro Ile Ser Lys Arg Ala Ile Ala Ile Glu Glu Phe
705                 710                 715                 720
Asp Pro Lys Lys His Lys Tyr Asp Ala Glu Tyr Tyr Ile Glu Asn Gln
            725                 730                 735
Val Leu Pro Ala Val Glu Arg Ile Leu Arg Ala Phe Gly Tyr Arg Lys
        740                 745                 750
Glu Asp Leu Lys Tyr Gln Lys Thr Lys Gln Val Gly Leu Gly Ala Trp
        755                 760                 765
Leu Lys Phe Gly Ser
770

<210> SEQ ID NO 5
<211> LENGTH: 775
<212> TYPE: PRT
<213> ORGANISM: Artificial sequence
<220> FEATURE:
<223> OTHER INFORMATION: Chimeric sequence

<400> SEQUENCE: 5

Met Ile Leu Asp Ala Asp Tyr Ile Thr Glu Asp Gly Lys Pro Ile Ile
1               5                   10                  15
Arg Ile Phe Lys Lys Glu Asn Gly Glu Phe Lys Val Glu Tyr Asp Arg
            20                  25                  30
Asn Phe Arg Pro Tyr Ile Tyr Ala Leu Leu Lys Asp Asp Ser Gln Ile
        35                  40                  45
Asp Glu Val Arg Lys Ile Thr Ala Glu Arg His Gly Lys Ile Val Arg
    50                  55                  60
Ile Ile Asp Ala Glu Lys Val Arg Lys Lys Phe Leu Gly Arg Pro Ile
65                  70                  75                  80
Glu Val Trp Arg Leu Tyr Phe Glu His Pro Gln Asp Val Pro Ala Ile
                85                  90                  95
Arg Asp Lys Ile Arg Glu His Ser Ala Val Ile Asp Ile Phe Glu Tyr
            100                 105                 110
Asp Ile Pro Phe Ala Lys Arg Tyr Leu Ile Asp Lys Gly Leu Ile Pro
        115                 120                 125
Met Glu Gly Asp Glu Glu Leu Lys Leu Leu Ala Phe Asp Ile Glu Thr
    130                 135                 140
Leu Tyr His Glu Gly Glu Glu Phe Ala Lys Gly Pro Ile Ile Met Ile
145                 150                 155                 160
Ser Tyr Ala Asp Glu Glu Glu Ala Lys Val Ile Thr Trp Lys Lys Ile
                165                 170                 175
Asp Leu Pro Tyr Val Glu Val Val Ser Ser Glu Arg Glu Met Ile Lys
            180                 185                 190
```

```
Arg Phe Leu Lys Val Ile Arg Glu Lys Asp Pro Asp Val Ile Ile Thr
            195                 200                 205
Tyr Asn Gly Asp Ser Phe Asp Leu Pro Tyr Leu Val Lys Arg Ala Glu
210                 215                 220
Lys Leu Gly Ile Lys Leu Pro Leu Gly Arg Asp Gly Ser Glu Pro Lys
225                 230                 235                 240
Met Gln Arg Leu Gly Asp Met Thr Ala Val Glu Ile Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala His Glu Ile Ala Glu Ala Trp Glu Thr Gly Lys Gly
290                 295                 300
Leu Glu Arg Val Ala Lys Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Ser Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Arg Glu Leu Ala Arg Arg Ala Glu Ser Tyr
    370                 375                 380
Ala Gly Gly Tyr Val Lys Glu Pro Glu Lys Gly Leu Trp Glu Asn Ile
385                 390                 395                 400
Val Tyr Leu Asp Tyr Lys Ser Leu Tyr Pro Ser Ile Ile Thr His
                405                 410                 415
Asn Val Ser Pro Asp Thr Leu Asn Arg Glu Gly Cys Arg Glu Tyr Asp
            420                 425                 430
Val Ala Pro Gln Val Gly His Arg Phe Cys Lys Asp Phe Pro Gly Phe
        435                 440                 445
Ile Pro Ser Leu Leu Gly Asp Leu Leu Glu Glu Arg Gln Lys Val Lys
    450                 455                 460
Lys Lys Met Lys Ala Thr Val Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Asn Ala Arg Trp Tyr Cys Arg Glu Cys Ala Glu Ser
            500                 505                 510
Val Thr Ala Trp Gly Arg Gln Tyr Ile Glu Thr Thr Met Arg Glu Ile
        515                 520                 525
Glu Glu Lys Phe Gly Phe Lys Val Leu Tyr Ala Asp Thr Asp Gly Phe
    530                 535                 540
Phe Ala Thr Ile Pro Gly Ala Asp Ala Glu Thr Val Lys Lys Lys Thr
545                 550                 555                 560
Lys Glu Phe Leu Asn Tyr Ile Asn Pro Arg Leu Pro Gly Leu Leu Glu
                565                 570                 575
Leu Glu Tyr Glu Gly Phe Tyr Arg Arg Gly Phe Phe Val Thr Lys Lys
            580                 585                 590
Lys Tyr Ala Val Ile Asp Glu Glu Asp Lys Ile Thr Thr Arg Gly Leu
        595                 600                 605
Glu Ile Val Arg Arg Asp Trp Ser Glu Ile Ala Lys Glu Thr Gln Ala
```

```
                610                 615                 620
Arg Val Leu Glu Ala Ile Leu Lys His Gly Asp Val Glu Glu Ala Val
625                 630                 635                 640

Arg Ile Val Lys Glu Val Thr Glu Lys Leu Ser Arg Tyr Glu Val Pro
                645                 650                 655

Pro Glu Lys Leu Val Ile Tyr Glu Gln Ile Thr Arg Asn Leu Arg Asp
                660                 665                 670

Tyr Arg Ala Thr Gly Pro His Val Ala Val Ala Lys Arg Leu Ala Ala
                675                 680                 685

Arg Gly Ile Lys Ile Arg Pro Gly Thr Val Ile Ser Tyr Ile Val Leu
690                 695                 700

Lys Gly Pro Gly Arg Val Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Lys Gln Ala Gly Leu Gly Ala Trp
                755                 760                 765

Leu Lys Pro Lys Thr Gly Ser
770                 775
```

<210> SEQ ID NO 6
<211> LENGTH: 774
<212> TYPE: PRT
<213> ORGANISM: Artificial sequence
<220> FEATURE:
<223> OTHER INFORMATION: Chimeric sequence

<400> SEQUENCE: 6

```
Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Lys Asp Asp Ser Gln Ile
            35                  40                  45

Asp Glu Val Arg Lys Ile Thr Ala Glu Arg His Gly Lys Ile Val Arg
        50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
        130                 135                 140

Leu Tyr His Glu Gly Glu Glu Phe Ala Lys Gly Pro Ile Ile Met Ile
145                 150                 155                 160

Ser Tyr Ala Asp Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
```

-continued

```
              195                 200                 205
Tyr Asn Gly Asp Ser Phe Asp Leu Pro Tyr Leu Val Lys Arg Ala Glu
              210                 215                 220
Lys Leu Gly Ile Lys Leu Pro Leu Gly Arg Asp Gly Ser Glu Pro Lys
225                 230                 235                 240
Met Gln Arg Leu Gly Asp Met Thr Ala Val Glu Ile Lys Gly Arg Ile
                  245                 250                 255
His Phe Asp Leu Tyr His Val Ile Arg Arg Thr Ile Asn Leu Pro Thr
              260                 265                 270
Tyr Thr Leu Glu Ala Val Tyr Glu Ala Ile Phe Gly Lys Pro Lys Glu
              275                 280                 285
Lys Val Tyr Ala His Glu Ile Ala Glu Ala Trp Glu Thr Gly Lys Gly
              290                 295                 300
Leu Glu Arg Val Ala Lys Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                  325                 330                 335
Val Gly Gln Ser Leu Trp Asp Val Ser Arg Ser Thr Gly Asn Leu
              340                 345                 350
Val Glu Trp Phe Leu Leu Arg Lys Ala Tyr Glu Arg Asn Glu Leu Ala
              355                 360                 365
Pro Asn Lys Pro Asp Glu Arg Glu Leu Ala Arg Arg Ala Glu Ser Tyr
370                 375                 380
Ala Gly Gly Tyr Val Lys Glu Pro Glu Lys Gly Leu Trp Glu Asn Ile
385                 390                 395                 400
Val Tyr Leu Asp Tyr Lys Ser Leu Tyr Pro Ser Ile Ile Thr His
                  405                 410                 415
Asn Val Ser Pro Asp Thr Leu Asn Arg Glu Gly Cys Arg Glu Tyr Asp
              420                 425                 430
Val Ala Pro Gln Val Gly His Arg Phe Cys Lys Asp Phe Pro Gly Phe
              435                 440                 445
Ile Pro Ser Leu Leu Gly Asp Leu Leu Glu Glu Arg Gln Lys Val Lys
              450                 455                 460
Lys Lys Met Lys Ala Thr Val Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                  485                 490                 495
Tyr Gly Tyr Ala Asn Ala Arg Trp Tyr Cys Arg Glu Cys Ala Glu Ser
              500                 505                 510
Val Thr Ala Trp Gly Arg Gln Tyr Ile Glu Thr Thr Met Arg Glu Ile
              515                 520                 525
Glu Glu Lys Phe Gly Phe Lys Val Leu Tyr Ala Asp Thr Asp Gly Phe
              530                 535                 540
Phe Ala Thr Ile Pro Gly Ala Asp Ala Glu Thr Val Lys Lys Lys Thr
545                 550                 555                 560
Lys Glu Phe Leu Asn Tyr Ile Asn Pro Arg Leu Pro Gly Leu Leu Glu
                  565                 570                 575
Leu Glu Tyr Glu Gly Phe Tyr Lys Arg Gly Phe Phe Val Thr Lys Lys
              580                 585                 590
Lys Tyr Ala Val Ile Asp Glu Glu Gly Lys Ile Thr Thr Arg Gly Leu
              595                 600                 605
Glu Ile Val Arg Arg Asp Trp Ser Glu Ile Ala Lys Glu Thr Gln Ala
              610                 615                 620
```

```
Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
            755                 760                 765

Leu Lys Pro Lys Gly Thr
770

<210> SEQ ID NO 7
<211> LENGTH: 774
<212> TYPE: PRT
<213> ORGANISM: Artificial sequence
<220> FEATURE:
<223> OTHER INFORMATION: Chimeric sequence

<400> SEQUENCE: 7

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
50                  55                  60

Ile Ile Asp Ala Glu Lys Val Arg Lys Phe Leu Gly Arg Pro Ile
65                  70                  75                  80

Glu Val Trp Arg Leu Tyr Phe Glu His Pro Gln Asp Val Pro Ala Ile
            85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
            165                 170                 175

Asp Leu Pro Tyr Val Glu Val Val Ser Ser Glu Arg Glu Met Ile Lys
        180                 185                 190

Arg Phe Leu Lys Val Ile Arg Glu Lys Asp Pro Asp Val Ile Ile Thr
        195                 200                 205
```

```
Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
            245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
        340                 345                 350

Val Glu Trp Phe Leu Leu Arg Lys Ala Tyr Glu Arg Asn Glu Leu Ala
    355                 360                 365

Pro Asn Lys Pro Asp Glu Arg Glu Leu Ala Arg Arg Ala Glu Ser Tyr
370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Arg Glu Tyr Asp
        420                 425                 430

Val Ala Pro Gln Val Gly His Arg Phe Cys Lys Asp Phe Pro Gly Phe
    435                 440                 445

Ile Pro Ser Leu Leu Gly Asp Leu Leu Glu Glu Arg Gln Lys Val Lys
450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
        500                 505                 510

Val Thr Ala Trp Gly Arg Gln Tyr Ile Glu Thr Thr Met Arg Glu Ile
    515                 520                 525

Glu Glu Lys Phe Gly Phe Lys Val Leu Tyr Ala Asp Thr Asp Gly Phe
530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Lys Arg Gly Phe Phe Val Thr Lys Lys
        580                 585                 590

Arg Tyr Ala Val Ile Asp Glu Glu Gly Lys Val Ile Thr Arg Gly Leu
    595                 600                 605

Glu Ile Val Arg Arg Asp Trp Ser Glu Ile Ala Lys Glu Thr Gln Ala
610                 615                 620
```

Arg Val Leu Glu Thr Ile Leu Lys His Gly Asp Val Glu Glu Ala Val
625                 630                 635                 640

Arg Ile Val Lys Glu Val Ile Gln Lys Leu Ala Asn Tyr Glu Ile Pro
            645                 650                 655

Pro Glu Lys Leu Ala Ile Tyr Glu Gln Ile Thr Arg Pro Leu His Glu
                660                 665                 670

Tyr Lys Ala Ile Gly Pro His Val Ala Val Lys Lys Leu Ala Ala
            675                 680                 685

Lys Gly Val Lys Ile Lys Pro Gly Met Val Ile Gly Tyr Ile Val Leu
    690                 695                 700

Arg Gly Asp Gly Pro Ile Ser Asn Arg Ala Ile Leu Ala Glu Glu Tyr
705                 710                 715                 720

Asp Pro Lys Lys His Lys Tyr Asp Ala Glu Tyr Tyr Ile Glu Asn Gln
                725                 730                 735

Val Leu Pro Ala Val Leu Arg Ile Leu Glu Gly Phe Gly Tyr Arg Lys
                740                 745                 750

Glu Asp Leu Arg Tyr Gln Lys Thr Arg Gln Val Gly Leu Thr Ser Trp
                755                 760                 765

Leu Asn Ile Lys Lys Ser
    770

<210> SEQ ID NO 8
<211> LENGTH: 773
<212> TYPE: PRT
<213> ORGANISM: Artificial sequence
<220> FEATURE:
<223> OTHER INFORMATION: Chimeric sequence

<400> SEQUENCE: 8

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

```
Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
            275                 280                 285

Lys Val Tyr Ala His Glu Ile Ala Glu Ala Trp Glu Thr Gly Lys Gly
290                 295                 300

Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Ala Arg Gly Phe Phe Val Thr Lys Lys
            580                 585                 590

Lys Tyr Ala Leu Ile Asp Glu Glu Gly Lys Ile Val Thr Arg Gly Leu
                595                 600                 605

Glu Ile Val Arg Arg Asp Trp Ser Glu Ile Ala Lys Glu Thr Gln Ala
            610                 615                 620

Lys Val Leu Glu Ala Ile Leu Lys His Gly Asn Val Asp Glu Ala Val
```

-continued

```
               625                 630                 635                 640
    Lys Ile Val Lys Glu Val Thr Glu Lys Leu Ser Lys Tyr Glu Ile Pro
                        645                 650                 655

Pro Glu Lys Leu Val Ile Tyr Glu Gln Ile Thr Arg Pro Leu Ser Glu
                    660                 665                 670

Tyr Lys Ala Ile Gly Pro His Val Ala Val Lys Arg Leu Ala Ala
                675                 680                 685

Lys Gly Val Lys Val Lys Pro Gly Met Val Ile Gly Tyr Ile Val Leu
                690                 695                 700

Arg Gly Asp Gly Pro Ile Ser Lys Arg Ala Ile Ala Ile Glu Glu Phe
    705                 710                 715                 720

Asp Pro Lys Lys His Lys Tyr Asp Ala Glu Tyr Tyr Ile Glu Asn Gln
                    725                 730                 735

Val Leu Pro Ala Val Glu Arg Ile Leu Arg Ala Phe Gly Tyr Arg Lys
                    740                 745                 750

Glu Asp Leu Lys Tyr Gln Lys Thr Lys Gln Val Gly Leu Gly Ala Trp
                    755                 760                 765

Leu Lys Phe Gly Ser
        770

<210> SEQ ID NO 9
<211> LENGTH: 775
<212> TYPE: PRT
<213> ORGANISM: Artificial sequence
<220> FEATURE:
<223> OTHER INFORMATION: Chimeric sequence

<400> SEQUENCE: 9

Met Ile Leu Asp Ala Asp Tyr Ile Thr Glu Asp Gly Lys Pro Ile Ile
    1               5                   10                  15

Arg Ile Phe Lys Lys Glu Asn Gly Glu Phe Lys Val Glu Tyr Asp Arg
                    20                  25                  30

Asn Phe Arg Pro Tyr Ile Tyr Ala Leu Leu Lys Asp Asp Ser Gln Ile
                35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
    65                  70                  75                  80

Glu Val Trp Arg Leu Tyr Phe Glu His Pro Gln Asp Val Pro Ala Ile
                    85                  90                  95

Arg Asp Lys Ile Arg Glu His Ser Ala Val Ile Asp Ile Phe Glu Tyr
                100                 105                 110

Asp Ile Pro Phe Ala Lys Arg Tyr Leu Ile Asp Lys Gly Leu Ile Pro
                115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
    145                 150                 155                 160

Ser Tyr Ala Asp Glu Glu Glu Ala Lys Val Ile Thr Trp Lys Lys Ile
                    165                 170                 175

Asp Leu Pro Tyr Val Glu Val Val Ser Ser Glu Arg Glu Met Ile Lys
                180                 185                 190

Arg Phe Leu Lys Val Ile Arg Glu Lys Asp Pro Asp Val Ile Ile Thr
                195                 200                 205

Tyr Asn Gly Asp Ser Phe Asp Leu Pro Tyr Leu Val Lys Arg Ala Glu
```

```
            210                 215                 220
Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala His Glu Ile Ala Glu Ala Trp Glu Thr Gly Lys Gly
                290                 295                 300

Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Lys Glu Leu Ala Arg Arg Gln Ser Tyr
                370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
                435                 440                 445

Ile Pro Ser Leu Leu Gly Asp Leu Leu Glu Glu Arg Gln Lys Ile Lys
                450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
                500                 505                 510

Val Thr Ala Trp Gly Arg Glu Tyr Ile Thr Met Thr Ile Lys Glu Ile
                515                 520                 525

Glu Glu Lys Tyr Gly Phe Lys Val Ile Tyr Ser Asp Thr Asp Gly Phe
                530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Arg Arg Gly Phe Phe Val Thr Lys Lys
                580                 585                 590

Lys Tyr Ala Val Ile Asp Glu Glu Asp Lys Ile Thr Thr Arg Gly Leu
                595                 600                 605

Glu Ile Val Arg Arg Asp Trp Ser Glu Ile Ala Lys Glu Thr Gln Ala
                610                 615                 620

Arg Val Leu Glu Ala Ile Leu Lys His Gly Asp Val Glu Glu Ala Val
625                 630                 635                 640
```

```
Arg Ile Val Lys Glu Val Thr Glu Lys Leu Ser Arg Tyr Glu Val Pro
            645                 650                 655

Pro Glu Lys Leu Val Ile Tyr Glu Gln Ile Thr Arg Asn Leu Arg Asp
            660                 665                 670

Tyr Arg Ala Thr Gly Pro His Val Ala Val Ala Lys Arg Leu Ala Ala
            675                 680                 685

Arg Gly Ile Lys Ile Arg Pro Gly Thr Val Ile Ser Tyr Ile Val Leu
            690                 695                 700

Lys Gly Pro Gly Arg Val Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Ala Gly Leu Gly Ala Trp
            755                 760                 765

Leu Lys Pro Lys Thr Gly Ser
            770                 775

<210> SEQ ID NO 10
<211> LENGTH: 774
<212> TYPE: PRT
<213> ORGANISM: Artificial sequence
<220> FEATURE:
<223> OTHER INFORMATION: Chimeric sequence

<400> SEQUENCE: 10

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
            85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
            165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220
```

```
Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
            245                 250                 255

His Phe Asp Leu Tyr His Val Ile Arg Arg Thr Ile Asn Leu Pro Thr
        260                 265                 270

Tyr Thr Leu Glu Ala Val Tyr Glu Ala Ile Phe Gly Lys Pro Lys Glu
    275                 280                 285

Lys Val Tyr Ala His Glu Ile Ala Glu Ala Trp Glu Thr Gly Lys Gly
290                 295                 300

Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
            325                 330                 335

Ile Gly Gln Ser Leu Trp Asp Val Ser Arg Ser Ser Thr Gly Asn Leu
        340                 345                 350

Val Glu Trp Phe Leu Arg Lys Ala Tyr Glu Arg Asn Glu Leu Ala
    355                 360                 365

Pro Asn Lys Pro Asp Glu Lys Glu Leu Ala Arg Arg Gln Ser Tyr
370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
            405                 410                 415

Asn Val Ser Pro Asp Thr Leu Asn Arg Glu Gly Cys Lys Glu Tyr Asp
        420                 425                 430

Val Ala Pro Gln Val Gly His Arg Phe Cys Lys Asp Phe Pro Gly Phe
    435                 440                 445

Ile Pro Ser Leu Leu Gly Asp Leu Leu Glu Glu Arg Gln Lys Ile Lys
450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
            485                 490                 495

Tyr Gly Tyr Ala Arg Ala Arg Trp Tyr Cys Lys Glu Cys Ala Glu Ser
        500                 505                 510

Val Thr Ala Trp Gly Arg Glu Tyr Ile Thr Met Thr Ile Lys Glu Ile
    515                 520                 525

Glu Glu Lys Tyr Gly Phe Lys Val Ile Tyr Ser Asp Thr Asp Gly Phe
            530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
            565                 570                 575

Leu Glu Tyr Glu Gly Phe Tyr Lys Arg Gly Phe Val Thr Lys Lys
        580                 585                 590

Lys Tyr Ala Val Ile Asp Glu Glu Gly Lys Ile Thr Thr Arg Gly Leu
    595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640
```

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Lys Asp
        660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
        690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
            755                 760                 765

Leu Lys Pro Lys Gly Thr
        770

<210> SEQ ID NO 11
<211> LENGTH: 774
<212> TYPE: PRT
<213> ORGANISM: Artificial sequence
<220> FEATURE:
<223> OTHER INFORMATION: Chimeric sequence

<400> SEQUENCE: 11

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

-continued

```
Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
            245                 250                 255

His Phe Asp Leu Tyr His Val Ile Arg Arg Thr Ile Asn Leu Pro Thr
        260                 265                 270

Tyr Thr Leu Glu Ala Val Tyr Glu Ala Ile Phe Gly Lys Pro Lys Glu
    275                 280                 285

Lys Val Tyr Ala His Glu Ile Ala Glu Ala Trp Glu Thr Gly Lys Gly
290                 295                 300

Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
            325                 330                 335

Ile Gly Gln Ser Leu Trp Asp Val Ser Arg Ser Ser Thr Gly Asn Leu
        340                 345                 350

Val Glu Trp Phe Leu Leu Arg Lys Ala Tyr Glu Arg Asn Glu Leu Ala
    355                 360                 365

Pro Asn Lys Pro Asp Glu Lys Glu Leu Ala Arg Arg Gln Ser Tyr
370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
            405                 410                 415

Asn Val Ser Pro Asp Thr Leu Asn Arg Glu Gly Cys Lys Glu Tyr Asp
        420                 425                 430

Val Ala Pro Gln Val Gly His Arg Phe Cys Lys Asp Phe Pro Gly Phe
    435                 440                 445

Ile Pro Ser Leu Leu Gly Asp Leu Leu Glu Glu Arg Gln Lys Ile Lys
450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
            485                 490                 495

Tyr Gly Tyr Ala Arg Ala Arg Trp Tyr Cys Lys Glu Cys Ala Glu Ser
        500                 505                 510

Val Thr Ala Trp Gly Arg Glu Tyr Ile Thr Met Thr Ile Lys Glu Ile
    515                 520                 525

Glu Glu Lys Tyr Gly Phe Lys Val Ile Tyr Ser Asp Thr Asp Gly Phe
530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
            565                 570                 575

Leu Glu Tyr Glu Gly Phe Tyr Lys Arg Gly Phe Phe Val Thr Lys Lys
        580                 585                 590

Arg Tyr Ala Val Ile Asp Glu Glu Gly Lys Val Ile Thr Arg Gly Leu
    595                 600                 605

Glu Ile Val Arg Arg Asp Trp Ser Glu Ile Ala Lys Glu Thr Gln Ala
610                 615                 620

Arg Val Leu Glu Thr Ile Leu Lys His Gly Asp Val Glu Glu Ala Val
625                 630                 635                 640

Arg Ile Val Lys Glu Val Ile Gln Lys Leu Ala Asn Tyr Glu Ile Pro
```

```
                    645                 650                 655
Pro Glu Lys Leu Ala Ile Tyr Glu Gln Ile Thr Arg Pro Leu His Glu
            660                 665                 670
Tyr Lys Ala Ile Gly Pro His Val Ala Val Ala Lys Lys Leu Ala Ala
            675                 680                 685
Lys Gly Val Lys Ile Lys Pro Gly Met Val Ile Gly Tyr Ile Val Leu
            690                 695                 700
Arg Gly Asp Gly Pro Ile Ser Asn Arg Ala Ile Leu Ala Glu Glu Tyr
705                 710                 715                 720
Asp Pro Lys Lys His Lys Tyr Asp Ala Glu Tyr Tyr Ile Glu Asn Gln
                725                 730                 735
Val Leu Pro Ala Val Leu Arg Ile Leu Glu Gly Phe Gly Tyr Arg Lys
            740                 745                 750
Glu Asp Leu Arg Tyr Gln Lys Thr Arg Gln Val Gly Leu Thr Ser Trp
            755                 760                 765
Leu Asn Ile Lys Lys Ser
            770
```

<210> SEQ ID NO 12
<211> LENGTH: 774
<212> TYPE: PRT
<213> ORGANISM: Artificial sequence
<220> FEATURE:
<223> OTHER INFORMATION: Chimeric sequence

<400> SEQUENCE: 12

```
Met Ile Leu Asp Ala Asp Tyr Ile Thr Glu Asp Gly Lys Pro Ile Ile
1               5                   10                  15
Arg Ile Phe Lys Lys Glu Asn Gly Glu Phe Lys Val Glu Tyr Asp Arg
                20                  25                  30
Asn Phe Arg Pro Tyr Ile Tyr Ala Leu Leu Lys Asp Asp Ser Gln Ile
            35                  40                  45
Asp Glu Val Arg Lys Ile Thr Ala Glu Arg His Gly Lys Ile Val Arg
        50                  55                  60
Ile Ile Asp Ala Glu Lys Val Arg Lys Lys Phe Leu Gly Arg Pro Ile
65                  70                  75                  80
Glu Val Trp Arg Leu Tyr Phe Glu His Pro Gln Asp Val Pro Ala Ile
                85                  90                  95
Arg Asp Lys Ile Arg Glu His Ser Ala Val Ile Asp Ile Phe Glu Tyr
            100                 105                 110
Asp Ile Pro Phe Ala Lys Arg Tyr Leu Ile Asp Lys Gly Leu Ile Pro
        115                 120                 125
Met Glu Gly Asp Glu Glu Leu Lys Leu Leu Ala Phe Asp Ile Glu Thr
130                 135                 140
Leu Tyr His Glu Gly Glu Glu Phe Ala Lys Gly Pro Ile Ile Met Ile
145                 150                 155                 160
Ser Tyr Ala Asp Glu Glu Glu Ala Lys Val Ile Thr Trp Lys Lys Ile
                165                 170                 175
Asp Leu Pro Tyr Val Glu Val Val Ser Ser Glu Arg Glu Met Ile Lys
            180                 185                 190
Arg Phe Leu Lys Val Ile Arg Glu Lys Asp Pro Asp Val Ile Ile Thr
        195                 200                 205
Tyr Asn Gly Asp Ser Phe Asp Leu Pro Tyr Leu Val Lys Arg Ala Glu
        210                 215                 220
Lys Leu Gly Ile Lys Leu Pro Leu Gly Arg Asp Gly Ser Glu Pro Lys
```

-continued

```
            225                 230                 235                 240
        Met Gln Arg Leu Gly Asp Met Thr Ala Val Glu Ile Lys Gly Arg Ile
                            245                 250                 255

His Phe Asp Leu Tyr His Val Ile Arg Arg Thr Ile Asn Leu Pro Thr
                            260                 265                 270

Tyr Thr Leu Glu Ala Val Tyr Glu Ala Ile Phe Gly Lys Pro Lys Glu
                            275                 280                 285

Lys Val Tyr Ala His Glu Ile Ala Glu Ala Trp Glu Thr Gly Lys Gly
                        290                 295                 300

Leu Glu Arg Val Ala Lys Tyr Ser Met Glu Asp Ala Lys Ala Thr Tyr
        305                 310                 315                 320

Glu Leu Gly Lys Glu Phe Leu Pro Met Glu Ile Gln Leu Ser Arg Leu
                            325                 330                 335

Val Gly Gln Pro Leu Trp Asp Val Ser Arg Ser Thr Gly Asn Leu
                            340                 345                 350

Val Glu Trp Phe Leu Leu Arg Lys Ala Tyr Glu Arg Asn Glu Val Ala
                        355                 360                 365

Pro Asn Lys Pro Ser Glu Glu Glu Tyr Gln Arg Arg Leu Arg Glu Ser
                    370                 375                 380

Tyr Thr Gly Gly Phe Val Lys Glu Pro Glu Lys Gly Leu Trp Glu Asn
        385                 390                 395                 400

Ile Val Tyr Leu Asp Phe Arg Ala Leu Tyr Pro Ser Ile Ile Ile Thr
                            405                 410                 415

His Asn Val Ser Pro Asp Thr Leu Asn Leu Glu Gly Cys Lys Asn Tyr
                        420                 425                 430

Asp Ile Ala Pro Gln Val Gly His Lys Phe Cys Lys Asp Ile Pro Gly
                    435                 440                 445

Phe Ile Pro Ser Leu Leu Gly His Leu Leu Glu Glu Arg Gln Lys Ile
                450                 455                 460

Lys Thr Lys Met Lys Glu Thr Gln Asp Pro Ile Glu Lys Ile Leu Leu
        465                 470                 475                 480

Asp Tyr Arg Gln Lys Ala Ile Lys Leu Leu Ala Asn Ser Phe Tyr Gly
                            485                 490                 495

Tyr Tyr Gly Tyr Ala Lys Ala Arg Trp Tyr Cys Lys Glu Cys Ala Glu
                        500                 505                 510

Ser Val Thr Ala Trp Gly Arg Lys Tyr Ile Glu Leu Val Trp Lys Glu
                        515                 520                 525

Leu Glu Glu Lys Phe Gly Phe Lys Val Leu Tyr Ile Asp Thr Asp Gly
                    530                 535                 540

Leu Tyr Ala Thr Ile Pro Gly Gly Glu Ser Glu Glu Ile Lys Lys Lys
        545                 550                 555                 560

Ala Leu Glu Phe Val Lys Tyr Ile Asn Ser Lys Leu Pro Gly Leu Leu
                            565                 570                 575

Glu Leu Glu Tyr Glu Gly Phe Tyr Ala Arg Gly Phe Phe Val Thr Lys
                        580                 585                 590

Lys Lys Tyr Ala Leu Ile Asp Glu Glu Gly Lys Ile Val Thr Arg Gly
                        595                 600                 605

Leu Glu Ile Val Arg Arg Asp Trp Ser Glu Ile Ala Lys Glu Thr Gln
                    610                 615                 620

Ala Lys Val Leu Glu Ala Ile Leu Lys His Gly Asn Val Asp Glu Ala
        625                 630                 635                 640

Val Lys Ile Val Lys Glu Val Thr Glu Lys Leu Ser Lys Tyr Glu Ile
                            645                 650                 655
```

```
Pro Pro Glu Lys Leu Val Ile Tyr Glu Gln Ile Thr Arg Pro Leu Ser
            660                 665                 670

Glu Tyr Lys Ala Ile Gly Pro His Val Ala Val Ala Lys Arg Leu Ala
        675                 680                 685

Ala Lys Gly Val Lys Val Lys Pro Gly Met Val Ile Gly Tyr Ile Val
    690                 695                 700

Leu Arg Gly Asp Gly Pro Ile Ser Lys Arg Ala Ile Ala Ile Glu Glu
705                 710                 715                 720

Phe Asp Pro Lys Lys His Lys Tyr Asp Ala Glu Tyr Ile Glu Asn
                725                 730                 735

Gln Val Leu Pro Ala Val Glu Arg Ile Leu Arg Ala Phe Gly Tyr Arg
                740                 745                 750

Lys Glu Asp Leu Lys Tyr Gln Lys Thr Lys Gln Val Gly Leu Gly Ala
            755                 760                 765

Trp Leu Lys Phe Gly Ser
            770

<210> SEQ ID NO 13
<211> LENGTH: 776
<212> TYPE: PRT
<213> ORGANISM: Artificial sequence
<220> FEATURE:
<223> OTHER INFORMATION: Chimeric sequence

<400> SEQUENCE: 13

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Lys Asp Asp Ser Gln Ile
            35                  40                  45

Asp Glu Val Arg Lys Ile Thr Ala Glu Arg His Gly Lys Ile Val Arg
        50                  55                  60

Ile Ile Asp Ala Glu Lys Val Arg Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240
```

```
Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala His Glu Ile Ala Glu Ala Trp Glu Thr Gly Lys Gly
                290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Val Ala
                355                 360                 365

Pro Asn Lys Pro Ser Glu Glu Tyr Gln Arg Arg Leu Arg Glu Ser
                370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
                435                 440                 445

Phe Ile Pro Ser Leu Leu Gly His Leu Leu Glu Glu Arg Gln Lys Ile
                450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Lys Tyr Ile Glu Leu Val Trp Lys Glu
                515                 520                 525

Leu Glu Glu Lys Phe Gly Phe Lys Val Leu Tyr Ile Asp Thr Asp Gly
                530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Arg Arg Gly Phe Phe Val Thr Lys
                580                 585                 590

Lys Lys Tyr Ala Val Ile Asp Glu Glu Asp Lys Ile Thr Thr Arg Gly
                595                 600                 605

Leu Glu Ile Val Arg Arg Asp Trp Ser Glu Ile Ala Lys Glu Thr Gln
                610                 615                 620

Ala Arg Val Leu Glu Ala Ile Leu Lys His Gly Asp Val Glu Glu Ala
625                 630                 635                 640

Val Arg Ile Val Lys Glu Val Thr Glu Lys Leu Ser Arg Tyr Glu Val
                645                 650                 655
```

```
Pro Pro Glu Lys Leu Val Ile Tyr Glu Gln Ile Thr Arg Asn Leu Arg
            660                 665                 670

Asp Tyr Arg Ala Thr Gly Pro His Val Ala Val Ala Lys Arg Leu Ala
        675                 680                 685

Ala Arg Gly Ile Lys Ile Arg Pro Gly Thr Val Ile Ser Tyr Ile Val
    690                 695                 700

Leu Lys Gly Pro Gly Arg Val Gly Asp Arg Ala Ile Pro Phe Asp Glu
705                 710                 715                 720

Phe Asp Pro Ala Lys His Arg Tyr Asp Ala Glu Tyr Tyr Ile Glu Asn
            725                 730                 735

Gln Val Leu Pro Ala Val Glu Arg Ile Leu Arg Ala Phe Gly Tyr Arg
        740                 745                 750

Lys Glu Asp Leu Arg Tyr Gln Lys Thr Lys Gln Ala Gly Leu Gly Ala
    755                 760                 765

Trp Leu Lys Pro Lys Thr Gly Ser
770                 775

<210> SEQ ID NO 14
<211> LENGTH: 775
<212> TYPE: PRT
<213> ORGANISM: Artificial sequence
<220> FEATURE:
<223> OTHER INFORMATION: Chimeric sequence

<400> SEQUENCE: 14

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
            85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
            165                 170                 175

Asp Leu Pro Tyr Val Glu Val Val Ser Ser Glu Arg Glu Met Ile Lys
        180                 185                 190

Arg Phe Leu Lys Val Ile Arg Glu Lys Asp Pro Asp Val Ile Ile Thr
    195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240
```

```
Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Val Ile Asp Glu Glu Gly Lys Ile Thr Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Ala Leu Leu Lys Asp Gly Asp Val Glu Lys Ala
625                 630                 635                 640

Val Arg Ile Val Lys Glu Val Thr Glu Lys Leu Ser Lys Tyr Glu Val
                645                 650                 655

Pro Pro Glu Lys Leu Val Ile His Glu Gln Ile Thr Arg Asp Leu Lys
```

```
            660                 665                 670
Asp Tyr Lys Ala Thr Gly Pro His Val Ala Val Ala Lys Arg Leu Ala
            675                 680                 685

Ala Arg Gly Val Lys Ile Arg Pro Gly Thr Val Ile Ser Tyr Ile Val
        690                 695                 700

Leu Lys Gly Ser Gly Arg Ile Gly Asp Arg Ala Ile Pro Phe Asp Glu
705                 710                 715                 720

Phe Asp Pro Thr Lys His Lys Tyr Asp Ala Glu Tyr Tyr Ile Glu Asn
                725                 730                 735

Gln Val Leu Pro Ala Val Glu Arg Ile Leu Arg Ala Phe Gly Tyr Arg
            740                 745                 750

Lys Glu Asp Leu Arg Tyr Gln Lys Thr Arg Gln Val Gly Leu Ser Ala
                755                 760                 765

Trp Leu Lys Pro Lys Gly Thr
770                 775

<210> SEQ ID NO 15
<211> LENGTH: 776
<212> TYPE: PRT
<213> ORGANISM: Artificial sequence
<220> FEATURE:
<223> OTHER INFORMATION: Chimeric sequence

<400> SEQUENCE: 15

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
    50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
```

```
            245                 250                 255
His Phe Asp Leu Phe Pro Val Ile Arg Arg Thr Ile Asn Leu Pro Thr
                260                 265                 270
Tyr Thr Leu Glu Ala Val Tyr Glu Ala Ile Phe Gly Lys Ser Lys Glu
            275                 280                 285
Lys Val Tyr Ala His Glu Ile Ala Glu Ala Trp Glu Thr Gly Lys Gly
290                 295                 300
Leu Glu Arg Val Ala Lys Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Val Gly Gln Pro Leu Trp Asp Val Ser Arg Ser Thr Gly Asn Leu
                340                 345                 350
Val Glu Trp Tyr Leu Leu Arg Lys Ala Tyr Glu Arg Asn Glu Leu Ala
                355                 360                 365
Pro Asn Lys Pro Asp Glu Arg Glu Tyr Glu Arg Arg Leu Arg Glu Ser
            370                 375                 380
Tyr Ala Gly Gly Tyr Val Lys Glu Pro Glu Lys Gly Leu Trp Glu Gly
385                 390                 395                 400
Leu Val Ser Leu Asp Phe Arg Ser Leu Tyr Pro Ser Ile Ile Ile Thr
                405                 410                 415
His Asn Val Ser Pro Asp Thr Leu Asn Arg Glu Gly Cys Arg Glu Tyr
                420                 425                 430
Asp Val Ala Pro Glu Val Gly His Lys Phe Cys Lys Asp Phe Pro Gly
                435                 440                 445
Phe Ile Pro Ser Leu Leu Lys Arg Leu Leu Asp Glu Arg Gln Glu Ile
            450                 455                 460
Lys Arg Lys Met Lys Ala Ser Lys Asp Pro Ile Glu Lys Lys Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
                500                 505                 510
Ser Val Thr Ala Trp Gly Arg Glu Tyr Ile Glu Phe Val Arg Lys Glu
            515                 520                 525
Leu Glu Glu Lys Phe Gly Phe Lys Val Leu Tyr Ile Asp Thr Asp Gly
            530                 535                 540
Leu Tyr Ala Thr Ile Pro Gly Ala Lys Pro Glu Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Arg Arg Gly Phe Phe Val Thr Lys
                580                 585                 590
Lys Lys Tyr Ala Val Ile Asp Glu Glu Asp Lys Ile Thr Thr Arg Gly
                595                 600                 605
Leu Glu Ile Val Arg Arg Asp Trp Ser Glu Ile Ala Lys Glu Thr Gln
            610                 615                 620
Ala Arg Val Leu Glu Ala Ile Leu Lys His Gly Asp Val Glu Glu Ala
625                 630                 635                 640
Val Arg Ile Val Lys Glu Val Thr Glu Lys Leu Ser Arg Tyr Glu Val
                645                 650                 655
Pro Pro Glu Lys Leu Val Ile Tyr Glu Gln Ile Thr Arg Asn Leu Arg
                660                 665                 670
```

```
Asp Tyr Arg Ala Thr Gly Pro His Val Ala Ala Lys Arg Leu Ala
        675                 680                 685

Ala Arg Gly Ile Lys Ile Arg Pro Gly Thr Val Ile Ser Tyr Ile Val
    690                 695                 700

Leu Lys Gly Pro Gly Arg Val Gly Asp Arg Ala Ile Pro Phe Asp Glu
705                 710                 715                 720

Phe Asp Pro Ala Lys His Arg Tyr Asp Ala Glu Tyr Tyr Ile Glu Asn
                725                 730                 735

Gln Val Leu Pro Ala Val Glu Arg Ile Leu Arg Ala Phe Gly Tyr Arg
                740                 745                 750

Lys Glu Asp Leu Arg Tyr Gln Lys Thr Lys Gln Ala Gly Leu Gly Ala
                755                 760                 765

Trp Leu Lys Pro Lys Thr Gly Ser
    770                 775
```

<210> SEQ ID NO 16
<211> LENGTH: 775
<212> TYPE: PRT
<213> ORGANISM: Artificial sequence
<220> FEATURE:
<223> OTHER INFORMATION: Chimeric sequence

<400> SEQUENCE: 16

```
Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
                20                  25                  30

Thr Phe Arg Pro Tyr Ile Tyr Ala Leu Leu Lys Asp Asp Ser Ala Ile
            35                  40                  45

Asp Glu Val Lys Lys Ile Thr Ala Glu Arg His Gly Lys Ile Val Arg
50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
                100                 105                 110

Asp Ile Pro Phe Ala Lys Arg Tyr Leu Ile Asp Lys Gly Leu Thr Pro
            115                 120                 125

Met Glu Gly Asn Glu Glu Leu Thr Phe Leu Ala Val Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
            195                 200                 205

Tyr Asn Gly Asp Asn Phe Asp Phe Pro Tyr Leu Leu Lys Arg Ala Glu
210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255
```

```
His Phe Asp Leu Phe Pro Val Ile Arg Arg Thr Ile Asn Leu Pro Thr
            260                 265                 270
Tyr Thr Leu Glu Ala Val Tyr Glu Ala Ile Phe Gly Lys Ser Lys Glu
        275                 280                 285
Lys Val Tyr Ala His Glu Ile Ala Glu Ala Trp Glu Thr Gly Lys Gly
    290                 295                 300
Leu Glu Arg Val Ala Lys Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Val Gly Gln Pro Leu Trp Asp Val Ser Arg Ser Thr Gly Asn Leu
            340                 345                 350
Val Glu Trp Tyr Leu Leu Arg Lys Ala Tyr Glu Arg Asn Glu Leu Ala
        355                 360                 365
Pro Asn Lys Pro Asp Glu Arg Glu Tyr Glu Arg Arg Leu Arg Glu Ser
    370                 375                 380
Tyr Ala Gly Gly Tyr Val Lys Glu Pro Glu Lys Gly Leu Trp Glu Gly
385                 390                 395                 400
Leu Val Ser Leu Asp Phe Arg Ser Leu Tyr Pro Ser Ile Ile Ile Thr
                405                 410                 415
His Asn Val Ser Pro Asp Thr Leu Asn Arg Glu Gly Cys Arg Glu Tyr
            420                 425                 430
Asp Val Ala Pro Glu Val Gly His Lys Phe Cys Lys Asp Phe Pro Gly
        435                 440                 445
Phe Ile Pro Ser Leu Leu Lys Arg Leu Leu Asp Glu Arg Gln Glu Ile
    450                 455                 460
Lys Arg Lys Met Lys Ala Ser Lys Asp Pro Ile Glu Lys Lys Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Arg Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Ala Lys Pro Glu Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Lys Tyr Ala Val Ile Asp Glu Glu Gly Lys Ile Thr Thr Arg Gly
        595                 600                 605
Leu Glu Ile Val Arg Arg Asp Trp Ser Glu Ile Ala Lys Glu Thr Gln
    610                 615                 620
Ala Arg Val Leu Glu Ala Leu Leu Lys Asp Gly Asp Val Glu Lys Ala
625                 630                 635                 640
Val Arg Ile Val Lys Glu Val Thr Glu Lys Leu Ser Lys Tyr Glu Val
                645                 650                 655
Pro Pro Glu Lys Leu Val Ile His Glu Gln Ile Thr Arg Asp Leu Lys
            660                 665                 670
```

```
Asp Tyr Lys Ala Thr Gly Pro His Val Ala Val Ala Lys Arg Leu Ala
            675                 680                 685

Ala Arg Gly Val Lys Ile Arg Pro Gly Thr Val Ile Ser Tyr Ile Val
        690                 695                 700

Leu Lys Gly Ser Gly Arg Ile Gly Asp Arg Ala Ile Pro Phe Asp Glu
705                 710                 715                 720

Phe Asp Pro Thr Lys His Lys Tyr Asp Ala Glu Tyr Ile Glu Asn
            725                 730                 735

Gln Val Leu Pro Ala Val Glu Arg Ile Leu Arg Ala Phe Gly Tyr Arg
                740                 745                 750

Lys Glu Asp Leu Arg Tyr Gln Lys Thr Arg Gln Val Gly Leu Ser Ala
            755                 760                 765

Trp Leu Lys Pro Lys Gly Thr
            770                 775

<210> SEQ ID NO 17
<211> LENGTH: 775
<212> TYPE: PRT
<213> ORGANISM: Artificial sequence
<220> FEATURE:
<223> OTHER INFORMATION: Chimeric sequence

<400> SEQUENCE: 17

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
    50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255
```

```
His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
```

```
                    675                 680                 685
Ala Lys Gly Val Lys Ile Lys Pro Gly Met Val Ile Gly Tyr Ile Val
            690                 695                 700
Leu Arg Gly Asp Gly Pro Ile Ser Asn Arg Ala Ile Leu Ala Glu Glu
705                 710                 715                 720
Tyr Asp Pro Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Tyr Gln Lys Thr Arg Gln Val Gly Leu Thr Ser
            755                 760                 765
Trp Leu Asn Ile Lys Lys Ser
            770                 775

<210> SEQ ID NO 18
<211> LENGTH: 776
<212> TYPE: PRT
<213> ORGANISM: Artificial sequence
<220> FEATURE:
<223> OTHER INFORMATION: Chimeric sequence

<400> SEQUENCE: 18

Met Ile Ile Asp Ala Asp Tyr Ile Thr Glu Asp Gly Lys Pro Ile Ile
1               5                   10                  15
Arg Ile Phe Lys Lys Glu Lys Gly Glu Phe Lys Val Glu Tyr Asp Arg
            20                  25                  30
Thr Phe Arg Pro Tyr Ile Tyr Ala Leu Leu Lys Asp Asp Ser Ala Ile
            35                  40                  45
Asp Glu Val Lys Lys Ile Thr Ala Glu Arg His Gly Lys Ile Val Arg
50                  55                  60
Ile Thr Glu Val Glu Lys Val Gln Lys Lys Phe Leu Gly Arg Pro Ile
65                  70                  75                  80
Glu Val Trp Lys Leu Tyr Leu Glu His Pro Gln Asp Val Pro Ala Ile
                85                  90                  95
Arg Glu Lys Ile Arg Glu His Pro Ala Val Val Asp Ile Phe Glu Tyr
            100                 105                 110
Asp Ile Pro Phe Ala Lys Arg Tyr Leu Ile Asp Lys Gly Leu Thr Pro
            115                 120                 125
Met Glu Gly Asn Glu Glu Leu Thr Phe Leu Ala Val Asp Ile Glu Thr
130                 135                 140
Leu Tyr His Glu Gly Glu Glu Phe Gly Lys Gly Pro Ile Ile Met Ile
145                 150                 155                 160
Ser Tyr Ala Asp Glu Glu Gly Ala Lys Val Ile Thr Trp Lys Ser Ile
                165                 170                 175
Asp Leu Pro Tyr Val Glu Val Ser Ser Glu Arg Glu Met Ile Lys
            180                 185                 190
Arg Leu Val Lys Val Ile Arg Glu Lys Asp Pro Asp Val Ile Ile Thr
            195                 200                 205
Tyr Asn Gly Asp Asn Phe Asp Phe Pro Tyr Leu Leu Lys Arg Ala Glu
            210                 215                 220
Lys Leu Gly Ile Lys Leu Pro Leu Gly Arg Asp Asn Ser Glu Pro Lys
225                 230                 235                 240
Met Gln Arg Met Gly Asp Ser Leu Ala Val Glu Ile Lys Gly Arg Ile
                245                 250                 255
His Phe Asp Leu Phe Pro Val Ile Arg Arg Thr Ile Asn Leu Pro Thr
```

-continued

```
                260                 265                 270
Tyr Thr Leu Glu Ala Val Tyr Glu Ala Ile Phe Gly Lys Ser Lys Glu
        275                 280                 285
Lys Val Tyr Ala His Glu Ile Ala Glu Ala Trp Glu Thr Gly Lys Gly
        290                 295                 300
Leu Glu Arg Val Ala Lys Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Ser Leu Trp Asp Val Ser Arg Ser Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Asp Glu Arg Glu Leu Ala Arg Ala Glu Ser Tyr
        370                 375                 380
Ala Gly Gly Tyr Val Lys Glu Pro Glu Lys Gly Leu Trp Glu Asn Ile
385                 390                 395                 400
Val Tyr Leu Asp Tyr Lys Ser Leu Tyr Pro Ser Ile Ile Ile Thr His
                405                 410                 415
Asn Val Ser Pro Asp Thr Leu Asn Arg Glu Gly Cys Arg Glu Tyr Asp
                420                 425                 430
Val Ala Pro Gln Val Gly His Arg Phe Cys Lys Asp Phe Pro Gly Phe
                435                 440                 445
Ile Pro Ser Leu Leu Gly Asp Leu Leu Glu Glu Arg Gln Lys Val Lys
        450                 455                 460
Lys Lys Met Lys Ala Thr Val Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Asn Ala Arg Trp Tyr Cys Arg Glu Cys Ala Glu Ser
                500                 505                 510
Val Thr Ala Trp Gly Arg Gln Tyr Ile Glu Thr Thr Met Arg Glu Ile
                515                 520                 525
Glu Glu Lys Phe Gly Phe Lys Val Leu Tyr Ala Asp Thr Asp Gly Phe
        530                 535                 540
Phe Ala Thr Ile Pro Gly Ala Asp Ala Glu Thr Val Lys Lys Lys Thr
545                 550                 555                 560
Lys Glu Phe Leu Asn Tyr Ile Asn Pro Arg Leu Pro Gly Leu Leu Glu
                565                 570                 575
Leu Glu Tyr Glu Gly Phe Tyr Val Arg Gly Phe Phe Val Thr Lys Lys
                580                 585                 590
Lys Tyr Ala Leu Ile Asp Glu Glu Gly Lys Ile Ile Thr Arg Gly Leu
                595                 600                 605
Glu Ile Val Arg Arg Asp Trp Ser Glu Ile Ala Lys Glu Thr Gln Ala
        610                 615                 620
Lys Val Leu Glu Ala Ile Leu Lys His Gly Asn Val Glu Glu Ala Val
625                 630                 635                 640
Lys Ile Val Lys Glu Val Thr Glu Lys Leu Ser Lys Tyr Glu Ile Pro
                645                 650                 655
Pro Glu Lys Leu Val Ile Tyr Glu Gln Ile Thr Arg Pro Leu His Glu
                660                 665                 670
Tyr Lys Ala Ile Gly Pro His Val Ala Val Ala Lys Arg Leu Ala Ala
                675                 680                 685
```

```
Arg Gly Val Lys Val Arg Pro Gly Met Val Ile Gly Tyr Ile Val Leu
            690                 695                 700

Arg Gly Asp Gly Pro Ile Ser Lys Arg Ala Ile Leu Ala Glu Glu Phe
705                 710                 715                 720

Asp Leu Arg Lys His Lys Tyr Asp Ala Glu Tyr Tyr Ile Glu Asn Gln
                725                 730                 735

Val Leu Pro Ala Val Leu Arg Ile Leu Glu Ala Phe Gly Tyr Arg Lys
            740                 745                 750

Glu Asp Leu Arg Trp Gln Lys Thr Lys Gln Thr Gly Leu Thr Ala Trp
            755                 760                 765

Leu Asn Ile Lys Lys Lys Gly Ser
770                 775

<210> SEQ ID NO 19
<211> LENGTH: 775
<212> TYPE: PRT
<213> ORGANISM: Artificial sequence
<220> FEATURE:
<223> OTHER INFORMATION: Chimeric sequence

<400> SEQUENCE: 19

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Gly Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
    50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270
```

```
Tyr Thr Leu Glu Ala Val Tyr Glu Ala Ile Phe Gly Lys Ser Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Ala Glu Ser Tyr
    370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Arg Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Arg Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg Tyr Glu Val Pro
                645                 650                 655

Pro Glu Lys Leu Val Ile Tyr Glu Gln Ile Thr Arg Asn Leu Arg Asp
            660                 665                 670

Tyr Arg Ala Thr Gly Pro His Val Ala Val Ala Lys Arg Leu Ala Ala
        675                 680                 685
```

```
Arg Gly Ile Lys Ile Arg Pro Gly Thr Val Ile Ser Tyr Ile Val Leu
    690             695                 700

Lys Gly Pro Gly Arg Val Gly Asp Arg Ala Ile Pro Phe Asp Glu Phe
705             710                 715                 720

Asp Pro Ala Lys His Arg Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Ala Gly Leu Gly Ala Trp
        755                 760                 765

Leu Lys Pro Lys Thr Gly Ser
    770             775

<210> SEQ ID NO 20
<211> LENGTH: 774
<212> TYPE: PRT
<213> ORGANISM: Artificial sequence
<220> FEATURE:
<223> OTHER INFORMATION: Chimeric sequence

<400> SEQUENCE: 20

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270
```

```
Tyr Thr Leu Glu Ala Val Tyr Glu Ala Ile Phe Gly Lys Ser Lys Glu
            275                 280                 285

Lys Val Tyr Ala His Glu Ile Ala Glu Ala Trp Glu Thr Gly Lys Gly
        290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Ala Glu Ser Tyr
    370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Arg Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
            500                 505                 510

Val Thr Ala Trp Gly Arg Gln Tyr Ile Glu Thr Met Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
```

```
            690                 695                 700
Lys Gly Ser Gly Arg Ile Gly Asp Arg Ala Ile Pro Phe Asp Glu Phe
705                     710                 715                 720

Asp Pro Thr Lys His Lys Tyr Asp Ala Glu Tyr Tyr Ile Glu Asn Gln
                    725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Arg Gln Val Gly Leu Ser Ala Trp
            755                 760                 765

Leu Lys Pro Lys Gly Thr
    770

<210> SEQ ID NO 21
<211> LENGTH: 774
<212> TYPE: PRT
<213> ORGANISM: Artificial sequence
<220> FEATURE:
<223> OTHER INFORMATION: Chimeric sequence

<400> SEQUENCE: 21

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
                20                  25                  30

Thr Phe Arg Pro Tyr Ile Tyr Ala Leu Leu Lys Asp Asp Ser Ala Ile
            35                  40                  45

Asp Glu Val Lys Lys Ile Thr Ala Glu Arg His Gly Lys Ile Val Arg
50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
```

-continued

```
                275                 280                 285
Lys Val Tyr Ala His Glu Ile Ala Glu Ala Trp Glu Thr Gly Lys Gly
            290                 295                 300
Leu Glu Arg Val Ala Lys Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Ser Leu Trp Asp Val Ser Arg Ser Thr Gly Asn Leu
            340                 345                 350
Val Glu Trp Phe Leu Leu Arg Lys Ala Tyr Glu Arg Asn Glu Leu Ala
                355                 360                 365
Pro Asn Lys Pro Asp Glu Arg Glu Leu Ala Arg Arg Ala Glu Ser Tyr
            370                 375                 380
Ala Gly Gly Tyr Val Lys Glu Pro Glu Lys Gly Leu Trp Glu Asn Ile
385                 390                 395                 400
Val Tyr Leu Asp Tyr Lys Ser Leu Tyr Pro Ser Ile Ile Ile Thr His
                405                 410                 415
Asn Val Ser Pro Asp Thr Leu Asn Arg Glu Gly Cys Arg Glu Tyr Asp
            420                 425                 430
Val Ala Pro Gln Val Gly His Arg Phe Cys Lys Asp Phe Pro Gly Phe
                435                 440                 445
Ile Pro Ser Leu Leu Gly Asp Leu Leu Glu Glu Arg Gln Lys Val Lys
            450                 455                 460
Lys Lys Met Lys Ala Thr Val Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Asn Ala Arg Trp Tyr Cys Arg Glu Cys Ala Glu Ser
            500                 505                 510
Val Thr Ala Trp Gly Arg Gln Tyr Ile Glu Thr Thr Met Arg Glu Ile
            515                 520                 525
Glu Glu Lys Phe Gly Phe Lys Val Leu Tyr Ala Asp Thr Asp Gly Phe
            530                 535                 540
Phe Ala Thr Ile Pro Gly Ala Asp Ala Glu Thr Val Lys Lys Lys Thr
545                 550                 555                 560
Lys Glu Phe Leu Asn Tyr Ile Asn Pro Arg Leu Pro Gly Leu Leu Glu
                565                 570                 575
Leu Glu Tyr Glu Gly Phe Tyr Lys Arg Gly Phe Phe Val Thr Lys Lys
            580                 585                 590
Arg Tyr Ala Val Ile Asp Glu Glu Gly Lys Val Ile Thr Arg Gly Leu
            595                 600                 605
Glu Ile Val Arg Arg Asp Trp Ser Glu Ile Ala Lys Glu Thr Gln Ala
            610                 615                 620
Arg Val Leu Glu Thr Ile Leu Lys His Gly Asp Val Glu Glu Ala Val
625                 630                 635                 640
Arg Ile Val Lys Glu Val Ile Gln Lys Leu Ala Asn Tyr Glu Ile Pro
                645                 650                 655
Pro Glu Lys Leu Ala Ile Tyr Glu Gln Ile Thr Arg Pro Leu His Glu
            660                 665                 670
Tyr Lys Ala Ile Gly Pro His Val Ala Val Ala Lys Lys Leu Ala Ala
            675                 680                 685
Lys Gly Val Lys Ile Lys Pro Gly Met Val Ile Gly Tyr Ile Val Leu
            690                 695                 700
```

Arg Gly Asp Gly Pro Ile Ser Asn Arg Ala Ile Leu Ala Glu Glu Tyr
705                 710                 715                 720

Asp Pro Lys Lys His Lys Tyr Asp Ala Glu Tyr Tyr Ile Glu Asn Gln
            725                 730                 735

Val Leu Pro Ala Val Leu Arg Ile Leu Glu Gly Phe Gly Tyr Arg Lys
        740                 745                 750

Glu Asp Leu Arg Tyr Gln Lys Thr Arg Gln Val Gly Leu Thr Ser Trp
    755                 760                 765

Leu Asn Ile Lys Lys Ser
    770

<210> SEQ ID NO 22
<211> LENGTH: 776
<212> TYPE: PRT
<213> ORGANISM: Artificial sequence
<220> FEATURE:
<223> OTHER INFORMATION: Chimeric sequence

<400> SEQUENCE: 22

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
    50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Gln Ser Tyr
370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Val Arg Gly Phe Phe Val Thr Lys Lys
            580                 585                 590

Lys Tyr Ala Leu Ile Asp Glu Glu Gly Lys Ile Ile Thr Arg Gly Leu
        595                 600                 605

Glu Ile Val Arg Arg Asp Trp Ser Glu Ile Ala Lys Glu Thr Gln Ala
610                 615                 620

Lys Val Leu Glu Ala Ile Leu Lys His Gly Asn Val Glu Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu His Glu
            660                 665                 670

Tyr Lys Ala Ile Gly Pro His Val Ala Val Ala Lys Arg Leu Ala Ala
        675                 680                 685

Arg Gly Val Lys Val Arg Pro Gly Met Val Ile Gly Tyr Ile Val Leu
690                 695                 700

```
Arg Gly Asp Gly Pro Ile Ser Lys Arg Ala Ile Leu Ala Glu Glu Phe
705                 710                 715                 720

Asp Leu Arg Lys His Lys Tyr Asp Ala Glu Tyr Tyr Ile Glu Asn Gln
                725                 730                 735

Val Leu Pro Ala Val Leu Arg Ile Leu Glu Ala Phe Gly Tyr Arg Lys
            740                 745                 750

Glu Asp Leu Arg Trp Gln Lys Thr Lys Gln Thr Gly Leu Thr Ala Trp
        755                 760                 765

Leu Asn Ile Lys Lys Lys Gly Ser
    770                 775

<210> SEQ ID NO 23
<211> LENGTH: 773
<212> TYPE: PRT
<213> ORGANISM: Artificial sequence
<220> FEATURE:
<223> OTHER INFORMATION: Chimeric sequence

<400> SEQUENCE: 23

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
                20                  25                  30

Thr Phe Arg Pro Tyr Ile Tyr Ala Leu Leu Lys Asp Asp Ser Ala Ile
            35                  40                  45

Asp Glu Val Lys Lys Ile Thr Ala Glu Arg His Gly Lys Ile Val Arg
        50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
                100                 105                 110

Asp Ile Pro Phe Ala Lys Arg Tyr Leu Ile Asp Lys Gly Leu Thr Pro
            115                 120                 125

Met Glu Gly Asn Glu Glu Leu Thr Phe Leu Ala Val Asp Ile Glu Thr
        130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
        275                 280                 285
```

-continued

```
Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Gln Ser Tyr
370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Ala Arg Gly Phe Phe Val Thr Lys Lys
            580                 585                 590

Lys Tyr Ala Leu Ile Asp Glu Glu Gly Lys Ile Val Thr Arg Gly Leu
        595                 600                 605

Glu Ile Val Arg Arg Asp Trp Ser Glu Ile Ala Lys Glu Thr Gln Ala
610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
            660                 665                 670

Tyr Lys Ala Ile Gly Pro His Val Ala Val Ala Lys Arg Leu Ala Ala
        675                 680                 685

Lys Gly Val Lys Val Lys Pro Gly Met Val Ile Gly Tyr Ile Val Leu
690                 695                 700

Arg Gly Asp Gly Pro Ile Ser Lys Arg Ala Ile Ala Ile Glu Glu Phe
```

```
            705                 710                 715                 720
Asp Pro Lys Lys His Lys Tyr Asp Ala Glu Tyr Tyr Ile Glu Asn Gln
                    725                 730                 735

Val Leu Pro Ala Val Glu Arg Ile Leu Arg Ala Phe Gly Tyr Arg Lys
                740                 745                 750

Glu Asp Leu Lys Tyr Gln Lys Thr Lys Gln Val Gly Leu Gly Ala Trp
                755                 760                 765

Leu Lys Phe Gly Ser
        770

<210> SEQ ID NO 24
<211> LENGTH: 775
<212> TYPE: PRT
<213> ORGANISM: Artificial sequence
<220> FEATURE:
<223> OTHER INFORMATION: Chimeric sequence

<400> SEQUENCE: 24

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
                20                  25                  30

Thr Phe Arg Pro Tyr Ile Tyr Ala Leu Leu Lys Asp Asp Ser Ala Ile
            35                  40                  45

Asp Glu Val Lys Lys Ile Thr Ala Glu Arg His Gly Lys Ile Val Arg
        50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
                100                 105                 110

Asp Ile Pro Phe Ala Lys Arg Tyr Leu Ile Asp Lys Gly Leu Thr Pro
            115                 120                 125

Met Glu Gly Asn Glu Glu Leu Thr Phe Leu Ala Val Asp Ile Glu Thr
        130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
                180                 185                 190

Arg Leu Val Lys Val Ile Arg Glu Lys Asp Pro Asp Val Ile Ile Thr
            195                 200                 205

Tyr Asn Gly Asp Asn Phe Asp Phe Pro Tyr Leu Leu Lys Arg Ala Glu
        210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
                260                 265                 270

Tyr Thr Leu Glu Ala Val Tyr Glu Ala Ile Phe Gly Lys Ser Lys Glu
            275                 280                 285

Lys Val Tyr Ala His Glu Ile Ala Glu Ala Trp Glu Thr Gly Lys Gly
```

```
                290                 295                 300
Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Lys Glu Leu Ala Arg Arg Gln Ser Tyr
370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
                435                 440                 445

Ile Pro Ser Leu Leu Gly Asp Leu Leu Glu Glu Arg Gln Lys Ile Lys
                450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
                500                 505                 510

Val Thr Ala Trp Gly Arg Glu Tyr Ile Thr Met Thr Ile Lys Glu Ile
                515                 520                 525

Glu Glu Lys Tyr Gly Phe Lys Val Ile Tyr Ser Asp Thr Asp Gly Phe
                530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Arg Arg Gly Phe Phe Val Thr Lys Lys
                580                 585                 590

Lys Tyr Ala Val Ile Asp Glu Glu Asp Lys Ile Thr Thr Arg Gly Leu
                595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg Tyr Glu Val Pro
                645                 650                 655

Pro Glu Lys Leu Val Ile Tyr Glu Gln Ile Thr Arg Asn Leu Arg Asp
                660                 665                 670

Tyr Arg Ala Thr Gly Pro His Val Ala Val Ala Lys Arg Leu Ala Ala
                675                 680                 685

Arg Gly Ile Lys Ile Arg Pro Gly Thr Val Ile Ser Tyr Ile Val Leu
                690                 695                 700

Lys Gly Pro Gly Arg Val Gly Asp Arg Ala Ile Pro Phe Asp Glu Phe
705                 710                 715                 720
```

```
Asp Pro Ala Lys His Arg Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Ala Gly Leu Gly Ala Trp
            755                 760                 765

Leu Lys Pro Lys Thr Gly Ser
            770                 775

<210> SEQ ID NO 25
<211> LENGTH: 774
<212> TYPE: PRT
<213> ORGANISM: Artificial sequence
<220> FEATURE:
<223> OTHER INFORMATION: Chimeric sequence

<400> SEQUENCE: 25

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
            35                  40                  45

Asp Glu Val Lys Lys Ile Thr Ala Glu Arg His Gly Lys Ile Val Arg
        50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
            85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
            115                 120                 125

Met Glu Gly Asn Glu Glu Leu Thr Phe Leu Ala Val Asp Ile Glu Thr
        130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
            165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
            195                 200                 205

Tyr Asn Gly Asp Asn Phe Asp Phe Pro Tyr Leu Leu Lys Arg Ala Glu
        210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
            245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
            275                 280                 285

Lys Val Tyr Ala His Glu Ile Ala Glu Ala Trp Glu Thr Gly Lys Gly
        290                 295                 300
```

```
Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
                355                 360                 365

Pro Asn Lys Pro Asp Glu Lys Glu Leu Ala Arg Arg Gln Ser Tyr
            370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Phe Asp Glu Phe
705                 710                 715                 720
```

```
Asp Pro Thr Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
            755                 760                 765

Leu Lys Pro Lys Gly Thr
            770
```

<210> SEQ ID NO 26
<211> LENGTH: 774
<212> TYPE: PRT
<213> ORGANISM: Artificial sequence
<220> FEATURE:
<223> OTHER INFORMATION: Chimeric sequence

<400> SEQUENCE: 26

```
Met Ile Ile Asp Ala Asp Tyr Ile Thr Glu Asp Gly Lys Pro Ile Ile
 1               5                  10                  15

Arg Ile Phe Lys Lys Glu Lys Gly Glu Phe Lys Val Glu Tyr Asp Arg
                20                  25                  30

Thr Phe Arg Pro Tyr Ile Tyr Ala Leu Leu Lys Asp Asp Ser Ala Ile
            35                  40                  45

Asp Glu Val Lys Lys Ile Thr Ala Glu Arg His Gly Lys Ile Val Arg
 50                  55                  60

Ile Thr Glu Val Glu Lys Val Gln Lys Lys Phe Leu Gly Arg Pro Ile
 65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
                100                 105                 110

Asp Ile Pro Phe Ala Lys Arg Tyr Leu Ile Asp Lys Gly Leu Thr Pro
            115                 120                 125

Met Glu Gly Asn Glu Glu Leu Thr Phe Leu Ala Val Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Ser Ser Glu Arg Glu Met Ile Lys
            180                 185                 190

Arg Leu Val Lys Val Ile Arg Glu Lys Asp Pro Asp Val Ile Ile Thr
            195                 200                 205

Tyr Asn Gly Asp Asn Phe Asp Phe Pro Tyr Leu Leu Lys Arg Ala Glu
210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
        275                 280                 285

Lys Val Tyr Ala His Glu Ile Ala Glu Ala Trp Glu Thr Gly Lys Gly
    290                 295                 300
```

```
Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
            325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Gln Ser Tyr
370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Arg Tyr Ala Val Ile Asp Glu Glu Gly Lys Val Ile Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Thr Ile Leu Lys His Gly Asp Val Glu Glu Ala Val
625                 630                 635                 640

Arg Ile Val Lys Glu Val Ile Gln Lys Leu Ala Asn Tyr Glu Ile Pro
                645                 650                 655

Pro Glu Lys Leu Ala Ile Tyr Glu Gln Ile Thr Arg Pro Leu His Glu
            660                 665                 670

Tyr Lys Ala Ile Gly Pro His Val Ala Val Ala Lys Lys Leu Ala Ala
            675                 680                 685

Lys Gly Val Lys Ile Lys Pro Gly Met Val Ile Gly Tyr Ile Val Leu
            690                 695                 700

Arg Gly Asp Gly Pro Ile Ser Asn Arg Ala Ile Leu Ala Glu Glu Tyr
705                 710                 715                 720

Asp Pro Lys Lys His Lys Tyr Asp Ala Glu Tyr Tyr Ile Glu Asn Gln
```

```
                          725                 730                 735
Val Leu Pro Ala Val Leu Arg Ile Leu Glu Gly Phe Gly Tyr Arg Lys
                    740                 745                 750

Glu Asp Leu Arg Tyr Gln Lys Thr Arg Gln Val Gly Leu Thr Ser Trp
                755                 760                 765

Leu Asn Ile Lys Lys Ser
            770

<210> SEQ ID NO 27
<211> LENGTH: 777
<212> TYPE: PRT
<213> ORGANISM: Artificial sequence
<220> FEATURE:
<223> OTHER INFORMATION: Chimeric sequence

<400> SEQUENCE: 27

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
    50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Ala Thr Tyr
```

```
              305                 310                 315                 320
        Glu Leu Gly Lys Glu Phe Leu Pro Met Glu Ile Gln Leu Ser Arg Leu
                        325                 330                 335
        Val Gly Gln Pro Leu Trp Asp Val Ser Arg Ser Thr Gly Asn Leu
                        340                 345                 350
        Val Glu Trp Phe Leu Arg Lys Ala Tyr Glu Arg Asn Glu Val Ala
                        355                 360                 365
        Pro Asn Lys Pro Ser Glu Glu Tyr Gln Arg Arg Leu Arg Glu Ser
                        370                 375                 380
        Tyr Thr Gly Gly Phe Val Lys Glu Pro Glu Lys Gly Leu Trp Glu Asn
        385                 390                 395                 400
        Ile Val Tyr Leu Asp Phe Arg Ala Leu Tyr Pro Ser Ile Ile Ile Thr
                        405                 410                 415
        His Asn Val Ser Pro Asp Thr Leu Asn Leu Glu Gly Cys Lys Asn Tyr
                        420                 425                 430
        Asp Ile Ala Pro Gln Val Gly His Lys Phe Cys Lys Asp Ile Pro Gly
                        435                 440                 445
        Phe Ile Pro Ser Leu Leu Gly His Leu Leu Glu Glu Arg Gln Lys Ile
                        450                 455                 460
        Lys Thr Lys Met Lys Glu Thr Gln Asp Pro Ile Glu Lys Ile Leu Leu
        465                 470                 475                 480
        Asp Tyr Arg Gln Lys Ala Ile Lys Leu Leu Ala Asn Ser Phe Tyr Gly
                        485                 490                 495
        Tyr Tyr Gly Tyr Ala Lys Ala Arg Trp Tyr Cys Lys Glu Cys Ala Glu
                        500                 505                 510
        Ser Val Thr Ala Trp Gly Arg Lys Tyr Ile Glu Leu Val Trp Lys Glu
                        515                 520                 525
        Leu Glu Glu Lys Phe Gly Phe Lys Val Leu Tyr Ile Asp Thr Asp Gly
                        530                 535                 540
        Leu Tyr Ala Thr Ile Pro Gly Gly Ser Glu Glu Ile Lys Lys Lys
        545                 550                 555                 560
        Ala Leu Glu Phe Val Lys Tyr Ile Asn Ser Lys Leu Pro Gly Leu Leu
                        565                 570                 575
        Glu Leu Glu Tyr Glu Gly Phe Tyr Val Arg Gly Phe Phe Val Thr Lys
                        580                 585                 590
        Lys Lys Tyr Ala Leu Ile Asp Glu Glu Gly Lys Ile Ile Thr Arg Gly
                        595                 600                 605
        Leu Glu Ile Val Arg Arg Asp Trp Ser Glu Ile Ala Lys Glu Thr Gln
                        610                 615                 620
        Ala Lys Val Leu Glu Ala Ile Leu Lys His Gly Asn Val Glu Glu Ala
        625                 630                 635                 640
        Val Lys Ile Val Lys Glu Val Thr Glu Lys Leu Ser Lys Tyr Glu Ile
                        645                 650                 655
        Pro Pro Glu Lys Leu Val Ile Tyr Glu Gln Ile Thr Arg Pro Leu His
                        660                 665                 670
        Glu Tyr Lys Ala Ile Gly Pro His Val Ala Val Ala Lys Arg Leu Ala
                        675                 680                 685
        Ala Arg Gly Val Lys Val Arg Pro Gly Met Val Ile Gly Tyr Ile Val
                        690                 695                 700
        Leu Arg Gly Asp Gly Pro Ile Ser Lys Arg Ala Ile Leu Ala Glu Glu
        705                 710                 715                 720
        Phe Asp Leu Arg Lys His Lys Tyr Asp Ala Glu Tyr Tyr Ile Glu Asn
                        725                 730                 735
```

-continued

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
            755                 760                 765

Trp Leu Asn Ile Lys Lys Lys Gly Ser
            770                 775

<210> SEQ ID NO 28
<211> LENGTH: 776
<212> TYPE: PRT
<213> ORGANISM: Artificial sequence
<220> FEATURE:
<223> OTHER INFORMATION: Chimeric sequence

<400> SEQUENCE: 28

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
            35                  40                  45

Asp Glu Val Lys Lys Ile Thr Ala Glu Arg His Gly Lys Ile Val Arg
        50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
            115                 120                 125

Met Glu Gly Asn Glu Glu Leu Thr Phe Leu Ala Val Asp Ile Glu Thr
        130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
            195                 200                 205

Tyr Asn Gly Asp Asn Phe Asp Phe Pro Tyr Leu Leu Lys Arg Ala Glu
        210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
            275                 280                 285

Lys Val Tyr Ala His Glu Ile Ala Glu Ala Trp Glu Thr Gly Lys Gly
        290                 295                 300

Leu Glu Arg Val Ala Lys Tyr Ser Met Glu Asp Ala Lys Ala Thr Tyr
305                 310                 315                 320

```
Glu Leu Gly Lys Glu Phe Leu Pro Met Glu Ile Gln Leu Ser Arg Leu
                325                 330                 335

Val Gly Gln Pro Leu Trp Asp Val Ser Arg Ser Thr Gly Asn Leu
            340                 345                 350

Val Glu Trp Phe Leu Leu Arg Lys Ala Tyr Glu Arg Asn Glu Val Ala
            355                 360                 365

Pro Asn Lys Pro Ser Glu Glu Glu Tyr Gln Arg Arg Leu Arg Glu Ser
370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
            450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Arg Arg Gly Phe Phe Val Thr Lys
            580                 585                 590

Lys Lys Tyr Ala Val Ile Asp Glu Glu Asp Lys Ile Thr Thr Arg Gly
            595                 600                 605

Leu Glu Ile Val Arg Arg Asp Trp Ser Glu Ile Ala Lys Glu Thr Gln
            610                 615                 620

Ala Arg Val Leu Glu Ala Ile Leu Lys His Gly Asp Val Glu Glu Ala
625                 630                 635                 640

Val Arg Ile Val Lys Glu Val Thr Glu Lys Leu Ser Arg Tyr Glu Val
                645                 650                 655

Pro Pro Glu Lys Leu Val Ile Tyr Glu Gln Ile Thr Arg Asn Leu Arg
            660                 665                 670

Asp Tyr Arg Ala Thr Gly Pro His Val Ala Val Ala Lys Arg Leu Ala
            675                 680                 685

Ala Arg Gly Ile Lys Ile Arg Pro Gly Thr Val Ile Ser Tyr Ile Val
690                 695                 700

Leu Lys Gly Pro Gly Arg Val Gly Asp Arg Ala Ile Pro Phe Asp Glu
705                 710                 715                 720

Phe Asp Pro Ala Lys His Arg Tyr Asp Ala Glu Tyr Tyr Ile Glu Asn
                725                 730                 735
```

```
Gln Val Leu Pro Ala Val Glu Arg Ile Leu Arg Ala Phe Gly Tyr Arg
            740                 745                 750

Lys Glu Asp Leu Arg Tyr Gln Lys Thr Lys Gln Ala Gly Leu Gly Ala
        755                 760                 765

Trp Leu Lys Pro Lys Thr Gly Ser
    770                 775

<210> SEQ ID NO 29
<211> LENGTH: 775
<212> TYPE: PRT
<213> ORGANISM: Artificial sequence
<220> FEATURE:
<223> OTHER INFORMATION: Chimeric sequence

<400> SEQUENCE: 29

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
            85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Gly Ala Lys Val Ile Thr Trp Lys Ser Ile
            165                 170                 175

Asp Leu Pro Tyr Val Glu Val Val Ser Ser Glu Arg Glu Met Ile Lys
        180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
        275                 280                 285

Lys Val Tyr Ala His Glu Ile Ala Glu Ala Trp Glu Thr Gly Lys Gly
        290                 295                 300

Leu Glu Arg Val Ala Lys Tyr Ser Met Glu Asp Ala Lys Ala Thr Tyr
305                 310                 315                 320
```

```
Glu Leu Gly Lys Glu Phe Leu Pro Met Glu Ile Gln Leu Ser Arg Leu
            325                 330                 335

Val Gly Gln Pro Leu Trp Asp Val Ser Arg Ser Thr Gly Asn Leu
        340                 345                 350

Val Glu Trp Phe Leu Leu Arg Lys Ala Tyr Glu Arg Asn Glu Val Ala
            355                 360                 365

Pro Asn Lys Pro Ser Glu Glu Tyr Gln Arg Arg Leu Arg Glu Ser
        370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
        450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Val Ile Asp Glu Glu Gly Lys Ile Thr Thr Arg Gly
        595                 600                 605

Leu Glu Ile Val Arg Arg Asp Trp Ser Glu Ile Ala Lys Glu Thr Gln
        610                 615                 620

Ala Arg Val Leu Glu Ala Leu Leu Lys Asp Gly Asp Val Glu Lys Ala
625                 630                 635                 640

Val Arg Ile Val Lys Glu Val Thr Glu Lys Leu Ser Lys Tyr Glu Val
                645                 650                 655

Pro Pro Glu Lys Leu Val Ile His Glu Gln Ile Thr Arg Asp Leu Lys
            660                 665                 670

Asp Tyr Lys Ala Thr Gly Pro His Val Ala Val Ala Lys Arg Leu Ala
        675                 680                 685

Ala Arg Gly Val Lys Ile Arg Pro Gly Thr Val Ile Ser Tyr Ile Val
        690                 695                 700

Leu Lys Gly Ser Gly Arg Ile Gly Asp Arg Ala Ile Pro Phe Asp Glu
705                 710                 715                 720

Phe Asp Pro Thr Lys His Lys Tyr Asp Ala Glu Tyr Tyr Ile Glu Asn
                725                 730                 735

Gln Val Leu Pro Ala Val Glu Arg Ile Leu Arg Ala Phe Gly Tyr Arg
```

```
                  740                 745                 750
Lys Glu Asp Leu Arg Tyr Gln Lys Thr Arg Gln Val Gly Leu Ser Ala
            755                 760                 765

Trp Leu Lys Pro Lys Gly Thr
        770                 775

<210> SEQ ID NO 30
<211> LENGTH: 777
<212> TYPE: PRT
<213> ORGANISM: Artificial sequence
<220> FEATURE:
<223> OTHER INFORMATION: Chimeric sequence

<400> SEQUENCE: 30

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
```

```
                325                 330                 335
Val Gly Gln Pro Leu Trp Asp Val Ser Arg Ser Thr Gly Asn Leu
            340                 345                 350
Val Glu Trp Tyr Leu Leu Arg Lys Ala Tyr Glu Arg Asn Glu Leu Ala
            355                 360                 365
Pro Asn Lys Pro Asp Glu Arg Glu Tyr Glu Arg Arg Leu Arg Glu Ser
    370                 375                 380
Tyr Ala Gly Gly Tyr Val Lys Glu Pro Glu Lys Gly Leu Trp Glu Gly
385                 390                 395                 400
Leu Val Ser Leu Asp Phe Arg Ser Leu Tyr Pro Ser Ile Ile Ile Thr
                405                 410                 415
His Asn Val Ser Pro Asp Thr Leu Asn Arg Glu Gly Cys Arg Glu Tyr
            420                 425                 430
Asp Val Ala Pro Glu Val Gly His Lys Phe Cys Lys Asp Phe Pro Gly
            435                 440                 445
Phe Ile Pro Ser Leu Leu Lys Arg Leu Leu Asp Glu Arg Gln Glu Ile
    450                 455                 460
Lys Arg Lys Met Lys Ala Ser Lys Asp Pro Ile Glu Lys Lys Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Arg Lys Glu
            515                 520                 525
Leu Glu Glu Lys Phe Gly Phe Lys Val Leu Tyr Ile Asp Thr Asp Gly
        530                 535                 540
Leu Tyr Ala Thr Ile Pro Gly Ala Lys Pro Glu Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Val Arg Gly Phe Phe Val Thr Lys
            580                 585                 590
Lys Lys Tyr Ala Leu Ile Asp Glu Glu Gly Lys Ile Ile Thr Arg Gly
        595                 600                 605
Leu Glu Ile Val Arg Arg Asp Trp Ser Glu Ile Ala Lys Glu Thr Gln
    610                 615                 620
Ala Lys Val Leu Glu Ala Ile Leu Lys His Gly Asn Val Glu Glu Ala
625                 630                 635                 640
Val Lys Ile Val Lys Glu Val Thr Glu Lys Leu Ser Lys Tyr Glu Ile
                645                 650                 655
Pro Pro Glu Lys Leu Val Ile Tyr Glu Gln Ile Thr Arg Pro Leu His
            660                 665                 670
Glu Tyr Lys Ala Ile Gly Pro His Val Ala Val Ala Lys Arg Leu Ala
        675                 680                 685
Ala Arg Gly Val Lys Val Arg Pro Gly Met Val Ile Gly Tyr Ile Val
        690                 695                 700
Leu Arg Gly Asp Gly Pro Ile Ser Lys Arg Ala Ile Leu Ala Glu Glu
705                 710                 715                 720
Phe Asp Leu Arg Lys His Lys Tyr Asp Ala Glu Tyr Tyr Ile Glu Asn
                725                 730                 735
Gln Val Leu Pro Ala Val Leu Arg Ile Leu Glu Ala Phe Gly Tyr Arg
            740                 745                 750
```

```
Lys Glu Asp Leu Arg Trp Gln Lys Thr Lys Gln Thr Gly Leu Thr Ala
        755                 760                 765

Trp Leu Asn Ile Lys Lys Lys Gly Ser
        770                 775

<210> SEQ ID NO 31
<211> LENGTH: 774
<212> TYPE: PRT
<213> ORGANISM: Artificial sequence
<220> FEATURE:
<223> OTHER INFORMATION: Chimeric sequence

<400> SEQUENCE: 31

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335
```

```
Val Gly Gln Pro Leu Trp Asp Val Ser Arg Ser Thr Gly Asn Leu
            340                 345                 350

Val Glu Trp Tyr Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
        370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Glu Ile
        450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
            485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Ala Arg Gly Phe Phe Val Thr Lys
            580                 585                 590

Lys Lys Tyr Ala Leu Ile Asp Glu Glu Gly Lys Ile Val Thr Arg Gly
            595                 600                 605

Leu Glu Ile Val Arg Arg Asp Trp Ser Glu Ile Ala Lys Glu Thr Gln
            610                 615                 620

Ala Lys Val Leu Glu Ala Ile Leu Lys His Gly Asn Val Asp Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu Ser
            660                 665                 670

Glu Tyr Lys Ala Ile Gly Pro His Val Ala Val Ala Lys Arg Leu Ala
            675                 680                 685

Ala Lys Gly Val Lys Val Lys Pro Gly Met Val Ile Gly Tyr Ile Val
            690                 695                 700

Leu Arg Gly Asp Gly Pro Ile Ser Lys Arg Ala Ile Ala Ile Glu Glu
705                 710                 715                 720

Phe Asp Pro Lys Lys His Lys Tyr Asp Ala Glu Tyr Tyr Ile Glu Asn
                725                 730                 735

Gln Val Leu Pro Ala Val Glu Arg Ile Leu Arg Ala Phe Gly Tyr Arg
            740                 745                 750
```

-continued

Lys Glu Asp Leu Lys Tyr Gln Lys Thr Lys Gln Val Gly Leu Gly Ala
            755                 760                 765
Trp Leu Lys Phe Gly Ser
        770

<210> SEQ ID NO 32
<211> LENGTH: 776
<212> TYPE: PRT
<213> ORGANISM: Artificial sequence
<220> FEATURE:
<223> OTHER INFORMATION: Chimeric sequence

<400> SEQUENCE: 32

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

-continued

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
            355                 360             365

Pro Asn Lys Pro Asp Glu Arg Glu Tyr Glu Arg Arg Leu Arg Glu Ser
        370                 375             380

Tyr Ala Gly Gly Tyr Val Lys Glu Pro Glu Lys Gly Leu Trp Glu Gly
385                     390             395                 400

Leu Val Ser Leu Asp Phe Arg Ser Leu Tyr Pro Ser Ile Ile Ile Thr
                405                 410             415

His Asn Val Ser Pro Asp Thr Leu Asn Arg Glu Gly Cys Arg Glu Tyr
            420                 425             430

Asp Val Ala Pro Glu Val Gly His Lys Phe Cys Lys Asp Phe Pro Gly
        435                 440             445

Phe Ile Pro Ser Leu Leu Lys Arg Leu Leu Asp Glu Arg Gln Glu Ile
        450                 455             460

Lys Arg Lys Met Lys Ala Ser Lys Asp Pro Ile Glu Lys Lys Met Leu
465                 470             475                 480

Asp Tyr Arg Gln Arg Ala Ile Lys Ile Leu Ala Asn Ser Tyr Tyr Gly
            485                 490             495

Tyr Tyr Gly Tyr Ala Lys Ala Arg Trp Tyr Cys Lys Glu Cys Ala Glu
            500                 505             510

Ser Val Thr Ala Trp Gly Arg Glu Tyr Ile Glu Phe Val Arg Lys Glu
            515                 520             525

Leu Glu Glu Lys Phe Gly Phe Lys Val Leu Tyr Ile Asp Thr Asp Gly
530                 535             540

Leu Tyr Ala Thr Ile Pro Gly Ala Lys Pro Glu Glu Ile Lys Lys Lys
545                 550             555             560

Ala Leu Glu Phe Val Asp Tyr Ile Asn Ala Lys Leu Pro Gly Leu Leu
                565                 570             575

Glu Leu Glu Tyr Glu Gly Phe Tyr Arg Arg Gly Phe Phe Val Thr Lys
            580                 585             590

Lys Lys Tyr Ala Val Ile Asp Glu Glu Asp Lys Ile Thr Thr Arg Gly
            595                 600             605

Leu Glu Ile Val Arg Arg Asp Trp Ser Glu Ile Ala Lys Glu Thr Gln
        610                 615             620

Ala Arg Val Leu Glu Ala Ile Leu Lys His Gly Asp Val Glu Glu Ala
625                 630             635                 640

Val Arg Ile Val Lys Glu Val Thr Glu Lys Leu Ser Arg Tyr Glu Val
            645                 650             655

Pro Pro Glu Lys Leu Val Ile Tyr Glu Gln Ile Thr Arg Asn Leu Arg
            660                 665             670

Asp Tyr Arg Ala Thr Gly Pro His Val Ala Val Ala Lys Arg Leu Ala
        675                 680             685

Ala Arg Gly Ile Lys Ile Arg Pro Gly Thr Val Ile Ser Tyr Ile Val
            690                 695             700

Leu Lys Gly Pro Gly Arg Val Gly Asp Arg Ala Ile Pro Phe Asp Glu
705                 710             715                 720

Phe Asp Pro Ala Lys His Arg Tyr Asp Ala Glu Tyr Tyr Ile Glu Asn
                725                 730             735

Gln Val Leu Pro Ala Val Glu Arg Ile Leu Arg Ala Phe Gly Tyr Arg
            740                 745             750

Lys Glu Asp Leu Arg Tyr Gln Lys Thr Lys Gln Ala Gly Leu Gly Ala

-continued

```
            755                 760                 765

Trp Leu Lys Pro Lys Thr Gly Ser
    770                 775

<210> SEQ ID NO 33
<211> LENGTH: 775
<212> TYPE: PRT
<213> ORGANISM: Artificial sequence
<220> FEATURE:
<223> OTHER INFORMATION: Chimeric sequence

<400> SEQUENCE: 33

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
```

-continued

```
                340             345             350
Val Glu Trp Tyr Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
        370                 375             380

Tyr Ala Gly Gly Tyr Val Lys Glu Pro Glu Lys Gly Leu Trp Glu Gly
385                     390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
        450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
        530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
        610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765
```

```
Trp Leu Asn Ile Lys Lys Ser
        770             775

<210> SEQ ID NO 34
<211> LENGTH: 776
<212> TYPE: PRT
<213> ORGANISM: Artificial sequence
<220> FEATURE:
<223> OTHER INFORMATION: Chimeric sequence

<400> SEQUENCE: 34

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350
```

```
Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Asn Cys Lys Glu Tyr
                420                 425                 430

Asp Val Ala Pro Gln Val Gly His Arg Phe Cys Lys Asp Phe Pro Gly
            435                 440                 445

Phe Ile Pro Ser Leu Leu Gly Asn Leu Leu Glu Glu Arg Gln Lys Ile
        450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Gln Tyr Ile Asp Leu Val Arg Arg Glu
        515                 520                 525

Leu Glu Ser Arg Gly Phe Lys Val Leu Tyr Ile Asp Thr Asp Gly Leu
        530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Leu Ile Asp Glu Glu Gly Lys Ile Ile Thr Arg Gly Leu
        595                 600                 605

Glu Ile Val Arg Arg Asp Trp Ser Glu Ile Ala Lys Glu Thr Gln Ala
    610                 615                 620

Lys Val Leu Glu Ala Ile Leu Lys His Gly Asn Val Glu Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu His Glu
            660                 665                 670

Tyr Lys Ala Ile Gly Pro His Val Ala Val Ala Lys Arg Leu Ala Ala
        675                 680                 685

Arg Gly Val Lys Val Arg Pro Gly Met Val Ile Gly Tyr Ile Val Leu
690                 695                 700

Arg Gly Asp Gly Pro Ile Ser Lys Arg Ala Ile Leu Ala Glu Glu Phe
705                 710                 715                 720

Asp Leu Arg Lys His Lys Tyr Asp Ala Glu Tyr Tyr Ile Glu Asn Gln
                725                 730                 735

Val Leu Pro Ala Val Leu Arg Ile Leu Glu Ala Phe Gly Tyr Arg Lys
            740                 745                 750

Glu Asp Leu Arg Trp Gln Lys Thr Lys Gln Thr Gly Leu Thr Ala Trp
        755                 760                 765
```

```
Leu Asn Ile Lys Lys Lys Gly Ser
    770             775

<210> SEQ ID NO 35
<211> LENGTH: 773
<212> TYPE: PRT
<213> ORGANISM: Artificial sequence
<220> FEATURE:
<223> OTHER INFORMATION: Chimeric sequence

<400> SEQUENCE: 35

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350
```

```
Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Asn Cys Lys Glu Tyr
            420                 425                 430

Asp Val Ala Pro Gln Val Gly His Arg Phe Cys Lys Asp Phe Pro Gly
        435                 440                 445

Phe Ile Pro Ser Leu Leu Gly Asn Leu Leu Glu Glu Arg Gln Lys Ile
    450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Asp Leu Val Arg Arg Glu
        515                 520                 525

Leu Glu Ser Arg Gly Phe Lys Val Leu Tyr Ile Asp Thr Asp Gly Leu
    530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Ala Arg Gly Phe Phe Val Thr Lys Lys
            580                 585                 590

Lys Tyr Ala Leu Ile Asp Glu Glu Gly Lys Ile Val Thr Arg Gly Leu
        595                 600                 605

Glu Ile Val Arg Arg Asp Trp Ser Glu Ile Ala Lys Glu Thr Gln Ala
    610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
            660                 665                 670

Tyr Lys Ala Ile Gly Pro His Val Ala Val Ala Lys Arg Leu Ala Ala
        675                 680                 685

Lys Gly Val Lys Val Lys Pro Gly Met Val Ile Gly Tyr Ile Val Leu
    690                 695                 700

Arg Gly Asp Gly Pro Ile Ser Lys Arg Ala Ile Ala Ile Glu Glu Phe
705                 710                 715                 720

Asp Pro Lys Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Lys Tyr Gln Lys Thr Lys Gln Val Gly Leu Gly Ala Trp
        755                 760                 765

Leu Lys Phe Gly Ser
```

770

<210> SEQ ID NO 36
<211> LENGTH: 775
<212> TYPE: PRT
<213> ORGANISM: Artificial sequence
<220> FEATURE:
<223> OTHER INFORMATION: Chimeric sequence

<400> SEQUENCE: 36

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
```

```
                355                 360                 365
Pro Asn Lys Pro Asp Glu Arg Glu Tyr Glu Arg Arg Leu Arg Glu Ser
370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Asn Cys Lys Glu Tyr
                420                 425                 430

Asp Val Ala Pro Gln Val Gly His Arg Phe Cys Lys Asp Phe Pro Gly
                435                 440                 445

Phe Ile Pro Ser Leu Leu Gly Asn Leu Leu Glu Glu Arg Gln Lys Ile
                450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Gln Tyr Ile Asp Leu Val Arg Arg Glu
                515                 520                 525

Leu Glu Ser Arg Gly Phe Lys Val Leu Tyr Ile Asp Thr Asp Gly Leu
                530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Arg Arg Gly Phe Phe Val Thr Lys Lys
                580                 585                 590

Lys Tyr Ala Val Ile Asp Glu Glu Asp Lys Ile Thr Thr Arg Gly Leu
                595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg Tyr Glu Val Pro
                645                 650                 655

Pro Glu Lys Leu Val Ile Tyr Glu Gln Ile Thr Arg Asn Leu Arg Asp
                660                 665                 670

Tyr Arg Ala Thr Gly Pro His Val Ala Val Ala Lys Arg Leu Ala Ala
                675                 680                 685

Arg Gly Ile Lys Ile Arg Pro Gly Thr Val Ile Ser Tyr Ile Val Leu
                690                 695                 700

Lys Gly Pro Gly Arg Val Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Lys Gln Ala Gly Leu Gly Ala Trp
                755                 760                 765

Leu Lys Pro Lys Thr Gly Ser
770                 775
```

<210> SEQ ID NO 37
<211> LENGTH: 774
<212> TYPE: PRT
<213> ORGANISM: Artificial sequence
<220> FEATURE:
<223> OTHER INFORMATION: Chimeric sequence

<400> SEQUENCE: 37

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365
```

```
Pro Asn Lys Pro Asp Glu Arg Glu Tyr Glu Arg Arg Leu Arg Glu Ser
    370                 375                 380
Tyr Glu Gly Gly Tyr Val Lys Glu Pro Glu Lys Gly Leu Trp Glu Gly
385                 390                 395                 400
Ile Val Ser Leu Asp Phe Arg Ser Leu Tyr Pro Ser Ile Ile Ile Thr
                405                 410                 415
His Asn Val Ser Pro Asp Thr Leu Asn Arg Glu Asn Cys Lys Glu Tyr
                420                 425                 430
Asp Val Ala Pro Gln Val Gly His Arg Phe Cys Lys Asp Phe Pro Gly
            435                 440                 445
Phe Ile Pro Ser Leu Leu Gly Asn Leu Leu Glu Arg Gln Lys Ile
450                 455                 460
Lys Lys Arg Met Lys Glu Ser Lys Asp Pro Val Glu Lys Lys Leu Leu
465                 470                 475                 480
Asp Tyr Arg Gln Arg Ala Ile Lys Ile Leu Ala Asn Ser Tyr Tyr Gly
            485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Gln Tyr Ile Asp Leu Val Arg Arg Glu
            515                 520                 525
Leu Glu Ser Arg Gly Phe Lys Val Leu Tyr Ile Asp Thr Asp Gly Leu
530                 535                 540
Tyr Ala Thr Ile Pro Gly Ala Lys His Glu Glu Ile Lys Glu Lys Ala
545                 550                 555                 560
Leu Lys Phe Val Glu Tyr Ile Asn Ser Lys Leu Pro Gly Leu Leu Glu
                565                 570                 575
Leu Glu Tyr Glu Gly Phe Tyr Lys Arg Gly Phe Phe Val Thr Lys Lys
            580                 585                 590
Arg Tyr Ala Val Ile Asp Glu Glu Gly Lys Val Ile Thr Arg Gly Leu
            595                 600                 605
Glu Ile Val Arg Arg Asp Trp Ser Glu Ile Ala Lys Glu Thr Gln Ala
        610                 615                 620
Arg Val Leu Glu Thr Ile Leu Lys His Gly Asp Val Glu Glu Ala Val
625                 630                 635                 640
Arg Ile Val Lys Glu Val Ile Gln Lys Leu Ala Asn Tyr Glu Ile Pro
                645                 650                 655
Pro Glu Lys Leu Ala Ile Tyr Glu Gln Ile Thr Arg Pro Leu His Glu
            660                 665                 670
Tyr Lys Ala Ile Gly Pro His Val Ala Val Ala Lys Lys Leu Ala Ala
            675                 680                 685
Lys Gly Val Lys Ile Lys Pro Gly Met Val Ile Gly Tyr Ile Val Leu
690                 695                 700
Arg Gly Asp Gly Pro Ile Ser Asn Arg Ala Ile Leu Ala Glu Glu Tyr
705                 710                 715                 720
Asp Pro Lys Lys His Lys Tyr Asp Ala Glu Tyr Tyr Ile Glu Asn Gln
                725                 730                 735
Val Leu Pro Ala Val Leu Arg Ile Leu Glu Gly Phe Gly Tyr Arg Lys
            740                 745                 750
Glu Asp Leu Arg Tyr Gln Lys Thr Arg Gln Val Gly Leu Thr Ser Trp
            755                 760                 765
Leu Asn Ile Lys Lys Ser
    770
```

<210> SEQ ID NO 38
<211> LENGTH: 776
<212> TYPE: PRT
<213> ORGANISM: Artificial sequence
<220> FEATURE:
<223> OTHER INFORMATION: Chimeric sequence

<400> SEQUENCE: 38

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365
```

```
Pro Asn Lys Pro Asp Glu Arg Glu Leu Ala Arg Arg Ala Glu Ser Tyr
370                 375                 380
Ala Gly Gly Tyr Val Lys Glu Pro Glu Lys Gly Leu Trp Glu Asn Ile
385                 390                 395                 400
Val Tyr Leu Asp Tyr Lys Ser Leu Tyr Pro Ser Ile Ile Thr His
            405                 410                 415
Asn Val Ser Pro Asp Thr Leu Asn Arg Glu Gly Cys Arg Glu Tyr Asp
            420                 425                 430
Val Ala Pro Gln Val Gly His Arg Phe Cys Lys Asp Phe Pro Gly Phe
            435                 440                 445
Ile Pro Ser Leu Leu Gly Asp Leu Leu Glu Glu Arg Gln Lys Val Lys
450                 455                 460
Lys Lys Met Lys Ala Thr Val Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Asn Ala Arg Trp Tyr Cys Arg Glu Cys Ala Glu Ser
            500                 505                 510
Val Thr Ala Trp Gly Arg Gln Tyr Ile Glu Thr Thr Met Arg Glu Ile
            515                 520                 525
Glu Glu Lys Phe Gly Phe Lys Val Leu Tyr Ala Asp Thr Asp Gly Phe
530                 535                 540
Phe Ala Thr Ile Pro Gly Ala Asp Ala Glu Thr Val Lys Lys Lys Thr
545                 550                 555                 560
Lys Glu Phe Leu Asn Tyr Ile Asn Pro Arg Leu Pro Gly Leu Leu Glu
                565                 570                 575
Leu Glu Tyr Glu Gly Phe Tyr Val Arg Gly Phe Phe Val Thr Lys Lys
            580                 585                 590
Lys Tyr Ala Leu Ile Asp Glu Glu Gly Lys Ile Ile Thr Arg Gly Leu
            595                 600                 605
Glu Ile Val Arg Arg Asp Trp Ser Glu Ile Ala Lys Glu Thr Gln Ala
610                 615                 620
Lys Val Leu Glu Ala Ile Leu Lys His Gly Asn Val Glu Glu Ala Val
625                 630                 635                 640
Lys Ile Val Lys Glu Val Thr Glu Lys Leu Ser Lys Tyr Glu Ile Pro
                645                 650                 655
Pro Glu Lys Leu Val Ile Tyr Glu Gln Ile Thr Arg Pro Leu His Glu
            660                 665                 670
Tyr Lys Ala Ile Gly Pro His Val Ala Val Ala Lys Arg Leu Ala Ala
            675                 680                 685
Arg Gly Val Lys Val Arg Pro Gly Met Val Ile Gly Tyr Ile Val Leu
690                 695                 700
Arg Gly Asp Gly Pro Ile Ser Lys Arg Ala Ile Leu Ala Glu Glu Phe
705                 710                 715                 720
Asp Leu Arg Lys His Lys Tyr Asp Ala Glu Tyr Tyr Ile Glu Asn Gln
                725                 730                 735
Val Leu Pro Ala Val Leu Arg Ile Leu Glu Ala Phe Gly Tyr Arg Lys
            740                 745                 750
Glu Asp Leu Arg Trp Gln Lys Thr Lys Gln Thr Gly Leu Thr Ala Trp
            755                 760                 765
Leu Asn Ile Lys Lys Lys Gly Ser
770                 775
```

```
<210> SEQ ID NO 39
<211> LENGTH: 773
<212> TYPE: PRT
<213> ORGANISM: Artificial sequence
<220> FEATURE:
<223> OTHER INFORMATION: Chimeric sequence

<400> SEQUENCE: 39

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Ala Glu Ser Tyr
```

```
                370             375             380
Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Thr His
                405                 410                 415

Asn Val Ser Pro Asp Thr Leu Asn Arg Glu Gly Cys Arg Glu Tyr Asp
                420                 425                 430

Val Ala Pro Gln Val Gly His Arg Phe Cys Lys Asp Phe Pro Gly Phe
                435                 440                 445

Ile Pro Ser Leu Leu Gly Asp Leu Leu Glu Glu Arg Gln Lys Val Lys
                450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
                500                 505                 510

Val Thr Ala Trp Gly Arg Gln Tyr Ile Glu Thr Thr Met Arg Glu Ile
                515                 520                 525

Glu Glu Lys Phe Gly Phe Lys Val Leu Tyr Ala Asp Thr Asp Gly Phe
                530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Ala Arg Gly Phe Phe Val Thr Lys Lys
                580                 585                 590

Lys Tyr Ala Leu Ile Asp Glu Glu Gly Lys Ile Val Thr Arg Gly Leu
                595                 600                 605

Glu Ile Val Arg Arg Asp Trp Ser Glu Ile Ala Lys Glu Thr Gln Ala
                610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
                660                 665                 670

Tyr Lys Ala Ile Gly Pro His Val Ala Val Ala Lys Arg Leu Ala Ala
                675                 680                 685

Lys Gly Val Lys Val Lys Pro Gly Met Val Ile Gly Tyr Ile Val Leu
                690                 695                 700

Arg Gly Asp Gly Pro Ile Ser Lys Arg Ala Ile Ala Ile Glu Glu Phe
705                 710                 715                 720

Asp Pro Lys Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Lys Tyr Gln Lys Thr Lys Gln Val Gly Leu Gly Ala Trp
                755                 760                 765

Leu Lys Phe Gly Ser
    770

<210> SEQ ID NO 40
```

```
<211> LENGTH: 774
<212> TYPE: PRT
<213> ORGANISM: Artificial sequence
<220> FEATURE:
<223> OTHER INFORMATION: Chimeric sequence

<400> SEQUENCE: 40

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Ala Glu Ser Tyr
    370                 375                 380
```

```
Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
            405                 410                 415

Asn Val Ser Pro Asp Thr Leu Asn Arg Glu Gly Cys Arg Glu Tyr Asp
        420                 425                 430

Val Ala Pro Gln Val Gly His Arg Phe Cys Lys Asp Phe Pro Gly Phe
    435                 440                 445

Ile Pro Ser Leu Leu Gly Asp Leu Leu Glu Glu Arg Gln Lys Val Lys
450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
            515                 520                 525

Glu Glu Lys Phe Gly Phe Lys Val Leu Tyr Ala Asp Thr Asp Gly Phe
530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Lys Arg Gly Phe Phe Val Thr Lys Lys
            580                 585                 590

Arg Tyr Ala Val Ile Asp Glu Glu Gly Lys Val Ile Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Thr Ile Leu Lys His Gly Asp Val Glu Glu Ala Val
625                 630                 635                 640

Arg Ile Val Lys Glu Val Ile Gln Lys Leu Ala Asn Tyr Glu Ile Pro
                645                 650                 655

Pro Glu Lys Leu Ala Ile Tyr Glu Gln Ile Thr Arg Pro Leu His Glu
            660                 665                 670

Tyr Lys Ala Ile Gly Pro His Val Ala Val Ala Lys Lys Leu Ala Ala
        675                 680                 685

Lys Gly Val Lys Ile Lys Pro Gly Met Val Ile Gly Tyr Ile Val Leu
    690                 695                 700

Arg Gly Asp Gly Pro Ile Ser Asn Arg Ala Ile Leu Ala Glu Glu Tyr
705                 710                 715                 720

Asp Pro Lys Lys His Lys Tyr Asp Ala Glu Tyr Tyr Ile Glu Asn Gln
                725                 730                 735

Val Leu Pro Ala Val Leu Arg Ile Leu Glu Gly Phe Gly Tyr Arg Lys
            740                 745                 750

Glu Asp Leu Arg Tyr Gln Lys Thr Arg Gln Val Gly Leu Thr Ser Trp
        755                 760                 765

Leu Asn Ile Lys Lys Ser
    770
```

<210> SEQ ID NO 41
<211> LENGTH: 774

```
<212> TYPE: PRT
<213> ORGANISM: Artificial sequence
<220> FEATURE:
<223> OTHER INFORMATION: Chimeric sequence

<400> SEQUENCE: 41
```

| | | | | | | | | | | | | | | | |
|---|---|---|---|---|---|---|---|---|---|---|---|---|---|---|---|
| Met | Ile | Leu | Asp | Val | Asp | Tyr | Ile | Thr | Glu | Glu | Gly | Lys | Pro | Val | Ile |
| 1 | | | | 5 | | | | | 10 | | | | | 15 | |
| Arg | Leu | Phe | Lys | Lys | Glu | Asn | Gly | Lys | Phe | Lys | Ile | Glu | His | Asp | Arg |
| | | | 20 | | | | | 25 | | | | | 30 | | |
| Thr | Phe | Arg | Pro | Tyr | Ile | Tyr | Ala | Leu | Leu | Arg | Asp | Asp | Ser | Lys | Ile |
| | | 35 | | | | | 40 | | | | | 45 | | | |
| Glu | Glu | Val | Lys | Lys | Ile | Thr | Gly | Glu | Arg | His | Gly | Lys | Ile | Val | Arg |
| 50 | | | | | 55 | | | | | 60 | | | | | |
| Ile | Val | Asp | Val | Glu | Lys | Val | Glu | Lys | Lys | Phe | Leu | Gly | Lys | Pro | Ile |
| 65 | | | | | 70 | | | | | 75 | | | | | 80 |
| Thr | Val | Trp | Lys | Leu | Tyr | Leu | Glu | His | Pro | Gln | Asp | Val | Pro | Thr | Ile |
| | | | | 85 | | | | | 90 | | | | | 95 | |
| Arg | Glu | Lys | Val | Arg | Glu | His | Pro | Ala | Val | Val | Asp | Ile | Phe | Glu | Tyr |
| | | | 100 | | | | | 105 | | | | | 110 | | |
| Asp | Ile | Pro | Phe | Ala | Lys | Arg | Tyr | Leu | Ile | Asp | Lys | Gly | Leu | Ile | Pro |
| | | 115 | | | | | 120 | | | | | 125 | | | |
| Met | Glu | Gly | Glu | Glu | Glu | Leu | Lys | Ile | Leu | Ala | Phe | Asp | Ile | Glu | Thr |
| 130 | | | | | 135 | | | | | 140 | | | | | |
| Leu | Tyr | His | Glu | Gly | Glu | Glu | Phe | Gly | Lys | Gly | Pro | Ile | Ile | Met | Ile |
| 145 | | | | | 150 | | | | | 155 | | | | | 160 |
| Ser | Tyr | Ala | Asp | Glu | Asn | Glu | Ala | Lys | Val | Ile | Thr | Trp | Lys | Asn | Ile |
| | | | | 165 | | | | | 170 | | | | | 175 | |
| Asp | Leu | Pro | Tyr | Val | Glu | Val | Val | Ser | Ser | Glu | Arg | Glu | Met | Ile | Lys |
| | | | 180 | | | | | 185 | | | | | 190 | | |
| Arg | Phe | Leu | Arg | Ile | Ile | Arg | Glu | Lys | Asp | Pro | Asp | Ile | Ile | Val | Thr |
| | | 195 | | | | | 200 | | | | | 205 | | | |
| Tyr | Asn | Gly | Asp | Ser | Phe | Asp | Phe | Pro | Tyr | Leu | Ala | Lys | Arg | Ala | Glu |
| 210 | | | | | 215 | | | | | 220 | | | | | |
| Lys | Leu | Gly | Ile | Lys | Leu | Thr | Ile | Gly | Arg | Asp | Gly | Ser | Glu | Pro | Lys |
| 225 | | | | | 230 | | | | | 235 | | | | | 240 |
| Met | Gln | Arg | Ile | Gly | Asp | Met | Thr | Ala | Val | Glu | Val | Lys | Gly | Arg | Ile |
| | | | | 245 | | | | | 250 | | | | | 255 | |
| His | Phe | Asp | Leu | Tyr | His | Val | Ile | Thr | Arg | Thr | Ile | Asn | Leu | Pro | Thr |
| | | | 260 | | | | | 265 | | | | | 270 | | |
| Tyr | Thr | Leu | Glu | Ala | Val | Tyr | Glu | Ala | Ile | Phe | Gly | Lys | Pro | Lys | Glu |
| | | 275 | | | | | 280 | | | | | 285 | | | |
| Lys | Val | Tyr | Ala | Asp | Glu | Ile | Ala | Lys | Ala | Trp | Glu | Ser | Gly | Glu | Asn |
| 290 | | | | | 295 | | | | | 300 | | | | | |
| Leu | Glu | Arg | Val | Ala | Lys | Tyr | Ser | Met | Glu | Asp | Ala | Lys | Val | Thr | Tyr |
| 305 | | | | | 310 | | | | | 315 | | | | | 320 |
| Glu | Leu | Gly | Arg | Glu | Phe | Phe | Pro | Met | Glu | Ala | Gln | Leu | Ser | Arg | Leu |
| | | | | 325 | | | | | 330 | | | | | 335 | |
| Val | Gly | Gln | Pro | Leu | Trp | Asp | Val | Ser | Arg | Ser | Ser | Thr | Gly | Asn | Leu |
| | | | 340 | | | | | 345 | | | | | 350 | | |
| Val | Glu | Trp | Tyr | Leu | Leu | Arg | Lys | Ala | Tyr | Glu | Arg | Asn | Glu | Leu | Ala |
| | | | | 355 | | | | | 360 | | | | | 365 | |
| Pro | Asn | Lys | Pro | Asp | Glu | Arg | Glu | Tyr | Glu | Arg | Arg | Leu | Arg | Glu | Ser |
| | | | 370 | | | | | 375 | | | | | 380 | | |

```
Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
            405                 410                 415

His Asn Val Ser Pro Asp Thr Leu Asn Arg Glu Gly Cys Arg Glu Tyr
        420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
            485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
            515                 520                 525

Leu Glu Glu Lys Phe Gly Phe Lys Val Leu Tyr Ile Asp Thr Asp Gly
530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Ala Arg Gly Phe Phe Val Thr Lys
            580                 585                 590

Lys Lys Tyr Ala Leu Ile Asp Glu Glu Gly Lys Ile Val Thr Arg Gly
            595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Asp Glu Ala
625                 630                 635                 640

Val Lys Ile Val Lys Glu Val Thr Glu Lys Leu Ser Lys Tyr Glu Ile
            645                 650                 655

Pro Pro Glu Lys Leu Val Ile Tyr Glu Gln Ile Thr Arg Pro Leu Ser
            660                 665                 670

Glu Tyr Lys Ala Ile Gly Pro His Val Ala Val Ala Lys Arg Leu Ala
            675                 680                 685

Ala Lys Gly Val Lys Val Lys Pro Gly Met Val Ile Gly Tyr Ile Val
            690                 695                 700

Leu Arg Gly Asp Gly Pro Ile Ser Lys Arg Ala Ile Ala Ile Glu Glu
705                 710                 715                 720

Phe Asp Pro Lys Lys His Lys Tyr Asp Ala Glu Tyr Tyr Ile Glu Asn
                725                 730                 735

Gln Val Leu Pro Ala Val Glu Arg Ile Leu Arg Ala Phe Gly Tyr Arg
            740                 745                 750

Lys Glu Asp Leu Lys Tyr Gln Lys Thr Lys Gln Val Gly Leu Gly Ala
            755                 760                 765

Trp Leu Lys Phe Gly Ser
    770

<210> SEQ ID NO 42
<211> LENGTH: 776
<212> TYPE: PRT
```

<213> ORGANISM: Artificial sequence
<220> FEATURE:
<223> OTHER INFORMATION: Chimeric sequence

<400> SEQUENCE: 42

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
50                  55                  60

Ile Val Asp Val Glu Lys Val Glu Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Tyr Val Lys Glu Pro Glu Lys Gly Leu Trp Glu Gly

```
            385                 390                 395                 400
Leu Val Ser Leu Asp Phe Arg Ser Leu Tyr Pro Ser Ile Ile Ile Thr
                    405                 410                 415
His Asn Val Ser Pro Asp Thr Leu Asn Arg Glu Gly Cys Arg Glu Tyr
                420                 425                 430
Asp Val Ala Pro Glu Val Gly His Lys Phe Cys Lys Asp Phe Pro Gly
            435                 440                 445
Phe Ile Pro Ser Leu Leu Lys Arg Leu Leu Asp Glu Arg Gln Glu Ile
        450                 455                 460
Lys Arg Lys Met Lys Ala Ser Lys Asp Pro Ile Glu Lys Lys Met Leu
465                 470                 475                 480
Asp Tyr Arg Gln Arg Ala Ile Lys Ile Leu Ala Asn Ser Tyr Tyr Gly
                        485                 490                 495
Tyr Tyr Gly Tyr Ala Lys Ala Arg Trp Tyr Cys Lys Glu Cys Ala Glu
                    500                 505                 510
Ser Val Thr Ala Trp Gly Arg Glu Tyr Ile Glu Phe Val Arg Lys Glu
                515                 520                 525
Leu Glu Glu Lys Phe Gly Phe Lys Val Leu Tyr Ile Asp Thr Asp Gly
            530                 535                 540
Leu Tyr Ala Thr Ile Pro Gly Ala Lys Pro Glu Glu Ile Lys Lys Lys
545                 550                 555                 560
Ala Leu Glu Phe Val Asp Tyr Ile Asn Ala Lys Leu Pro Gly Leu Leu
                    565                 570                 575
Glu Leu Glu Tyr Glu Gly Phe Tyr Arg Arg Gly Phe Phe Val Thr Lys
                580                 585                 590
Lys Lys Tyr Ala Val Ile Asp Glu Glu Asp Lys Ile Thr Thr Arg Gly
            595                 600                 605
Leu Glu Ile Val Arg Arg Asp Trp Ser Glu Ile Ala Lys Glu Thr Gln
        610                 615                 620
Ala Arg Val Leu Glu Ala Ile Leu Lys His Gly Asp Val Glu Glu Ala
625                 630                 635                 640
Val Arg Ile Val Lys Glu Val Thr Glu Lys Leu Ser Arg Tyr Glu Val
                    645                 650                 655
Pro Pro Glu Lys Leu Val Ile Tyr Glu Gln Ile Thr Arg Asn Leu Arg
                660                 665                 670
Asp Tyr Arg Ala Thr Gly Pro His Val Ala Val Ala Lys Arg Leu Ala
            675                 680                 685
Ala Arg Gly Ile Lys Ile Arg Pro Gly Thr Val Ile Ser Tyr Ile Val
        690                 695                 700
Leu Lys Gly Pro Gly Arg Val Gly Asp Arg Ala Ile Pro Phe Asp Glu
705                 710                 715                 720
Phe Asp Pro Ala Lys His Arg Tyr Asp Ala Glu Tyr Tyr Ile Glu Asn
                    725                 730                 735
Gln Val Leu Pro Ala Val Glu Arg Ile Leu Arg Ala Phe Gly Tyr Arg
                740                 745                 750
Lys Glu Asp Leu Arg Tyr Gln Lys Thr Lys Gln Ala Gly Leu Gly Ala
            755                 760                 765
Trp Leu Lys Pro Lys Thr Gly Ser
        770                 775

<210> SEQ ID NO 43
<211> LENGTH: 775
<212> TYPE: PRT
<213> ORGANISM: Artificial sequence
```

<220> FEATURE:
<223> OTHER INFORMATION: Chimeric sequence

<400> SEQUENCE: 43

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
            85                  90                  95

Arg Glu Lys Val Arg Glu His Pro Ala Val Val Asp Ile Phe Glu Tyr
        100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Leu Arg Glu Ser
    370                 375                 380

Tyr Ala Gly Gly Tyr Val Lys Glu Pro Glu Lys Gly Leu Trp Glu Gly
385                 390                 395                 400
```

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
            515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Val Ile Asp Glu Glu Gly Lys Ile Thr Thr Arg Gly
            595                 600                 605

Leu Glu Ile Val Arg Arg Asp Trp Ser Glu Ile Ala Lys Glu Thr Gln
    610                 615                 620

Ala Arg Val Leu Glu Ala Leu Leu Lys Asp Gly Asp Val Glu Lys Ala
625                 630                 635                 640

Val Arg Ile Val Lys Glu Val Thr Glu Lys Leu Ser Lys Tyr Glu Val
                645                 650                 655

Pro Pro Glu Lys Leu Val Ile His Glu Gln Ile Thr Arg Asp Leu Lys
            660                 665                 670

Asp Tyr Lys Ala Thr Gly Pro His Val Ala Val Ala Lys Arg Leu Ala
            675                 680                 685

Ala Arg Gly Val Lys Ile Arg Pro Gly Thr Val Ile Ser Tyr Ile Val
    690                 695                 700

Leu Lys Gly Ser Gly Arg Ile Gly Asp Arg Ala Ile Pro Phe Asp Glu
705                 710                 715                 720

Phe Asp Pro Thr Lys His Lys Tyr Asp Ala Glu Tyr Tyr Ile Glu Asn
                725                 730                 735

Gln Val Leu Pro Ala Val Glu Arg Ile Leu Arg Ala Phe Gly Tyr Arg
            740                 745                 750

Lys Glu Asp Leu Arg Tyr Gln Lys Thr Arg Gln Val Gly Leu Ser Ala
            755                 760                 765

Trp Leu Lys Pro Lys Gly Thr
770                 775

<210> SEQ ID NO 44
<211> LENGTH: 776
<212> TYPE: PRT
<213> ORGANISM: Artificial sequence
<220> FEATURE:

<223> OTHER INFORMATION: Chimeric sequence

<400> SEQUENCE: 44

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Glu Gly Gly Tyr Val Lys Glu Pro Glu Lys Gly Leu Trp Glu Gly
385                 390                 395                 400
```

```
Ile Val Ser Leu Asp Phe Arg Ser Leu Tyr Pro Ser Ile Ile Ile Thr
            405                 410                 415

His Asn Val Ser Pro Asp Thr Leu Asn Arg Glu Asn Cys Lys Glu Tyr
        420                 425                 430

Asp Val Ala Pro Gln Val Gly His Arg Phe Cys Lys Asp Phe Pro Gly
            435                 440                 445

Phe Ile Pro Ser Leu Leu Gly Asn Leu Leu Glu Glu Arg Gln Lys Ile
450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Asp Leu Val Arg Arg Glu
            515                 520                 525

Leu Glu Ser Arg Gly Phe Lys Val Leu Tyr Ile Asp Thr Asp Gly Leu
            530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Leu Ile Asp Glu Glu Gly Lys Ile Ile Thr Arg Gly Leu
            595                 600                 605

Glu Ile Val Arg Arg Asp Trp Ser Glu Ile Ala Lys Glu Thr Gln Ala
610                 615                 620

Lys Val Leu Glu Ala Ile Leu Lys His Gly Asn Val Glu Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu His Glu
            660                 665                 670

Tyr Lys Ala Ile Gly Pro His Val Ala Val Ala Lys Arg Leu Ala Ala
            675                 680                 685

Arg Gly Val Lys Val Arg Pro Gly Met Val Ile Gly Tyr Ile Val Leu
            690                 695                 700

Arg Gly Asp Gly Pro Ile Ser Lys Arg Ala Ile Leu Ala Glu Glu Phe
705                 710                 715                 720

Asp Leu Arg Lys His Lys Tyr Asp Ala Glu Tyr Tyr Ile Glu Asn Gln
                725                 730                 735

Val Leu Pro Ala Val Leu Arg Ile Leu Glu Ala Phe Gly Tyr Arg Lys
            740                 745                 750

Glu Asp Leu Arg Trp Gln Lys Thr Lys Gln Thr Gly Leu Thr Ala Trp
            755                 760                 765

Leu Asn Ile Lys Lys Lys Gly Ser
770                 775
```

<210> SEQ ID NO 45
<211> LENGTH: 773
<212> TYPE: PRT
<213> ORGANISM: Artificial sequence
<220> FEATURE:
<223> OTHER INFORMATION: Chimeric sequence

<400> SEQUENCE: 45

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Phe Leu Gly Lys Pro Ile
65                  70                  75                  80

Thr Val Trp Lys Leu Tyr Leu Glu His Pro Gln Asp Val Pro Thr Ile
            85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
            180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
            210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
```

```
            405                 410                 415
His Asn Val Ser Pro Asp Thr Leu Asn Arg Glu Asn Cys Lys Glu Tyr
            420                 425                 430

Asp Val Ala Pro Gln Val Gly His Arg Phe Cys Lys Asp Phe Pro Gly
            435                 440                 445

Phe Ile Pro Ser Leu Leu Gly Asn Leu Leu Glu Glu Arg Gln Lys Ile
    450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Asp Leu Val Arg Arg Glu
            515                 520                 525

Leu Glu Ser Arg Gly Phe Lys Val Leu Tyr Ile Asp Thr Asp Gly Leu
            530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Ala Arg Gly Phe Phe Val Thr Lys Lys
            580                 585                 590

Lys Tyr Ala Leu Ile Asp Glu Glu Gly Lys Ile Val Thr Arg Gly Leu
            595                 600                 605

Glu Ile Val Arg Arg Asp Trp Ser Glu Ile Ala Lys Glu Thr Gln Ala
610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
            660                 665                 670

Tyr Lys Ala Ile Gly Pro His Val Ala Val Ala Lys Arg Leu Ala Ala
            675                 680                 685

Lys Gly Val Lys Val Lys Pro Gly Met Val Ile Gly Tyr Ile Val Leu
            690                 695                 700

Arg Gly Asp Gly Pro Ile Ser Lys Arg Ala Ile Ala Ile Glu Glu Phe
705                 710                 715                 720

Asp Pro Lys Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Lys Tyr Gln Lys Thr Lys Gln Val Gly Leu Gly Ala Trp
            755                 760                 765

Leu Lys Phe Gly Ser
    770

<210> SEQ ID NO 46
<211> LENGTH: 774
<212> TYPE: PRT
<213> ORGANISM: Artificial sequence
<220> FEATURE:
<223> OTHER INFORMATION: Chimeric sequence
```

```
<400> SEQUENCE: 46

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
            85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
        130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
            165                 170                 175

Asp Leu Pro Tyr Val Glu Val Ser Ser Glu Arg Glu Met Ile Lys
        180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Thr Arg Thr Ile Asn Leu Pro Thr
        260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
            325                 330                 335

Val Gly Gln Pro Val Trp Asp Val Ser Arg Ser Ser Thr Gly Asn Leu
        340                 345                 350

Val Glu Trp Phe Leu Leu Arg Lys Ala Tyr Glu Arg Asn Glu Leu Ala
    355                 360                 365

Pro Asn Lys Pro Asp Glu Arg Glu Tyr Glu Arg Arg Leu Arg Glu Ser
    370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
            405                 410                 415
```

His Asn Val Ser Pro Asp Thr Leu Asn Arg Glu Asn Cys Lys Glu Tyr
                420                 425                 430

Asp Val Ala Pro Gln Val Gly His Arg Phe Cys Lys Asp Phe Pro Gly
            435                 440                 445

Phe Ile Pro Ser Leu Leu Gly Asn Leu Leu Glu Arg Gln Lys Ile
450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Gln Tyr Ile Asp Leu Val Arg Arg Glu
            515                 520                 525

Leu Glu Ser Arg Gly Phe Lys Val Leu Tyr Ile Asp Thr Asp Gly Leu
530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
                755                 760                 765

Leu Lys Pro Lys Gly Thr
    770

<210> SEQ ID NO 47
<211> LENGTH: 776
<212> TYPE: PRT
<213> ORGANISM: Artificial sequence
<220> FEATURE:
<223> OTHER INFORMATION: Chimeric sequence

<400> SEQUENCE: 47

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65              70                  75                  80

Thr Val Trp Lys Leu Tyr Leu Glu His Pro Gln Asp Val Pro Thr Ile
            85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
        180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Thr Arg Thr Ile Asn Leu Pro Thr
                260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
            325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Leu Ala Arg Arg Ala Glu Ser Tyr
        370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415
```

```
Asn Val Ser Pro Asp Thr Leu Asn Arg Glu Gly Cys Arg Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Leu Ile Asp Glu Glu Gly Lys Ile Ile Thr Arg Gly Leu
        595                 600                 605

Glu Ile Val Arg Arg Asp Trp Ser Glu Ile Ala Lys Glu Thr Gln Ala
    610                 615                 620

Lys Val Leu Glu Ala Ile Leu Lys His Gly Asn Val Glu Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu His Glu
            660                 665                 670

Tyr Lys Ala Ile Gly Pro His Val Ala Val Ala Lys Arg Leu Ala Ala
        675                 680                 685

Arg Gly Val Lys Val Arg Pro Gly Met Val Ile Gly Tyr Ile Val Leu
    690                 695                 700

Arg Gly Asp Gly Pro Ile Ser Lys Arg Ala Ile Leu Ala Glu Glu Phe
705                 710                 715                 720

Asp Leu Arg Lys His Lys Tyr Asp Ala Glu Tyr Tyr Ile Glu Asn Gln
                725                 730                 735

Val Leu Pro Ala Val Leu Arg Ile Leu Glu Ala Phe Gly Tyr Arg Lys
            740                 745                 750

Glu Asp Leu Arg Trp Gln Lys Thr Lys Gln Thr Gly Leu Thr Ala Trp
        755                 760                 765

Leu Asn Ile Lys Lys Lys Gly Ser
    770                 775

<210> SEQ ID NO 48
<211> LENGTH: 773
<212> TYPE: PRT
<213> ORGANISM: Artificial sequence
<220> FEATURE:
<223> OTHER INFORMATION: Chimeric sequence

<400> SEQUENCE: 48
```

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
        20                  25                  30

Thr Phe Arg Pro Tyr Ile Tyr Ala Leu Leu Arg Asp Asp Ser Lys Ile
            35                  40                  45

Glu Glu Val Lys Lys Ile Thr Gly Glu Arg His Gly Lys Ile Val Arg
50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
            85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Leu Lys Ile Leu Ala Phe Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Ala Glu Ser Tyr
    370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Arg Glu Tyr Asp

```
            420                 425                 430
Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Ala Arg Gly Phe Phe Val Thr Lys Lys
            580                 585                 590

Lys Tyr Ala Leu Ile Asp Glu Glu Gly Lys Ile Val Thr Arg Gly Leu
        595                 600                 605

Glu Ile Val Arg Arg Asp Trp Ser Glu Ile Ala Lys Glu Thr Gln Ala
    610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
            660                 665                 670

Tyr Lys Ala Ile Gly Pro His Val Ala Val Ala Lys Arg Leu Ala Ala
        675                 680                 685

Lys Gly Val Lys Val Lys Pro Gly Met Val Ile Gly Tyr Ile Val Leu
    690                 695                 700

Arg Gly Asp Gly Pro Ile Ser Lys Arg Ala Ile Ala Ile Glu Glu Phe
705                 710                 715                 720

Asp Pro Lys Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Lys Tyr Gln Lys Thr Lys Gln Val Gly Leu Gly Ala Trp
        755                 760                 765

Leu Lys Phe Gly Ser
    770

<210> SEQ ID NO 49
<211> LENGTH: 775
<212> TYPE: PRT
<213> ORGANISM: Artificial sequence
<220> FEATURE:
<223> OTHER INFORMATION: Chimeric sequence

<400> SEQUENCE: 49

Met Ile Leu Asp Val Asp Tyr Ile Thr Glu Glu Gly Lys Pro Val Ile
```

-continued

```
1               5                   10                  15
Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
                35                  40                  45

Glu Glu Val Lys Lys Ile Thr Gly Glu Arg His Gly Lys Ile Val Arg
            50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Asp Ile Phe Glu Tyr
                100                 105                 110

Asp Ile Pro Phe Ala Lys Arg Tyr Leu Ile Asp Lys Gly Leu Ile Pro
                115                 120                 125

Met Glu Gly Glu Glu Leu Lys Ile Leu Ala Phe Asp Ile Glu Thr
                130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
                180                 185                 190

Arg Phe Leu Arg Ile Ile Arg Glu Lys Asp Pro Asp Ile Ile Val Thr
                195                 200                 205

Tyr Asn Gly Asp Ser Phe Asp Phe Pro Tyr Leu Ala Lys Arg Ala Glu
                210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala Asp Glu Ile Ala Lys Ala Trp Glu Ser Gly Glu Asn
                290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Arg Glu Leu Ala Arg Arg Ala Glu Ser Tyr
                370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Arg Glu Tyr Asp
                420                 425                 430
```

```
Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
            500                 505                 510

Val Thr Ala Trp Gly Arg Gln Tyr Ile Glu Thr Met Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Arg Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg Tyr Glu Val Pro
                645                 650                 655

Pro Glu Lys Leu Val Ile Tyr Glu Gln Ile Thr Arg Asn Leu Arg Asp
            660                 665                 670

Tyr Arg Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Pro Gly Arg Val Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Ala Gly Leu Gly Ala Trp
        755                 760                 765

Leu Lys Pro Lys Thr Gly Ser
    770                 775

<210> SEQ ID NO 50
<211> LENGTH: 774
<212> TYPE: PRT
<213> ORGANISM: Artificial sequence
<220> FEATURE:
<223> OTHER INFORMATION: Chimeric sequence

<400> SEQUENCE: 50

Met Ile Leu Asp Val Asp Tyr Ile Thr Glu Glu Gly Lys Pro Val Ile
1               5                   10                  15
```

```
Arg Leu Phe Lys Lys Glu Asn Gly Lys Phe Lys Ile Glu His Asp Arg
             20                  25                  30

Thr Phe Arg Pro Tyr Ile Tyr Ala Leu Leu Arg Asp Asp Ser Lys Ile
         35                  40                  45

Glu Glu Val Lys Lys Ile Thr Gly Glu Arg His Gly Lys Ile Val Arg
 50                  55                  60

Ile Val Asp Val Glu Lys Val Glu Lys Lys Phe Leu Gly Lys Pro Ile
 65                  70                  75                  80

Thr Val Trp Lys Leu Tyr Leu Glu His Pro Gln Asp Val Pro Thr Ile
             85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Ala Glu Ser Tyr
    370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Thr His Asn
                405                 410                 415

Val Ser Pro Asp Thr Leu Asn Arg Glu Gly Cys Arg Glu Tyr Asp
        420                 425                 430
```

Val Ala Pro Gln Val Gly His Arg Phe Cys Lys Asp Phe Pro Gly Phe
435                 440                 445

Ile Pro Ser Leu Leu Gly Asp Leu Leu Glu Glu Arg Gln Lys Val Lys
450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
        515                 520                 525

Glu Glu Lys Phe Gly Phe Lys Val Leu Tyr Ala Asp Thr Asp Gly Phe
530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
770

<210> SEQ ID NO 51
<211> LENGTH: 774
<212> TYPE: PRT
<213> ORGANISM: Artificial sequence
<220> FEATURE:
<223> OTHER INFORMATION: Chimeric sequence

<400> SEQUENCE: 51

Met Ile Leu Asp Val Asp Tyr Ile Thr Glu Glu Gly Lys Pro Val Ile
1               5                   10                  15

-continued

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
            35                  40                  45

Glu Glu Val Lys Lys Ile Thr Gly Glu Arg His Gly Lys Ile Val Arg
        50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Glu Leu Lys Ile Leu Ala Phe Asp Ile Glu Thr
            130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Leu Ala Arg Arg Ala Glu Ser Tyr
            370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Arg Glu Tyr Asp
            420                 425                 430

Val Ala Pro Gln Val Gly His Arg Phe Cys Lys Asp Phe Pro Gly Phe

Ile Pro Ser Leu Leu Gly Asp Leu Leu Glu Glu Arg Gln Lys Val Lys
             450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
            515                 520                 525

Glu Glu Lys Phe Gly Phe Lys Val Leu Tyr Ala Asp Thr Asp Gly Phe
            530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Lys Arg Gly Phe Phe Val Thr Lys Lys
            580                 585                 590

Arg Tyr Ala Val Ile Asp Glu Glu Gly Lys Val Ile Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Thr Ile Leu Lys His Gly Asp Val Glu Glu Ala Val
625                 630                 635                 640

Arg Ile Val Lys Glu Val Ile Gln Lys Leu Ala Asn Tyr Glu Ile Pro
                645                 650                 655

Pro Glu Lys Leu Ala Ile Tyr Glu Gln Ile Thr Arg Pro Leu His Glu
            660                 665                 670

Tyr Lys Ala Ile Gly Pro His Val Ala Val Ala Lys Lys Leu Ala Ala
            675                 680                 685

Lys Gly Val Lys Ile Lys Pro Gly Met Val Ile Gly Tyr Ile Val Leu
690                 695                 700

Arg Gly Asp Gly Pro Ile Ser Asn Arg Ala Ile Leu Ala Glu Glu Tyr
705                 710                 715                 720

Asp Pro Lys Lys His Lys Tyr Asp Ala Glu Tyr Tyr Ile Glu Asn Gln
                725                 730                 735

Val Leu Pro Ala Val Leu Arg Ile Leu Glu Gly Phe Gly Tyr Arg Lys
            740                 745                 750

Glu Asp Leu Arg Tyr Gln Lys Thr Arg Gln Val Gly Leu Thr Ser Trp
            755                 760                 765

Leu Asn Ile Lys Lys Ser
    770

<210> SEQ ID NO 52
<211> LENGTH: 776
<212> TYPE: PRT
<213> ORGANISM: Artificial sequence
<220> FEATURE:
<223> OTHER INFORMATION: Chimeric sequence

<400> SEQUENCE: 52

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg

-continued

```
                    20                  25                  30
Thr Phe Arg Pro Tyr Ile Tyr Ala Leu Leu Arg Asp Asp Ser Lys Ile
                35                  40                  45
Glu Glu Val Lys Lys Ile Thr Gly Glu Arg His Gly Lys Ile Val Arg
            50                  55                  60
Ile Val Asp Val Glu Lys Val Glu Lys Lys Phe Leu Gly Lys Pro Ile
65                  70                  75                  80
Thr Val Trp Lys Leu Tyr Leu Glu His Pro Gln Asp Val Pro Thr Ile
                85                  90                  95
Arg Glu Lys Val Arg Glu His Pro Ala Val Val Asp Ile Phe Glu Tyr
                100                 105                 110
Asp Ile Pro Phe Ala Lys Arg Tyr Leu Ile Asp Lys Gly Leu Ile Pro
                115                 120                 125
Met Glu Gly Glu Glu Leu Lys Ile Leu Ala Phe Asp Ile Glu Thr
                130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Val Ser Ser Glu Arg Glu Met Ile Lys
                180                 185                 190
Arg Phe Leu Arg Ile Ile Arg Glu Lys Asp Pro Asp Ile Ile Val Thr
                195                 200                 205
Tyr Asn Gly Asp Ser Phe Asp Phe Pro Tyr Leu Ala Lys Arg Ala Glu
                210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
                260                 265                 270
Tyr Thr Leu Glu Ala Val Tyr Glu Ala Ile Phe Gly Lys Pro Lys Glu
                275                 280                 285
Lys Val Tyr Ala Asp Glu Ile Ala Lys Ala Trp Glu Ser Gly Glu Asn
                290                 295                 300
Leu Glu Arg Val Ala Lys Tyr Ser Met Glu Asp Ala Lys Val Thr Tyr
305                 310                 315                 320
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Asp Glu Lys Glu Leu Ala Arg Arg Gln Ser Tyr
                370                 375                 380
Glu Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
                420                 425                 430
Val Ala Pro Gln Val Gly His Arg Phe Cys Lys Asp Phe Pro Gly Phe
                435                 440                 445
```

Ile Pro Ser Leu Leu Gly Asp Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                    485                 490                 495

Tyr Gly Tyr Ala Arg Ala Arg Trp Tyr Cys Lys Glu Cys Ala Glu Ser
                500                 505                 510

Val Thr Ala Trp Gly Arg Glu Tyr Ile Thr Met Thr Ile Lys Glu Ile
                515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Val Arg Gly Phe Phe Val Thr Lys Lys
                580                 585                 590

Lys Tyr Ala Leu Ile Asp Glu Glu Gly Lys Ile Ile Thr Arg Gly Leu
    595                 600                 605

Glu Ile Val Arg Arg Asp Trp Ser Glu Ile Ala Lys Glu Thr Gln Ala
    610                 615                 620

Lys Val Leu Glu Ala Ile Leu Lys His Gly Asn Val Glu Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu His Glu
                660                 665                 670

Tyr Lys Ala Ile Gly Pro His Val Ala Val Ala Lys Arg Leu Ala Ala
    675                 680                 685

Arg Gly Val Lys Val Arg Pro Gly Met Val Ile Gly Tyr Ile Val Leu
    690                 695                 700

Arg Gly Asp Gly Pro Ile Ser Lys Arg Ala Ile Leu Ala Glu Glu Phe
705                 710                 715                 720

Asp Leu Arg Lys His Lys Tyr Asp Ala Glu Tyr Tyr Ile Glu Asn Gln
                725                 730                 735

Val Leu Pro Ala Val Leu Arg Ile Leu Glu Ala Phe Gly Tyr Arg Lys
                740                 745                 750

Glu Asp Leu Arg Trp Gln Lys Thr Lys Gln Thr Gly Leu Thr Ala Trp
    755                 760                 765

Leu Asn Ile Lys Lys Gly Ser
    770                 775

<210> SEQ ID NO 53
<211> LENGTH: 773
<212> TYPE: PRT
<213> ORGANISM: Artificial sequence
<220> FEATURE:
<223> OTHER INFORMATION: Chimeric sequence

<400> SEQUENCE: 53

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

```
Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
 50                  55                  60

Ile Val Asp Val Glu Lys Val Glu Lys Phe Leu Gly Lys Pro Ile
 65              70                  75                  80

Thr Val Trp Lys Leu Tyr Leu Glu His Pro Gln Asp Val Pro Thr Ile
                 85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Leu Lys Ile Leu Ala Phe Asp Ile Glu Thr
        130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
            290                 295                 300

Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445
```

```
Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Ala Arg Gly Phe Phe Val Thr Lys Lys
            580                 585                 590

Lys Tyr Ala Leu Ile Asp Glu Glu Gly Lys Ile Val Thr Arg Gly Leu
        595                 600                 605

Glu Ile Val Arg Arg Asp Trp Ser Glu Ile Ala Lys Glu Thr Gln Ala
    610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
            660                 665                 670

Tyr Lys Ala Ile Gly Pro His Val Ala Val Ala Lys Arg Leu Ala Ala
        675                 680                 685

Lys Gly Val Lys Val Lys Pro Gly Met Val Ile Gly Tyr Ile Val Leu
    690                 695                 700

Arg Gly Asp Gly Pro Ile Ser Lys Arg Ala Ile Ala Ile Glu Glu Phe
705                 710                 715                 720

Asp Pro Lys Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Lys Tyr Gln Lys Thr Lys Gln Val Gly Leu Gly Ala Trp
        755                 760                 765

Leu Lys Phe Gly Ser
    770

<210> SEQ ID NO 54
<211> LENGTH: 775
<212> TYPE: PRT
<213> ORGANISM: Artificial sequence
<220> FEATURE:
<223> OTHER INFORMATION: Chimeric sequence

<400> SEQUENCE: 54

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30
```

-continued

Thr Phe Arg Pro Tyr Ile Tyr Ala Leu Leu Arg Asp Ser Lys Ile
        35                  40                  45

Glu Glu Val Lys Lys Ile Thr Gly Glu Arg His Gly Lys Ile Val Arg
 50                  55                  60

Ile Val Asp Val Glu Lys Val Glu Lys Lys Phe Leu Gly Lys Pro Ile
 65                  70                  75                  80

Thr Val Trp Lys Leu Tyr Leu Glu His Pro Gln Asp Val Pro Thr Ile
                 85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Glu Leu Lys Ile Leu Ala Phe Asp Ile Glu Thr
            130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
            210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Ser Gly Glu Asn
            290                 295                 300

Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Gln Ser Tyr
            370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys

```
                450                 455                 460
Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
                500                 505                 510

Val Thr Ala Trp Gly Arg Glu Tyr Ile Thr Met Thr Ile Lys Glu Ile
                515                 520                 525

Glu Glu Lys Tyr Gly Phe Lys Val Ile Tyr Ser Asp Thr Asp Gly Phe
530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Arg Arg Gly Phe Phe Val Thr Lys Lys
                580                 585                 590

Lys Tyr Ala Val Ile Asp Glu Glu Asp Lys Ile Thr Thr Arg Gly Leu
                595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg Tyr Glu Val Pro
                645                 650                 655

Pro Glu Lys Leu Val Ile Tyr Glu Gln Ile Thr Arg Asn Leu Arg Asp
                660                 665                 670

Tyr Arg Ala Thr Gly Pro His Val Ala Val Ala Lys Arg Leu Ala Ala
                675                 680                 685

Arg Gly Ile Lys Ile Arg Pro Gly Thr Val Ile Ser Tyr Ile Val Leu
690                 695                 700

Lys Gly Pro Gly Arg Val Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Lys Gln Ala Gly Leu Gly Ala Trp
                755                 760                 765

Leu Lys Pro Lys Thr Gly Ser
770                 775

<210> SEQ ID NO 55
<211> LENGTH: 774
<212> TYPE: PRT
<213> ORGANISM: Artificial sequence
<220> FEATURE:
<223> OTHER INFORMATION: Chimeric sequence

<400> SEQUENCE: 55

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
```

```
                35                  40                  45
Glu Glu Val Lys Lys Ile Thr Gly Glu Arg His Gly Lys Ile Val Arg
 50                  55                  60

Ile Val Asp Val Glu Lys Val Glu Lys Lys Phe Leu Gly Lys Pro Ile
 65                  70                  75                  80

Thr Val Trp Lys Leu Tyr Leu Glu His Pro Gln Asp Val Pro Thr Ile
                 85                  90                  95

Arg Glu Lys Val Arg Glu His Pro Ala Val Asp Ile Phe Glu Tyr
                100                 105                 110

Asp Ile Pro Phe Ala Lys Arg Tyr Leu Ile Asp Lys Gly Leu Ile Pro
                115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
                180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
                260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
    355                 360                 365

Pro Asn Lys Pro Asp Glu Lys Glu Leu Ala Arg Arg Gln Ser Tyr
            370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
                435                 440                 445

Ile Pro Ser Leu Leu Gly Asp Leu Leu Glu Glu Arg Gln Lys Ile Lys
            450                 455                 460
```

```
Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 56
<211> LENGTH: 774
<212> TYPE: PRT
<213> ORGANISM: Artificial sequence
<220> FEATURE:
<223> OTHER INFORMATION: Chimeric sequence

<400> SEQUENCE: 56

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45
```

-continued

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
    195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
    275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
    355                 360                 365

Pro Asn Lys Pro Asp Glu Lys Glu Leu Ala Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
    435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Arg Tyr Ala Val Ile Asp Glu Glu Gly Lys Val Ile Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Thr Ile Leu Lys His Gly Asp Val Glu Glu Ala Val
625                 630                 635                 640

Arg Ile Val Lys Glu Val Ile Gln Lys Leu Ala Asn Tyr Glu Ile Pro
                645                 650                 655

Pro Glu Lys Leu Ala Ile Tyr Glu Gln Ile Thr Arg Pro Leu His Glu
            660                 665                 670

Tyr Lys Ala Ile Gly Pro His Val Ala Val Lys Lys Leu Ala Ala
        675                 680                 685

Lys Gly Val Lys Ile Lys Pro Gly Met Val Ile Gly Tyr Ile Val Leu
    690                 695                 700

Arg Gly Asp Gly Pro Ile Ser Asn Arg Ala Ile Leu Ala Glu Glu Tyr
705                 710                 715                 720

Asp Pro Lys Lys His Lys Tyr Asp Ala Glu Tyr Tyr Ile Glu Asn Gln
                725                 730                 735

Val Leu Pro Ala Val Leu Arg Ile Leu Glu Gly Phe Gly Tyr Arg Lys
            740                 745                 750

Glu Asp Leu Arg Tyr Gln Lys Thr Arg Gln Val Gly Leu Thr Ser Trp
        755                 760                 765

Leu Asn Ile Lys Lys Ser
    770

<210> SEQ ID NO 57
<211> LENGTH: 775
<212> TYPE: PRT
<213> ORGANISM: Artificial sequence
<220> FEATURE:
<223> OTHER INFORMATION: Chimeric sequence

<400> SEQUENCE: 57

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
            35                  40                  45

```
Glu Glu Val Lys Lys Ile Thr Gly Glu Arg His Gly Lys Ile Val Arg
 50                  55                  60

Ile Val Asp Val Glu Lys Val Glu Lys Phe Leu Gly Lys Pro Ile
 65              70                  75                  80

Thr Val Trp Lys Leu Tyr Leu Glu His Pro Gln Asp Val Pro Thr Ile
                 85                  90                  95

Arg Glu Lys Val Arg Glu His Pro Ala Val Asp Ile Phe Glu Tyr
                100             105                 110

Asp Ile Pro Phe Ala Lys Arg Tyr Leu Ile Asp Lys Gly Leu Ile Pro
            115                 120                 125

Met Glu Gly Glu Glu Leu Lys Ile Leu Ala Phe Asp Ile Glu Thr
130                 135                 140

Leu Tyr His Glu Gly Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
                180                 185                 190

Arg Phe Leu Arg Ile Ile Arg Glu Lys Asp Pro Asp Ile Ile Val Thr
                195                 200                 205

Tyr Asn Gly Asp Ser Phe Asp Phe Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala Asp Glu Ile Ala Lys Ala Trp Glu Ser Gly Glu Asn
                290                 295                 300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Arg Glu Tyr Glu Arg Arg Leu Arg Glu Ser
                370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Thr
                    405                 410                 415

His Asn Val Ser Pro Asp Thr Leu Asn Arg Glu Asn Cys Lys Glu Tyr
                420                 425                 430

Asp Val Ala Pro Gln Val Gly His Arg Phe Cys Lys Asp Phe Pro Gly
                435                 440                 445

Phe Ile Pro Ser Leu Leu Gly Asn Leu Leu Glu Glu Arg Gln Lys Ile
450                 455                 460

Lys Lys Arg Met Lys Glu Ser Lys Asp Pro Val Glu Lys Lys Leu Leu
```

```
            465                 470                 475                 480
        Asp Tyr Arg Gln Arg Ala Ile Lys Ile Leu Ala Asn Ser Tyr Tyr Gly
                        485                 490                 495

Tyr Tyr Gly Tyr Ala Lys Ala Arg Trp Tyr Cys Lys Glu Cys Ala Glu
                        500                 505                 510

Ser Val Thr Ala Trp Gly Arg Gln Tyr Ile Asp Leu Val Arg Arg Glu
                        515                 520                 525

Leu Glu Ser Arg Gly Phe Lys Val Leu Tyr Ile Asp Thr Asp Gly Leu
                        530                 535                 540

Tyr Ala Thr Ile Pro Gly Ala Lys His Glu Glu Ile Lys Glu Lys Ala
        545                 550                 555                 560

Leu Lys Phe Val Glu Tyr Ile Asn Ser Lys Leu Pro Gly Leu Leu Glu
                        565                 570                 575

Leu Glu Tyr Glu Gly Phe Tyr Arg Arg Gly Phe Phe Val Thr Lys Lys
                        580                 585                 590

Lys Tyr Ala Val Ile Asp Glu Glu Asp Lys Ile Thr Thr Arg Gly Leu
                        595                 600                 605

Glu Ile Val Arg Arg Asp Trp Ser Glu Ile Ala Lys Glu Thr Gln Ala
                        610                 615                 620

Arg Val Leu Glu Ala Ile Leu Lys His Gly Asp Val Glu Glu Ala Val
        625                 630                 635                 640

Arg Ile Val Lys Glu Val Thr Glu Lys Leu Ser Arg Tyr Glu Val Pro
                        645                 650                 655

Pro Glu Lys Leu Val Ile Tyr Glu Gln Ile Thr Arg Asn Leu Arg Asp
                        660                 665                 670

Tyr Arg Ala Thr Gly Pro His Val Ala Val Ala Lys Arg Leu Ala Ala
                        675                 680                 685

Arg Gly Ile Lys Ile Arg Pro Gly Thr Val Ile Ser Tyr Ile Val Leu
                        690                 695                 700

Lys Gly Pro Gly Arg Val Gly Asp Arg Ala Ile Pro Phe Asp Glu Phe
        705                 710                 715                 720

Asp Pro Ala Lys His Arg Tyr Asp Ala Glu Tyr Tyr Ile Glu Asn Gln
                        725                 730                 735

Val Leu Pro Ala Val Glu Arg Ile Leu Arg Ala Phe Gly Tyr Arg Lys
                        740                 745                 750

Glu Asp Leu Arg Tyr Gln Lys Thr Lys Gln Ala Gly Leu Gly Ala Trp
                        755                 760                 765

Leu Lys Pro Lys Thr Gly Ser
            770                 775

<210> SEQ ID NO 58
<211> LENGTH: 774
<212> TYPE: PRT
<213> ORGANISM: Artificial sequence
<220> FEATURE:
<223> OTHER INFORMATION: Chimeric sequence

<400> SEQUENCE: 58

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asn Tyr Asp Arg
                20                  25                  30

Asp Phe Glu Pro Tyr Ile Tyr Ala Leu Leu Lys Asp Asp Ser Ala Ile
            35                  40                  45

Glu Asp Ile Lys Lys Ile Thr Ala Glu Arg His Gly Thr Thr Val Arg
```

```
            50                  55                  60
Val Thr Arg Ala Glu Arg Val Lys Lys Phe Leu Gly Arg Pro Val
 65                      70                  75                  80

Glu Val Trp Lys Leu Tyr Phe Thr His Pro Gln Asp Val Pro Ala Ile
                     85                  90                  95

Arg Asp Lys Ile Arg Glu His Pro Ala Val Val Asp Ile Tyr Glu Tyr
                    100                 105                 110

Asp Ile Pro Phe Ala Lys Arg Tyr Leu Ile Asp Lys Gly Leu Ile Pro
                115                     120                 125

Met Glu Gly Asn Glu Glu Leu Arg Met Leu Ala Phe Asp Ile Glu Thr
                130                 135                 140

Leu Tyr His Glu Gly Glu Glu Phe Gly Glu Gly Pro Ile Leu Met Ile
145                     150                 155                     160

Ser Tyr Ala Asp Glu Glu Gly Ala Arg Val Ile Thr Trp Lys Asn Ile
                    165                 170                 175

Asp Leu Pro Tyr Val Glu Ser Val Ser Thr Glu Lys Glu Met Ile Lys
                180                 185                 190

Arg Phe Leu Lys Val Ile Gln Glu Lys Asp Pro Asp Val Leu Ile Thr
            195                 200                 205

Tyr Asn Gly Asp Asn Phe Asp Phe Ala Tyr Leu Lys Lys Arg Ser Glu
        210                 215                 220

Thr Leu Gly Val Lys Phe Ile Leu Gly Arg Asp Gly Ser Glu Pro Lys
225                     230                 235                 240

Ile Gln Arg Met Gly Asp Arg Phe Ala Val Glu Val Lys Gly Arg Ile
                    245                 250                 255

His Phe Asp Leu Tyr Pro Val Ile Arg Arg Thr Ile Asn Leu Pro Thr
                260                 265                 270

Tyr Thr Leu Glu Thr Val Tyr Glu Ala Ile Phe Gly Gln Pro Lys Glu
                275                 280                 285

Lys Val Tyr Ala Glu Glu Ile Ala Gln Ala Trp Glu Ser Gly Glu Gly
                290                 295                 300

Leu Glu Arg Val Ala Arg Tyr Ser Met Glu Asp Ala Lys Val Thr Tyr
305                     310                 315                 320

Glu Leu Gly Arg Glu Phe Phe Pro Met Glu Ala Gln Leu Ser Arg Leu
                    325                 330                 335

Val Gly Gln Pro Leu Trp Asp Val Ser Arg Ser Ser Thr Gly Asn Leu
                340                 345                 350

Val Glu Trp Tyr Leu Leu Arg Lys Ala Tyr Glu Arg Asn Glu Leu Ala
                355                 360                 365

Pro Asn Lys Pro Asp Glu Arg Glu Tyr Glu Arg Arg Leu Arg Glu Ser
                370                 375                 380

Tyr Ala Gly Gly Tyr Val Lys Glu Pro Glu Lys Gly Leu Trp Glu Gly
385                     390                 395                 400

Leu Val Ser Leu Asp Phe Arg Ser Leu Tyr Pro Ser Ile Ile Ile Thr
                    405                 410                 415

His Asn Val Ser Pro Asp Thr Leu Asn Arg Glu Gly Cys Arg Glu Tyr
                420                 425                 430

Asp Val Ala Pro Glu Val Gly His Lys Phe Cys Lys Asp Phe Pro Gly
                435                 440                 445

Phe Ile Pro Ser Leu Leu Lys Arg Leu Leu Asp Glu Arg Gln Glu Ile
                450                 455                 460

Lys Arg Lys Met Lys Ala Ser Lys Asp Pro Ile Glu Lys Lys Met Leu
465                     470                 475                 480
```

Asp Tyr Arg Gln Arg Ala Ile Lys Ile Leu Ala Asn Ser Tyr Tyr Gly
            485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Ala Arg Gly Phe Phe Val Thr Lys
            580                 585                 590

Lys Lys Tyr Ala Leu Ile Asp Glu Glu Gly Lys Ile Val Thr Arg Gly
            595                 600                 605

Leu Glu Ile Val Arg Arg Asp Trp Ser Glu Ile Ala Lys Glu Thr Gln
            610                 615                 620

Ala Lys Val Leu Glu Ala Ile Leu Lys His Gly Asn Val Asp Glu Ala
625                 630                 635                 640

Val Lys Ile Val Lys Glu Val Thr Glu Lys Leu Ser Lys Tyr Glu Ile
            645                 650                 655

Pro Pro Glu Lys Leu Val Ile Tyr Glu Gln Ile Thr Arg Pro Leu Ser
            660                 665                 670

Glu Tyr Lys Ala Ile Gly Pro His Val Ala Val Ala Lys Arg Leu Ala
            675                 680                 685

Ala Lys Gly Val Lys Val Lys Pro Gly Met Val Ile Gly Tyr Ile Val
690                 695                 700

Leu Arg Gly Asp Gly Pro Ile Ser Lys Arg Ala Ile Ala Ile Glu Glu
705                 710                 715                 720

Phe Asp Pro Lys Lys His Lys Tyr Asp Ala Glu Tyr Tyr Ile Glu Asn
                725                 730                 735

Gln Val Leu Pro Ala Val Glu Arg Ile Leu Arg Ala Phe Gly Tyr Arg
            740                 745                 750

Lys Glu Asp Leu Lys Tyr Gln Lys Thr Lys Gln Val Gly Leu Gly Ala
            755                 760                 765

Trp Leu Lys Phe Gly Ser
    770

<210> SEQ ID NO 59
<211> LENGTH: 777
<212> TYPE: PRT
<213> ORGANISM: Artificial sequence
<220> FEATURE:
<223> OTHER INFORMATION: Chimeric sequence

<400> SEQUENCE: 59

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asn Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60

```
Val Thr Arg Ala Glu Arg Val Lys Lys Lys Phe Leu Gly Arg Pro Val
 65                  70                  75                  80

Glu Val Trp Lys Leu Tyr Phe Thr His Pro Gln Asp Val Pro Ala Ile
                 85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asn Glu Glu Leu Arg Met Leu Ala Phe Asp Ile Glu Thr
130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
            195                 200                 205

Tyr Asn Gly Asp Asn Phe Asp Phe Ala Tyr Leu Lys Lys Arg Ser Glu
210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Ala Ile Phe Gly Gln Pro Lys Glu
            275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Glu Ile
450                 455                 460

Lys Arg Lys Met Lys Ala Ser Lys Asp Pro Ile Glu Lys Lys Met Leu
465                 470                 475                 480
```

-continued

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Val Ile Asp Glu Glu Gly Lys Ile Thr Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Ala Leu Leu Lys Asp Gly Asp Val Glu Lys Ala
625                 630                 635                 640

Val Arg Ile Val Lys Glu Val Thr Glu Lys Leu Ser Lys Tyr Glu Val
                645                 650                 655

Pro Pro Glu Lys Leu Val Ile His Glu Gln Ile Thr Arg Asp Leu Lys
            660                 665                 670

Asp Tyr Lys Ala Thr Gly Pro His Val Ala Val Ala Lys Arg Leu Ala
        675                 680                 685

Ala Arg Gly Val Lys Ile Arg Pro Gly Thr Val Ile Ser Tyr Ile Val
690                 695                 700

Leu Lys Gly Ser Gly Arg Ile Gly Asp Arg Ala Ile Pro Phe Asp Glu
705                 710                 715                 720

Phe Asp Pro Thr Lys His Lys Tyr Asp Ala Glu Tyr Tyr Ile Glu Asn
                725                 730                 735

Gln Val Leu Pro Ala Val Glu Arg Ile Leu Arg Ala Phe Gly Tyr Arg
            740                 745                 750

Lys Glu Asp Leu Arg Tyr Gln Lys Thr Arg Gln Val Gly Leu Ser Ala
        755                 760                 765

Trp Leu Lys Pro Lys Gly Thr Gly Ser
    770                 775

<210> SEQ ID NO 60
<211> LENGTH: 777
<212> TYPE: PRT
<213> ORGANISM: Artificial sequence
<220> FEATURE:
<223> OTHER INFORMATION: Chimeric sequence

<400> SEQUENCE: 60

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asn Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60

Val Thr Arg Ala Glu Arg Val Lys Lys Lys Phe Leu Gly Arg Pro Val
65                  70                  75                  80

Glu Val Trp Lys Leu Tyr Phe Thr His Pro Gln Asp Val Pro Ala Ile
            85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asn Glu Glu Leu Arg Met Leu Ala Phe Asp Ile Glu Thr
130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
            165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
            195                 200                 205

Tyr Asn Gly Asp Asn Phe Asp Phe Ala Tyr Leu Lys Lys Arg Ser Glu
210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Ala Ile Phe Gly Gln Pro Lys Glu
            275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
            405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Glu Ile
            450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly

```
                485                 490                 495
Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
            565                 570                 575

Glu Leu Glu Tyr Glu Gly Phe Tyr Lys Arg Gly Phe Phe Val Thr Lys
        580                 585                 590

Lys Arg Tyr Ala Val Ile Asp Glu Glu Gly Lys Val Ile Thr Arg Gly
    595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
            645                 650                 655

Pro Pro Glu Lys Leu Ala Ile Tyr Glu Gln Ile Thr Arg Pro Leu His
        660                 665                 670

Glu Tyr Lys Ala Ile Gly Pro His Val Ala Val Ala Lys Lys Leu Ala
    675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
            725                 730                 735

Gln Val Leu Pro Ala Val Leu Arg Ile Leu Glu Gly Phe Gly Tyr Arg
        740                 745                 750

Lys Glu Asp Leu Arg Tyr Gln Lys Thr Arg Gln Val Gly Leu Thr Ser
    755                 760                 765

Trp Leu Asn Ile Lys Lys Ser Gly Ser
770                 775

<210> SEQ ID NO 61
<211> LENGTH: 776
<212> TYPE: PRT
<213> ORGANISM: Artificial sequence
<220> FEATURE:
<223> OTHER INFORMATION: Chimeric sequence

<400> SEQUENCE: 61

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asn Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60

Val Thr Arg Ala Glu Arg Val Lys Lys Lys Phe Leu Gly Arg Pro Val
```

-continued

```
                65                  70                  75                  80
Glu Val Trp Lys Leu Tyr Phe Thr His Pro Gln Asp Val Pro Ala Ile
                    85                  90                  95
Arg Asp Lys Ile Arg Glu His Pro Ala Val Val Asp Ile Tyr Glu Tyr
                100                 105                 110
Asp Ile Pro Phe Ala Lys Arg Tyr Leu Ile Asp Lys Gly Leu Ile Pro
                115                 120                 125
Met Glu Gly Asn Glu Glu Leu Arg Met Leu Ala Phe Asp Ile Glu Thr
                130                 135                 140
Leu Tyr His Glu Gly Glu Glu Phe Gly Glu Gly Pro Ile Leu Met Ile
145                 150                 155                 160
Ser Tyr Ala Asp Glu Glu Gly Ala Arg Val Ile Thr Trp Lys Asn Ile
                    165                 170                 175
Asp Leu Pro Tyr Val Glu Ser Val Ser Thr Glu Lys Glu Met Ile Lys
                180                 185                 190
Arg Phe Leu Lys Val Ile Gln Glu Lys Asp Pro Asp Val Leu Ile Thr
                195                 200                 205
Tyr Asn Gly Asp Asn Phe Asp Phe Ala Tyr Leu Lys Lys Arg Ser Glu
                210                 215                 220
Thr Leu Gly Val Lys Phe Ile Leu Gly Arg Asp Gly Ser Glu Pro Lys
225                 230                 235                 240
Ile Gln Arg Met Gly Asp Arg Phe Ala Val Glu Val Lys Gly Arg Ile
                    245                 250                 255
His Phe Asp Leu Tyr Pro Val Ile Arg Arg Thr Ile Asn Leu Pro Thr
                260                 265                 270
Tyr Thr Leu Glu Thr Val Tyr Glu Ala Ile Phe Gly Gln Pro Lys Glu
                275                 280                 285
Lys Val Tyr Ala Glu Glu Ile Ala Gln Ala Trp Glu Ser Gly Glu Gly
                290                 295                 300
Leu Glu Arg Val Ala Arg Tyr Ser Met Glu Asp Ala Lys Val Thr Phe
305                 310                 315                 320
Glu Leu Gly Lys Glu Phe Phe Pro Met Glu Ala Gln Leu Ala Arg Leu
                    325                 330                 335
Val Gly Gln Pro Val Trp Asp Val Ser Arg Ser Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Asp Glu Arg Glu Tyr Glu Arg Arg Leu Arg Glu Ser
                370                 375                 380
Tyr Glu Gly Gly Tyr Val Lys Glu Pro Glu Lys Gly Leu Trp Glu Gly
385                 390                 395                 400
Ile Val Ser Leu Asp Phe Arg Ser Leu Tyr Pro Ser Ile Ile Ile Thr
                    405                 410                 415
His Asn Val Ser Pro Asp Thr Leu Asn Arg Glu Asn Cys Lys Glu Tyr
                420                 425                 430
Asp Val Ala Pro Gln Val Gly His Arg Phe Cys Lys Asp Phe Pro Gly
                435                 440                 445
Phe Ile Pro Ser Leu Leu Gly Asn Leu Leu Glu Glu Arg Gln Lys Ile
                450                 455                 460
Lys Lys Arg Met Lys Glu Ser Lys Asp Pro Val Glu Lys Lys Leu Leu
465                 470                 475                 480
Asp Tyr Arg Gln Arg Ala Ile Lys Ile Leu Ala Asn Ser Tyr Tyr Gly
                    485                 490                 495
```

```
Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Asp Leu Val Arg Arg Glu
        515                 520                 525

Leu Glu Ser Arg Gly Phe Lys Val Leu Tyr Ile Asp Thr Asp Gly Leu
    530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Leu Ile Asp Glu Glu Gly Lys Ile Ile Thr Arg Gly Leu
        595                 600                 605

Glu Ile Val Arg Arg Asp Trp Ser Glu Ile Ala Lys Glu Thr Gln Ala
    610                 615                 620

Lys Val Leu Glu Ala Ile Leu Lys His Gly Asn Val Glu Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu His Glu
            660                 665                 670

Tyr Lys Ala Ile Gly Pro His Val Ala Val Ala Lys Arg Leu Ala Ala
        675                 680                 685

Arg Gly Val Lys Val Arg Pro Gly Met Val Ile Gly Tyr Ile Val Leu
    690                 695                 700

Arg Gly Asp Gly Pro Ile Ser Lys Arg Ala Ile Leu Ala Glu Glu Phe
705                 710                 715                 720

Asp Leu Arg Lys His Lys Tyr Asp Ala Glu Tyr Tyr Ile Glu Asn Gln
                725                 730                 735

Val Leu Pro Ala Val Leu Arg Ile Leu Glu Ala Phe Gly Tyr Arg Lys
            740                 745                 750

Glu Asp Leu Arg Trp Gln Lys Thr Lys Gln Thr Gly Leu Thr Ala Trp
        755                 760                 765

Leu Asn Ile Lys Lys Lys Gly Ser
    770                 775

<210> SEQ ID NO 62
<211> LENGTH: 776
<212> TYPE: PRT
<213> ORGANISM: Artificial sequence
<220> FEATURE:
<223> OTHER INFORMATION: Chimeric sequence

<400> SEQUENCE: 62

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asn Tyr Asp Arg
                20                  25                  30

Asp Phe Glu Pro Tyr Ile Tyr Ala Leu Leu Lys Asp Asp Ser Ala Ile
            35                  40                  45

Glu Asp Ile Lys Lys Ile Thr Ala Glu Arg His Gly Thr Thr Val Arg
        50                  55                  60

Val Thr Arg Ala Glu Arg Val Lys Lys Lys Phe Leu Gly Arg Pro Val
65                  70                  75                  80
```

-continued

```
Glu Val Trp Lys Leu Tyr Phe Thr His Pro Gln Asp Val Pro Ala Ile
            85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asn Glu Glu Leu Arg Met Leu Ala Phe Asp Ile Glu Thr
130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
                180                 185                 190

Arg Phe Leu Lys Val Ile Gln Glu Lys Asp Pro Asp Val Leu Ile Thr
                195                 200                 205

Tyr Asn Gly Asp Asn Phe Asp Phe Ala Tyr Leu Lys Lys Arg Ser Glu
210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Thr Val Tyr Glu Ala Ile Phe Gly Gln Pro Lys Glu
                275                 280                 285

Lys Val Tyr Ala Glu Glu Ile Ala Gln Ala Trp Glu Ser Gly Glu Gly
                290                 295                 300

Leu Glu Arg Val Ala Arg Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Arg Glu Tyr Glu Arg Arg Leu Arg Glu Ser
370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Asn Cys Lys Glu Tyr
                420                 425                 430

Asp Val Ala Pro Gln Val Gly His Arg Phe Cys Lys Asp Phe Pro Gly
                435                 440                 445

Phe Ile Pro Ser Leu Leu Gly Asn Leu Leu Glu Glu Arg Gln Lys Ile
450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495
```

```
Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Asp Leu Val Arg Arg Glu
    515                 520                 525

Leu Glu Ser Arg Gly Phe Lys Val Leu Tyr Ile Asp Thr Asp Gly Leu
        530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr Gly Ser
    770                 775

<210> SEQ ID NO 63
<211> LENGTH: 776
<212> TYPE: PRT
<213> ORGANISM: Artificial sequence
<220> FEATURE:
<223> OTHER INFORMATION: Chimeric sequence

<400> SEQUENCE: 63

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asn Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60

Val Thr Arg Ala Glu Arg Val Lys Lys Phe Leu Gly Arg Pro Val
65                  70                  75                  80
```

```
Glu Val Trp Lys Leu Tyr Phe Thr His Pro Gln Asp Val Pro Ala Ile
             85                  90                  95

Arg Asp Lys Ile Arg Glu His Pro Ala Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asn Glu Glu Leu Arg Met Leu Ala Phe Asp Ile Glu Thr
            130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
            195                 200                 205

Tyr Asn Gly Asp Asn Phe Asp Phe Ala Tyr Leu Lys Lys Arg Ser Glu
            210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Ala Ile Phe Gly Gln Pro Lys Glu
            275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Val Thr Phe
305                 310                 315                 320

Glu Leu Gly Lys Glu Phe Phe Pro Met Glu Ala Gln Leu Ala Arg Leu
            325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
            370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
            405                 410                 415

His Asn Val Ser Pro Asp Thr Leu Asn Arg Glu Asn Cys Lys Glu Tyr
            420                 425                 430

Asp Val Ala Pro Gln Val Gly His Arg Phe Cys Lys Asp Phe Pro Gly
            435                 440                 445

Phe Ile Pro Ser Leu Leu Gly Asn Leu Leu Glu Glu Arg Gln Lys Ile
            450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
```

```
                500            505             510
Ser Val Thr Ala Trp Gly Arg Gln Tyr Ile Asp Leu Val Arg Arg Glu
            515             520             525

Leu Glu Ser Arg Gly Phe Lys Val Leu Tyr Ile Asp Thr Asp Gly Leu
            530             535             540

Tyr Ala Thr Ile Pro Gly Ala Lys His Glu Glu Ile Lys Glu Lys Ala
545             550             555             560

Leu Lys Phe Val Glu Tyr Ile Asn Ser Lys Leu Pro Gly Leu Leu Glu
            565             570             575

Leu Glu Tyr Glu Gly Phe Tyr Lys Arg Gly Phe Phe Val Thr Lys Lys
            580             585             590

Arg Tyr Ala Val Ile Asp Glu Glu Gly Lys Val Ile Thr Arg Gly Leu
            595             600             605

Glu Ile Val Arg Arg Asp Trp Ser Glu Ile Ala Lys Glu Thr Gln Ala
            610             615             620

Arg Val Leu Glu Thr Ile Leu Lys His Gly Asp Val Glu Glu Ala Val
625             630             635             640

Arg Ile Val Lys Glu Val Ile Gln Lys Leu Ala Asn Tyr Glu Ile Pro
            645             650             655

Pro Glu Lys Leu Ala Ile Tyr Glu Gln Ile Thr Arg Pro Leu His Glu
            660             665             670

Tyr Lys Ala Ile Gly Pro His Val Ala Val Ala Lys Lys Leu Ala Ala
            675             680             685

Lys Gly Val Lys Ile Lys Pro Gly Met Val Ile Gly Tyr Ile Val Leu
            690             695             700

Arg Gly Asp Gly Pro Ile Ser Asn Arg Ala Ile Leu Ala Glu Glu Tyr
705             710             715             720

Asp Pro Lys Lys His Lys Tyr Asp Ala Glu Tyr Tyr Ile Glu Asn Gln
            725             730             735

Val Leu Pro Ala Val Leu Arg Ile Leu Glu Gly Phe Gly Tyr Arg Lys
            740             745             750

Glu Asp Leu Arg Tyr Gln Lys Thr Arg Gln Val Gly Leu Thr Ser Trp
            755             760             765

Leu Asn Ile Lys Lys Ser Gly Ser
            770             775

<210> SEQ ID NO 64
<211> LENGTH: 776
<212> TYPE: PRT
<213> ORGANISM: Artificial sequence
<220> FEATURE:
<223> OTHER INFORMATION: Chimeric sequence

<400> SEQUENCE: 64

Met Ile Leu Asp Ala Asp Tyr Ile Thr Glu Asp Gly Lys Pro Val Ile
1               5               10              15

Arg Val Phe Lys Lys Glu Lys Gly Glu Phe Lys Ile Asn Tyr Asp Arg
            20              25              30

Asp Phe Glu Pro Tyr Ile Tyr Ala Leu Leu Lys Asp Asp Ser Ala Ile
            35              40              45

Glu Asp Ile Lys Lys Ile Thr Ala Glu Arg His Gly Thr Thr Val Arg
            50              55              60

Val Thr Arg Ala Glu Arg Val Lys Lys Lys Phe Leu Gly Arg Pro Val
65              70              75              80

Glu Val Trp Lys Leu Tyr Phe Thr His Pro Gln Asp Val Pro Ala Ile
```

-continued

```
                    85                  90                  95
Arg Asp Lys Ile Arg Glu His Pro Ala Val Val Asp Ile Tyr Glu Tyr
                100                 105                 110
Asp Ile Pro Phe Ala Lys Arg Tyr Leu Ile Asp Lys Gly Leu Ile Pro
                115                 120                 125
Met Glu Gly Asn Glu Glu Leu Arg Met Leu Ala Phe Asp Ile Glu Thr
                130                 135                 140
Leu Tyr His Glu Gly Glu Glu Phe Gly Glu Gly Pro Ile Leu Met Ile
145                 150                 155                 160
Ser Tyr Ala Asp Glu Glu Gly Ala Arg Val Ile Thr Trp Lys Asn Ile
                165                 170                 175
Asp Leu Pro Tyr Val Glu Ser Val Ser Thr Glu Lys Glu Met Ile Lys
                180                 185                 190
Arg Phe Leu Lys Val Ile Gln Glu Lys Asp Pro Asp Val Leu Ile Thr
                195                 200                 205
Tyr Asn Gly Asp Asn Phe Asp Phe Ala Tyr Leu Lys Lys Arg Ser Glu
                210                 215                 220
Thr Leu Gly Val Lys Phe Ile Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
                260                 265                 270
Tyr Thr Leu Glu Thr Val Tyr Glu Ala Ile Phe Gly Gln Pro Lys Glu
                275                 280                 285
Lys Val Tyr Ala Glu Glu Ile Ala Gln Ala Trp Glu Ser Gly Glu Gly
                290                 295                 300
Leu Glu Arg Val Ala Arg Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Ser Leu Trp Asp Val Ser Arg Ser Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Asp Glu Arg Glu Leu Ala Arg Arg Ala Glu Ser Tyr
                370                 375                 380
Ala Gly Gly Tyr Val Lys Glu Pro Glu Lys Gly Leu Trp Glu Asn Ile
385                 390                 395                 400
Val Tyr Leu Asp Tyr Lys Ser Leu Tyr Pro Ser Ile Ile Ile Thr His
                405                 410                 415
Asn Val Ser Pro Asp Thr Leu Asn Arg Glu Gly Cys Arg Glu Tyr Asp
                420                 425                 430
Val Ala Pro Gln Val Gly His Arg Phe Cys Lys Asp Phe Pro Gly Phe
                435                 440                 445
Ile Pro Ser Leu Leu Gly Asp Leu Leu Glu Glu Arg Gln Lys Val Lys
                450                 455                 460
Lys Lys Met Lys Ala Thr Val Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Asn Ala Arg Trp Tyr Cys Arg Glu Cys Ala Glu Ser
                500                 505                 510
```

Val Thr Ala Trp Gly Arg Gln Tyr Ile Glu Thr Thr Met Arg Glu Ile
            515                 520                 525

Glu Glu Lys Phe Gly Phe Lys Val Leu Tyr Ala Asp Thr Asp Gly Phe
        530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr Gly Ser
770                 775

<210> SEQ ID NO 65
<211> LENGTH: 777
<212> TYPE: PRT
<213> ORGANISM: Artificial sequence
<220> FEATURE:
<223> OTHER INFORMATION: Chimeric sequence

<400> SEQUENCE: 65

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asn Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60

Val Thr Arg Ala Glu Arg Val Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

```
Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asn Glu Glu Leu Arg Met Leu Ala Phe Asp Ile Glu Thr
130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
            195                 200                 205

Tyr Asn Gly Asp Asn Phe Asp Phe Ala Tyr Leu Lys Lys Arg Ser Glu
            210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Ala Ile Phe Gly Gln Pro Lys Glu
            275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
            355                 360                 365

Pro Asn Lys Pro Ser Glu Glu Glu Tyr Gln Arg Arg Leu Arg Glu Ser
            370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
            450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510
```

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
        755                 760                 765

Trp Leu Asn Ile Lys Lys Lys Gly Ser
770                 775

<210> SEQ ID NO 66
<211> LENGTH: 774
<212> TYPE: PRT
<213> ORGANISM: Artificial sequence
<220> FEATURE:
<223> OTHER INFORMATION: Chimeric sequence

<400> SEQUENCE: 66

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asn Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60

Val Thr Arg Ala Glu Arg Val Lys Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asn Glu Glu Leu Arg Met Leu Ala Phe Asp Ile Glu Thr
    130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
            195                 200                 205

Tyr Asn Gly Asp Asn Phe Asp Phe Ala Tyr Leu Lys Lys Arg Ser Glu
    210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Ala Ile Phe Gly Gln Pro Lys Glu
            275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
            355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu

```
            515                 520                 525
Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Ile Lys Lys Lys
545                 550                 555                 560

Ala Leu Glu Phe Val Lys Tyr Ile Asn Ser Lys Leu Pro Gly Leu Leu
            565                 570                 575

Glu Leu Gly Tyr Glu Gly Phe Tyr Ala Arg Gly Phe Phe Val Thr Lys
        580                 585                 590

Lys Lys Tyr Ala Leu Ile Asp Glu Gly Lys Ile Val Thr Arg Gly
    595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Asp Glu Ala
625                 630                 635                 640

Val Lys Ile Val Lys Glu Val Thr Glu Lys Leu Ser Lys Tyr Glu Ile
            645                 650                 655

Pro Pro Glu Lys Leu Val Ile Tyr Glu Gln Ile Thr Arg Pro Leu Ser
            660                 665                 670

Glu Tyr Lys Ala Ile Gly Pro His Val Ala Val Ala Lys Arg Leu Ala
        675                 680                 685

Ala Lys Gly Val Lys Val Lys Pro Gly Met Val Ile Gly Tyr Ile Val
    690                 695                 700

Leu Arg Gly Asp Gly Pro Ile Ser Lys Arg Ala Ile Ala Ile Glu Glu
705                 710                 715                 720

Phe Asp Pro Lys Lys His Lys Tyr Asp Ala Glu Tyr Tyr Ile Glu Asn
            725                 730                 735

Gln Val Leu Pro Ala Val Glu Arg Ile Leu Arg Ala Phe Gly Tyr Arg
            740                 745                 750

Lys Glu Asp Leu Lys Tyr Gln Lys Thr Lys Gln Val Gly Leu Gly Ala
        755                 760                 765

Trp Leu Lys Phe Gly Ser
    770

<210> SEQ ID NO 67
<211> LENGTH: 777
<212> TYPE: PRT
<213> ORGANISM: Pyrococcus sp. (strain GB-D)

<400> SEQUENCE: 67

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
            85                  90                  95

Arg Asp Lys Ile Arg Glu His Ser Ala Val Ile Asp Ile Phe Glu Tyr
            100                 105                 110
```

-continued

```
Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
        290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
```

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
        755                 760                 765

Trp Leu Asn Ile Lys Lys Gly Ser
    770                 775

<210> SEQ ID NO 68
<211> LENGTH: 773
<212> TYPE: PRT
<213> ORGANISM: Pyrococcus abyssi

<400> SEQUENCE: 68

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
    50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

```
Met Glu Gly Asn Glu Glu Leu Thr Phe Leu Ala Val Asp Ile Glu Thr
        130                 135                 140

Leu Tyr His Glu Gly Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Ser Ser Glu Arg Glu Met Ile Lys
                180                 185                 190

Arg Leu Val Lys Val Ile Arg Glu Lys Asp Pro Asp Val Ile Ile Thr
                195                 200                 205

Tyr Asn Gly Asp Asn Phe Asp Phe Pro Tyr Leu Leu Lys Arg Ala Glu
210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
                260                 265                 270

Tyr Thr Leu Glu Ala Val Tyr Glu Ala Ile Phe Gly Lys Ser Lys Glu
                275                 280                 285

Lys Val Tyr Ala His Glu Ile Ala Glu Ala Trp Glu Thr Gly Lys Gly
                290                 295                 300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Arg Glu Tyr Glu Arg Arg Leu Arg Glu Ser
370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Thr
                405                 410                 415

His Asn Val Ser Pro Asp Thr Leu Asn Arg Glu Asn Cys Lys Glu Tyr
                420                 425                 430

Asp Val Ala Pro Gln Val Gly His Arg Phe Cys Lys Asp Phe Pro Gly
                435                 440                 445

Phe Ile Pro Ser Leu Leu Gly Asn Leu Leu Glu Glu Arg Gln Lys Ile
450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Gln Tyr Ile Asp Leu Val Arg Arg Glu
                515                 520                 525

Leu Glu Ser Arg Gly Phe Lys Val Leu Tyr Ile Asp Thr Asp Gly Leu
                530                 535                 540

Tyr Ala Thr Ile Pro Gly Ala Lys His Glu Glu Ile Lys Glu Lys Ala
```

```
            545                 550                 555                 560
Leu Lys Phe Val Glu Tyr Ile Asn Ser Lys Leu Pro Gly Leu Leu Glu
                565                 570                 575

Leu Glu Tyr Glu Gly Phe Tyr Ala Arg Gly Phe Phe Val Thr Lys Lys
                580                 585                 590

Lys Tyr Ala Leu Ile Asp Glu Glu Gly Lys Ile Val Thr Arg Gly Leu
                595                 600                 605

Glu Ile Val Arg Arg Asp Trp Ser Glu Ile Ala Lys Glu Thr Gln Ala
    610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
                660                 665                 670

Tyr Lys Ala Ile Gly Pro His Val Ala Val Ala Lys Arg Leu Ala Ala
                675                 680                 685

Lys Gly Val Lys Val Lys Pro Gly Met Val Ile Gly Tyr Ile Val Leu
690                 695                 700

Arg Gly Asp Gly Pro Ile Ser Lys Arg Ala Ile Ala Ile Glu Glu Phe
705                 710                 715                 720

Asp Pro Lys Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Lys Tyr Gln Lys Thr Lys Gln Val Gly Leu Gly Ala Trp
                755                 760                 765

Leu Lys Phe Gly Ser
        770

<210> SEQ ID NO 69
<211> LENGTH: 775
<212> TYPE: PRT
<213> ORGANISM: Thermococcus waiotapuensis

<400> SEQUENCE: 69

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asn Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60

Val Thr Arg Ala Glu Arg Val Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asn Glu Glu Leu Arg Met Leu Ala Phe Asp Ile Glu Thr
    130                 135                 140
```

-continued

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
            165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Ala Ile Phe Gly Gln Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Ala Glu Ser Tyr
    370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Thr His
                405                 410                 415

Asn Val Ser Pro Asp Thr Leu Asn Arg Glu Gly Cys Arg Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu

```
                    565                 570                 575
Leu Glu Tyr Glu Gly Phe Tyr Arg Arg Gly Phe Phe Val Thr Lys Lys
            580                 585                 590

Lys Tyr Ala Val Ile Asp Glu Glu Asp Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg Tyr Glu Val Pro
                    645                 650                 655

Pro Glu Lys Leu Val Ile Tyr Glu Gln Ile Thr Arg Asn Leu Arg Asp
            660                 665                 670

Tyr Arg Ala Thr Gly Pro His Val Ala Val Ala Lys Arg Leu Ala Ala
                    675                 680                 685

Arg Gly Ile Lys Ile Arg Pro Gly Thr Val Ile Ser Tyr Ile Val Leu
            690                 695                 700

Lys Gly Pro Gly Arg Val Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
                    725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Ala Gly Leu Gly Ala Trp
            755                 760                 765

Leu Lys Pro Lys Thr Gly Ser
            770                 775

<210> SEQ ID NO 70
<211> LENGTH: 776
<212> TYPE: PRT
<213> ORGANISM: Thermococcus kodakaraensis

<400> SEQUENCE: 70

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160
```

Ser Tyr Ala Asp Glu Glu Gly Ala Arg Val Ile Thr Trp Lys Asn Val
            165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
            195                 200                 205

Tyr Asn Gly Asp Asn Phe Asp Phe Ala Tyr Leu Lys Lys Arg Cys Glu
            210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
            275                 280                 285

Lys Val Tyr Ala Glu Glu Ile Thr Thr Ala Trp Glu Thr Gly Glu Asn
            290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
            325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Arg Gln Ser Tyr
            370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
            405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
            485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
            530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
            565                 570                 575

Leu Glu Tyr Glu Gly Phe Tyr Lys Arg Gly Phe Phe Val Thr Lys Lys

```
                    580                 585                 590
Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
            610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
            755                 760                 765

Leu Lys Pro Lys Gly Thr Gly Ser
            770                 775

<210> SEQ ID NO 71
<211> LENGTH: 777
<212> TYPE: PRT
<213> ORGANISM: Pyrococcus furiosus

<400> SEQUENCE: 71

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175
```

```
Asp Leu Pro Tyr Val Glu Val Val Ser Ser Arg Glu Met Ile Lys
            180                 185                 190

Arg Phe Leu Arg Ile Ile Arg Glu Lys Asp Pro Asp Ile Ile Val Thr
    195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Thr Arg Thr Ile Asn Leu Pro Thr
        260                 265                 270

Tyr Thr Leu Glu Ala Val Tyr Glu Ala Ile Phe Gly Lys Pro Lys Glu
    275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
            325                 330                 335

Val Gly Gln Pro Leu Trp Asp Val Ser Arg Ser Ser Thr Gly Asn Leu
        340                 345                 350

Val Glu Trp Phe Leu Leu Arg Lys Ala Tyr Glu Arg Asn Glu Val Ala
    355                 360                 365

Pro Asn Lys Pro Ser Glu Glu Glu Tyr Gln Arg Arg Leu Arg Glu Ser
370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
            405                 410                 415

His Asn Val Ser Pro Asp Thr Leu Asn Leu Glu Gly Cys Lys Asn Tyr
        420                 425                 430

Asp Ile Ala Pro Gln Val Gly His Lys Phe Cys Lys Asp Ile Pro Gly
    435                 440                 445

Phe Ile Pro Ser Leu Leu Gly His Leu Leu Glu Glu Arg Gln Lys Ile
450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
            485                 490                 495

Tyr Tyr Gly Tyr Ala Lys Ala Arg Trp Tyr Cys Lys Glu Cys Ala Glu
        500                 505                 510

Ser Val Thr Ala Trp Gly Arg Lys Tyr Ile Glu Leu Val Trp Lys Glu
    515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
            565                 570                 575

Glu Leu Glu Tyr Glu Gly Phe Tyr Lys Arg Gly Phe Phe Val Thr Lys
        580                 585                 590

Lys Arg Tyr Ala Val Ile Asp Glu Glu Gly Lys Val Ile Thr Arg Gly
```

```
                    595                 600                 605
Leu Glu Ile Val Arg Arg Asp Trp Ser Glu Ile Ala Lys Glu Thr Gln
        610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser Gly Ser
    770                 775

<210> SEQ ID NO 72
<211> LENGTH: 37
<212> TYPE: PRT
<213> ORGANISM: Artificial sequence
<220> FEATURE:
<223> OTHER INFORMATION: synthetic peptide

<400> SEQUENCE: 72

Met Gly Ser Ser His Gly His His His His His His Gly Val Gly
1               5                   10                  15

Gly Trp Ser His Pro Gln Phe Glu Lys Gly Gly Thr Glu Asn Leu Tyr
            20                  25                  30

Phe Gln Gly Gly His
        35
```